(12) United States Patent
Mehta et al.

(10) Patent No.: US 7,488,748 B2
(45) Date of Patent: Feb. 10, 2009

(54) 3,6-DISUBSTITUTED AZABICYCLO HEXANE DERIVATIVES AS MUSCARINIC RECEPTOR ANTAGONISTS

(75) Inventors: Anita Mehta, Plainfield, IL (US); Arundutt V. Silamkoti, Secunderabad (IN); Naresh Kumar, Haryana (IN); Jang Bahadur Gupta, Hyogo (JP)

(73) Assignee: Ranbaxy Laboratories Limited, Gurgaon (IN)

( * ) Notice: Subject to any disclaimer, the term of this patent is extended or adjusted under 35 U.S.C. 154(b) by 0 days.

(21) Appl. No.: 10/543,585

(22) PCT Filed: Jan. 23, 2003

(86) PCT No.: PCT/IB03/00256

§ 371 (c)(1),
(2), (4) Date: May 6, 2006

(87) PCT Pub. No.: WO2004/067510

PCT Pub. Date: Aug. 12, 2004

(65) Prior Publication Data

US 2006/0247225 A1 Nov. 2, 2006

(51) Int. Cl.
*A61K 31/403* (2006.01)
*C07D 209/52* (2006.01)
(52) U.S. Cl. ..................... 514/412; 548/515
(58) Field of Classification Search ............... 548/515; 514/412
See application file for complete search history.

(56) References Cited

U.S. PATENT DOCUMENTS

| | | | | |
|---|---|---|---|---|
| 3,176,019 | A | 3/1965 | Campbell et al. | 260/293.4 |
| 4,595,690 | A | 6/1986 | Clark et al. | 514/356 |
| 5,281,601 | A | 1/1994 | Cross et al. | 514/320 |
| 5,948,792 | A | 9/1999 | Tsuchiya et al. | 514/317 |
| 6,130,232 | A | 10/2000 | Mase et al. | 514/318 |
| 6,174,900 | B1 | 1/2001 | Okada et al. | 514/317 |
| 6,559,162 | B2 * | 5/2003 | Bjorsne et al. | 514/299 |

FOREIGN PATENT DOCUMENTS

| | | |
|---|---|---|
| EP | 0 325 571 | 7/1989 |
| EP | 0 383 256 | 8/1990 |
| EP | 0 388 054 | 9/1990 |
| EP | 0 751 127 | 1/1997 |
| EP | 0 801 067 | 10/1997 |
| EP | 0 823 423 | 2/1998 |
| EP | 0 863 141 | 9/1998 |
| EP | 0 930 298 | 7/1999 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 95/06635 | 3/1995 |
| WO | WO 96/33973 | 10/1996 |
| WO | WO 97/45414 | 12/1997 |
| WO | WO 98/05641 | 2/1998 |
| WO | WO 98/29402 | 7/1998 |

OTHER PUBLICATIONS

Morissette et al. Advanced Drug Delivery Reviews 2004, 56, 275-300.*
Wess et al. Life Sciences 2003, 72, 2047-2054.*
O'Neill, M. Drug Discovery Today Oct. 2005, 10(20), 1338.*
Michel et al. Naunyn-Schmiedeberg's Arch Pharmacol 2006, 374, 79-85.*
Latifpour et al. The Journal of Pharmacology and Experimental Therapeutics 1989, 249(1), 81-88.*
Carrier et al. The Journal of Pharmacology and Experimental Therapeutics 1987, 242(2), 531-535.*
Ahren et al. Diabetologia 1996, 39, 383-390.*
Abrams et al. British Journal of Pharmacology 2006, 148, 565-578.*
Birdsall et al., "Muscarinic receptors: it's a knockout", *Trends in Pharmacological Sciences*, 22(5):215-219 (2001).
Chapple, "Muscarinic receptor antagonists in the treatment of overactive bladder", *Urology*, 55(Suppl. 5A):33-46 (2000).
Eglen et al., "Theraputic opportunities from muscarinic receptor research", *Trends in Pharmacological Sciences*, 22(8):409-414 (2001).
Felder et al., "Theraputic Opportunities for Muscarinic Receptors in the Central Nervous System", *Journal of Medicinal Chemistry*, 43(23):4333-4353 (2000).
Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).
Kadin and Cannon, "Esters of N-Methyl-3-hydroxypiperidine Having Psychotomimetic Activity. II", *Journal of Organic Chemistry*, 27:240-245 (1962).
Lee et al, "Evaluation of Stereoisomers of 4-Fluoroalkyl Analogues of 3-Quinuclidinyl Benzilate in In Vivo Competition Studies for the M1, M2 and M3 Muscarinic Receptor Subtypes in Brain", *Nuclear Medicine and Biology*, 22(6):773-781 (1995) XP004051742, ISSN: 0969-8051.
Steers, "The future direction of neuro-urology drug research", *Current Opinion in CPNS Investigational Drugs*, 2(3):268-282.
Cheng and Prusoff, "Relationship between the inhibition constant (KI) and the concentration of inhibitor which causes 50 per cent inhibition (I50) of an enzymatic reaction", *Biochemical Pharmacology*, 22:3099-3108 (1973).

(Continued)

*Primary Examiner*—Kamal A Saeed
*Assistant Examiner*—Jason M Nolan
(74) *Attorney, Agent, or Firm*—Jayadeep R. Deshmukh, Esq.; George E. Heibel, Esq.

(57) ABSTRACT

This invention generally relates to derivatives of 3,6 disubstituted azabicyclo hexanes. The compounds of this invention can function as muscarinic receptor antagonists and can be used for the treatment of various diseases of the respiratory, urinary and gastrointestinal systems mediated through muscarinic receptors. The invention also relates to pharmaceutical compositions containing the compounds of the present invention and the methods of treating the diseases mediated through muscarinic receptors.

25 Claims, No Drawings

OTHER PUBLICATIONS

Eglen et al., "Muscarinic receptor ligands and their theraputic potential", *Current Opinion in Chemical Biology*, 3:426-432 (1999).

Shacklett and Smith, "The Preparation of Substituted Benzilic Acids", *Journal of the American Chemical Society*, 75:2654-2657 (1953).

Sagara et al., "Cyclohexylmethylpiperidinyltriphenylpropioamide: A Selective Muscarinic M3 Antagonist Discriminating against the Other Receptor Subtypes", *Journal of Medicinal Chemistry*, 45:984-987 (2002).

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Broadley and Kelly, "Muscarinic Receptor Agonists and Antagonists", *Molecules*, 6:142-193 (2001).

Kubo et al., "Cloning, sequencing and expression of complementary DNA encoding the muscarinic acetylcholine receptor", *Nature*, 323(2):411-416 (1986).

Horning, E.C., 1955, *Organic Syntheses, Collective Vol. 3*. Hoboken, NJ: John Wiley and Sons, p. 220.

de Groat and Yoshimura, "Pharmacology of the Lower Urinary Tract", *Annual Review of Pharmacology and Toxicology*, 41:691-721 (2001).

Bonner et al., "Identification of a Family of Muscarinic Acetylcholine Receptor Genes", *Science*, 237:527-531 (1987).

Biel et al., "Central Stimulants. II. Cholinergic Blocking Agents[1]", *Journal of Organic Chemistry*, 26:4096-4103 (1961).

Taniguchi et al, "Agents for the Treatment of Overactive Detrusor. VI[∞]. Synthesis and Pharmacological Properties of Acetamide Derivatives Bearing Cyclic Amines in N-Substituents", *Chemical and Pharmaceutical Bulletin*, 42(1):74-84 (1994).

* cited by examiner

3,6-DISUBSTITUTED AZABICYCLO HEXANE DERIVATIVES AS MUSCARINIC RECEPTOR ANTAGONISTS

FIELD OF THE INVENTION

This invention generally relates to derivatives of 3,6-disubstituted azabicyclo hexanes.

The compounds of this invention can function as muscarinic receptor antagonists and can be used for the treatment of various diseases of the respiratory, urinary and gastrointestinal systems mediated through muscarinic receptors.

The invention also relates to pharmaceutical compositions containing the compounds of the present invention and the methods of treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527). A review in *Current Opinions in Chemical Biology*, 1999; 3: 426, as well as in *Trends in Pharmacological Sciences*, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in *J. Med. Chem.*, 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules*, 2001, 6: 142.

N. J. M. Birdsall et. al. in *Trends in Pharmacological Sciences*, 2001; 22: 215 have also summarized the recent developments on the role of different muscarinic receptor subtypes using different muscarinic receptors of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of *Pharmacological Toxicol.*, 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in *Curr. Opin. Invest. Drugs*, 2: 268, C. R. Chapple et. al. in *Urology*, 55: 33), Steers W D, Barrot D M, Wein A J, 1996, Voiding dysfunction: diagnosis classification and management. In "Adult and Pediatric Urology," ed. J Y Gillenwatter, J T Grayhack, S S Howards, J W Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other close art references.

A report in *J. Med. Chem.*, 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides 3,6-disubstituted azabicyclo hexanes which function as muscarinic receptor antagonists and are useful as safe treatment of various diseases of the respiratory, urinary and gastrointestinal systems, and methods for the syntheses of the compounds. The present invention includes 3,6-disubstituted azabicyclo [3.1.0], [3.1.1] and [3.1.2] hexanes.

The invention also provides pharmaceutical compositions containing the compounds, and which may also contain acceptable carriers, excipients or diluents which are useful for the treatment of various diseases of the respiratory, urinary and gastrointestinal systems.

The present invention also includes within its scope prodrugs of the compounds. In general, such prodrugs are functionalized derivatives of these compounds which readily get converted in vivo into the defined compounds. Conventional procedures for the selection and preparation of suitable prodrugs are known to the artisan of ordinary skill in the art.

The invention also includes the enantiomers, diastereomers, N-oxides, polymorphs, pharmaceutically acceptable salts, pharmaceutically acceptable solvates, esters and metabolities of these compounds having the same type of activity.

The invention further includes pharmaceutical compositions comprising the compounds of the present invention, their enantiomers, diastereomers, prodrugs, N-oxides, polymorphs, pharmaceutically acceptable salts, pharmaceutically acceptable solvates, esters, or metabolites in combination with a pharmaceutically acceptable carrier and optionally included excipients.

Other advantages of the invention will be set forth in the description which follows, and in part will be apparent from the description or may be learnt by the practice of the invention. The objects and the advantages of the invention may be realized and obtained by means of the mechanisms and combinations pointed out in the appended claims.

In accordance with one aspect of the present invention, there is provided a compound having the structure of Formula I:

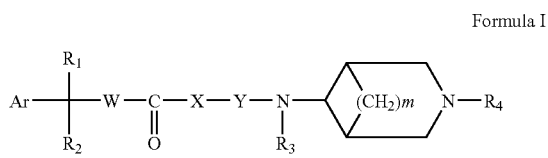

Formula I and its pharmaceutically acceptable salts, pharmaceutically acceptable solvates, esters, enantiomers, diastereomers, N-oxides, polymorphs, prodrugs, or metabolites, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), trifluoromethyl cyano, hydroxy, nitro, halogen (e.g. F, Cl, Br or I), lower alkoxy ($C_1$-$C_4$), amino or lower alkylamino ($C_1$-$C_4$);

$R_1$ represents a hydrogen, hydroxy, hydroxymethyl, loweralkyl ($C_1$-$C_4$), amino, alkoxy, cycloalkyl ($C_3$-$C_7$), carbamoyl, halogen (e.g. F, Cl, Br, I) or aryl;

$R_2$ represents alkyl, $C_3$-$C_7$ cycloalkyl ring, $C_3$-$C_7$ cycloalkenyl ring, an aryl or a heteroaryl ring having 1 to 2 hetero atoms selected from the group consisting of oxygen, sulphur and nitrogen atoms; the aryl or a hetero aryl ring may be unsubstituted or substituted by one to three substituents independently selected from lower alkyl ($C_1$-$C_4$), trifluoromethyl, cyano, hydroxy, nitro, lower alkoxycarbonyl, halogen, lower alkoxy ($C_1$-$C_4$), unsubstituted amino or lower alkyl ($C_1$-$C_4$) amino;

W represents $(CH_2)_p$, where p represents 0 to 1;

X represents an oxygen, sulphur, NR or no atom wherein R represents hydrogen or $C_{1-6}$ alkyl;

Y represents $CHR_5CO$ wherein $R_5$ represents hydrogen or methyl or $(CH_2)q$ wherein q represents 0 to 4;

m represents 0 to 2;

$R_3$ represents hydrogen, lower alkyl ($C_1$-$C_4$) or $CO_2C(CH_3)_3$;

$R_4$ represents $C_1$-$C_{15}$ saturated or unsaturated aliphatic hydrocarbon (straight chain or branched) in which any 1 to 6 hydrogen atoms may be substituted with the group independently selected from halogen (e.g. F, Cl, Br, I), carboxylic acid, carboxylic acid ester, aryl, aryloxy, arylalkyl, arylalkenyl, heteroaryl, heteroarylalkyl, heteroarylalkenyl having 1 to 2 hetero atoms selected from the group consisting of nitrogen, oxygen and sulphur with an option that any 1 to 5 hydrogen atoms on an aryl or heteroaryl ring in said aryl, aryloxy, arylalkyl, arylalkenyl, heteroaryl, heteroarylalkenyl group may be substituted with lower alkyl, trifluoromethyl, halogen (e.g. F, Cl, Br, I), cyano, nitro, hydroxy, lower ($C_1$-$C_4$)alkoxy, amino, lower ($C_1$-$C_4$)alkylamino, sulphonylamino, amide, carboxylic acid, carboxylic acid ester or benzyl ester.

In accordance with a second aspect of the present invention, there is provided a compound having the structure of Formula II and its pharmaceutically acceptable salts, pharmaceutically acceptable solvates, esters, enantiomers, diastereomers, N-oxides, polymorphs, prodrugs, metabolites, wherein Ar, $R_1$, $R_2$, $R_3$, $R_4$, W, X and Y are as defined for Formula I.

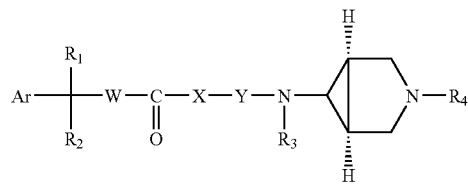

Formula II

In accordance with a third aspect of the present invention, there is provided a compound having the structure of Formula III and its pharmaceutically acceptable salts, pharmaceutically acceptable solvates, esters, enantiomers, diastereomers, N-oxides, polymorphs, prodrugs, metabolites, wherein Ar, $R_1$, $R_2$, $R_3$ and $R_4$ are as defined for Formula I

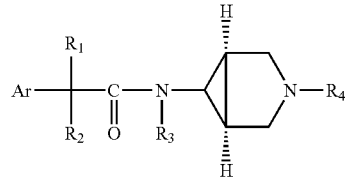

Formula III

In accordance with a fourth aspect of the present invention, there is provided a compound having the structure of Formula IV and its pharmaceutically acceptable salts, pharmaceutically acceptable solvates, esters, enantiomers, diastereomers, N-oxides, polymorphs, prodrugs, metabolites, wherein Ar, $R_1$, $R_3$ and $R_4$ are as defined for Formula I and r is 1 to 4.

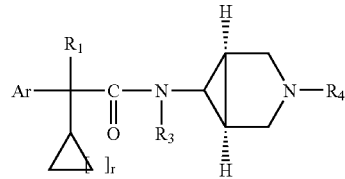

Formula IV

In accordance with a fifth aspect of the present invention, there is provided a compound having the structure of Formula V and its pharmaceutically acceptable salts, pharmaceutically acceptable solvates, esters, enantiomers, diastereomers, N-oxides, polymorphs, prodrugs, metabolites, wherein Ar, $R_1$, $R_3$ and $R_4$ are as defined for Formula I and s is 1 to 3.

Formula V

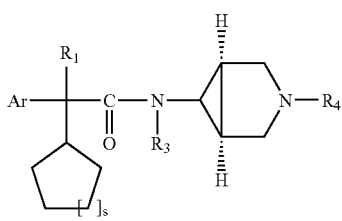

In accordance with a sixth aspect of the present invention, there is provided a compound having the structure of Formula VI and its pharmaceutically acceptable salts, pharmaceutically acceptable solvates, esters, enantiomers, diastereomers, N-oxides, polymorphs, prodrugs, metabolites, wherein Formula VI wherein $R_3$, $R_4$ and s are the same as defined for Formula V.

Formula VI

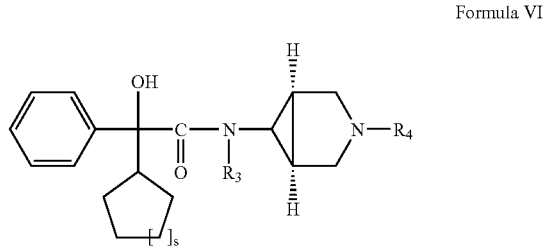

In accordance with a seventh aspect of the present invention, there is provided a method for treatment or prophylaxis of an animal or a human suffering from a disease or disorder of the respiratory, urinary and gastrointestinal systems, wherein the disease or disorder is mediated through muscarinic receptors, comprising administering to a patient in need thereof, an effective amount of compounds as described above.

In accordance with an eighth aspect of the present invention, there is provided a method for treatment or prophylaxis of an animal or a human suffering from a disease or disorder of the respiratory systems such as bronchial asthma, chronic obstructive pulmonary disorders (COPD), pulmonary fibrosis, etc., urinary system which induce such urinary disorders as urinary incontinence, lower urinary tract systems (LUTS), etc., and gastrointestinal system such as irritable bowel syndrome, obesity, diabetes and gastrointestinal hyperkinesis with compounds as described above, wherein the disease or disorder is associated with muscarinic receptors, comprising administering to a patient in need thereof, an effective amount of compounds as described above.

In accordance with a ninth aspect of the present invention, there is provided a process for preparing the compounds as described above.

The compounds of the present invention exhibit significant potency in terms of their activity, which was determined by in vitro receptor binding and functional assays and in vitro experiments using anaesthetized rabbit. Compounds were tested in vitro and in vitro. Some compounds were found to function as potent muscarinic receptor antagonists with high affinity towards $M_3$ receptors. Therefore, the present invention provides pharmaceutical compositions for treatment of diseases or disorders associated with muscarinic receptors.

Compounds and compositions described herein can be administered orally or parenterally.

DETAILED DESCRIPTION OF THE INVENTION

The compounds described herein may be prepared by the reaction sequence as show in Scheme-I.

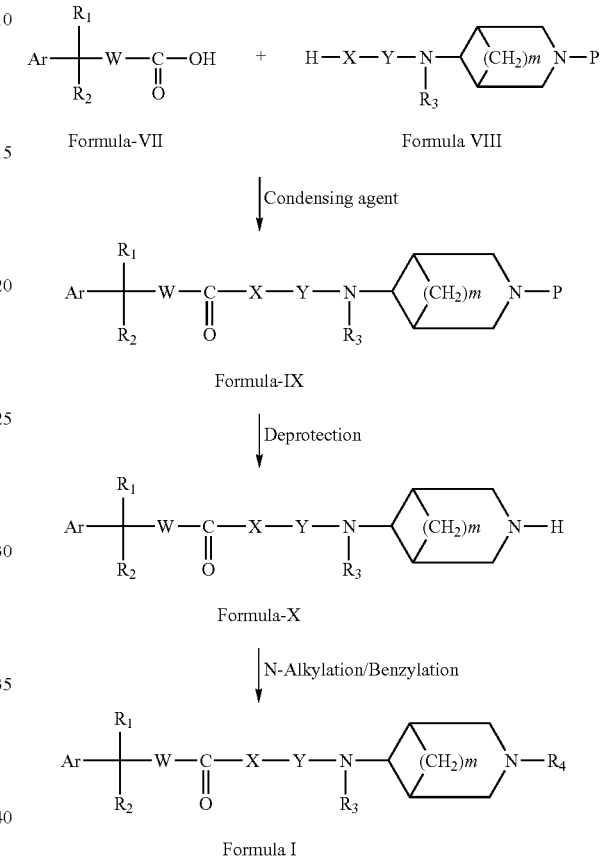

The preparation comprises condensing a compound of Formula VII with the compound of Formula VIII, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), trifluoromethyl cyano, hydroxy, nitro, halogen (e.g. F, Cl, Br or I), lower alkoxy ($C_1$-C4), amino or lower alkylamino ($C_1$-$C_4$);

$R_1$ represents a hydrogen, hydroxy, hydroxymethyl, loweralkyl ($C_1$-$C_4$), amino, alkoxy, cycloalkyl ($C_3$-$C_7$), carbamoyl, halogen (e.g. F, Cl, Br, I) or aryl;

$R_2$ represents alkyl, $C_3$-$C_7$ cycloalkyl ring, $C_3$-$C_7$ cycloalkenyl ring, an aryl or a heteroaryl ring having 1 to 2 hetero atoms selected from the group consisting of oxygen, sulphur and nitrogen atoms; the aryl or a hetero aryl ring may be unsubstituted or substituted by one to three substituents independently selected from lower alkyl ($C_1$-C4), trifluoromethyl, cyano, hydroxy, nitro, lower alkoxycarbonyl, halogen, lower alkoxy ($C_1$-$C_4$), unsubstituted amino or lower alkyl ($C_1$-$C_4$) amino;

W represents $(CH_2)_p$, where p represents 0 to 1;

X represents an oxygen, sulphur, NR or no atom wherein R represents hydrogen or $C_{1-6}$ alkyl;

Y represents CHR$_5$CO wherein R$_5$ represents hydrogen or methyl or (CH$_2$)q wherein q represents 0 to 4;

m represents 0 to 2;

R$_3$ represents hydrogen, lower alkyl (C$_1$-C$_4$) or CO$_2$C(CH$_3$)$_3$;

P is any group which can be used to protect an amino group and is selected from benzyl and t-butyloxy carbonyl groups, in the presence of a condensing agent to give a protected compound of Formula IX wherein R$_1$, R$_2$, R$_3$, W, X, Y, P and m are as defined earlier, which on deprotection through reaction with a deprotecting agent in an organic solvent gives an unprotected compound of Formula X wherein R$_1$, R$_2$, R$_3$, W, X, Y and m are the same as defined earlier, which is finally N-alkylated or benzylated with a suitable alkylating or benzylating agent L-R$_4$ wherein L is any leaving group known in the art, to give a compound of Formula I.

The reaction of the compound of Formula VII with a compound of Formula VIII to give a compound of Formula IX can be carried out in the presence of a condensing agent, for example 1-(3-dimethylaminopropyl)-3-ethyl carbodiimide hydrochloride (EDC) and 1,8-diazabicyclo [5.4.0]undec-7-ene (DBU).

The reaction of the compound of Formula VII with a compound of Formula VIII to give a compound of Formula IX can be carried out in a suitable solvent, for example N,N-dimethylformamide, dimethylsulfoxide, toluene and xylene at a temperature ranging from about 0-140° C.

The deprotection of the compound of Formula IX to give a compound of Formula X can be carried out with a deprotecting agent, for example palladium on carbon, trifluoroacetic acid (TFA) and hydrochloric acid.

The deprotection of the compound of Formula IX to give a compound of Formula X can be carried out in a suitable organic solvent, for example methanol, ethanol, tetrahydrofuran and acetonitrile at temperatures ranging from about 10-50° C.

The N-alkylation or benzylation of the compound of Formula X to give a compound of Formula I can be carried out with a suitable alkylating or benzylating agent, L-R$_4$ wherein L is any leaving group, known in the art, for example halogen, O-mestyl and O-tosyl group.

The N-alkylation or benzylation of the compound of Formula X to give a compound of Formula I can be carried out in a suitable organic solvent such as N,N-dimethylformamide dimethylsulfoxide, tetrahydrofaran and acetonitrile, at temperatures ranging from about 25 to about 100° C.

In the above scheme, where specific bases, condensing agents, protecting groups, deprotecting agents, N-alkylating/benzylating agents, solvents, catalysts etc. are mentioned, it is to be understood that other bases, condensing agents, protecting groups, deprotecting agents, N-alkylating/benzylating agents, solvents, catalysts etc. known to those skilled in the art may be used. Similarly, the reaction temperature and duration may be adjusted according to the desired needs.

An illustrative list of particular compounds which are capable of being produced by Scheme I and shown in Table 1 include:

Compound Chemical Name No.
1. (1α,5α,6α)-N-[3-(4-methyl-3-pentenyl)-3-azabicyclo[3.1.0]hex-6-yl]-2-hydroxy-2-cyclopentyl-2-(4-methoxy)phenylacetamide
2. (1α,5α,6α)-N-[3-(2-thienylmethyl)-3-azabicyclo[3.1.0]hex-6-yl]-2-hydroxy-2-cyclohexyl-2-phenylacetamide
3. (1α,5α,6α)-N-[3-(2-thienylmethyl)-3-azabicyclo[3.1.0]hex-6-yl]-2-hydroxy-2-cyclopentyl-2-phenylacetamide
4. (1α,5α,6α)-N-[3-(5-nitro-2-furylmethyl)-3-azabicyclo[3.1.0]hex-6-yl]-2-hydroxy-2-cyclopentyl-2-phenylacetamide
5. (1α,5α,6α)-N-[3-(4-methyl-pentyl)-3-azabicyclo[3.1.0]hex-6-yl]-2-hydroxy-2-cyclopentyl-2-phenylacetamide
6. (1α,5α,6α)-N-[3-(2-(1,4-benzodioxan-6-yl)ethyl)-3-azabicyclo[3.1.0]hex-6-yl]-2-hydroxy-2-cyclopentyl-2-phenylacetamide
7. (1α,5α,6α)-N-[3-(3,4,5-trimethoxyphenethyl-3-azabicyclo[3.1.0]hex-6-yl]-2-hydroxy-2-cyclopentyl-2-phenylacetamide
8. (1α,5α,6α)-N-[3-[3-(3,4-methyldioxyphenyl)propyl)]-3-azabicyclo[3.1.0]hex-6-yl]-2-hydroxy-2-cyclopentyl-2-phenylacetamide
9. (1α,5α,6α)-N-[3-(3,4,5-trimethoxybenzyl)-3-azabicyclo[3.1.0]hex-6-yl]-2-hydroxy-2-cyclopentyl-2-phenylacetamide
10. (1α,5α,6α)-N-[3-(3,5-dimethoxybenzyl)-3-azabicyclo[3.1.0]hex-6-yl]-2-hydroxy-2-cyclopentyl-2-phenylacetamide
11. (1α,5α,6α)-N-[3-(3,4-dimethoxybenzyl)-3-azabicyclo[3.1.0]hex-6-yl]-2-hydroxy-2-cyclopentyl-2-phenylacetamide
12. (1α,5α,6α)-N-[3-(3-methoxybenzyl)-3-azabicyclo[3.1.0]hex-6-yl]-2-hydroxy-2-cyclopentyl-2-phenylacetamide
13. (1α,5α,6α)-N-[3-(4-trifluoromethylbenzyl)-3-azabicyclo[3.1.0]hex-6-yl]-2-hydroxy-2-cyclopentyl-2-phenylacetamide
14. (1α,5α,6α)-N-[3-(5-methyl-2-furylmethyl)-3-azabicyclo[3.1.0]hex-6-yl]-2-hydroxy-2-cyclopentyl-2-phenylacetamide
15. (1α,5α,6α)-N-[3-(2-(4-methylphenoxy)ethyl)-3-azabicyclo[3.1.0]hex-6-yl]-2-hydroxy-2-cyclopentyl-2-phenylacetamide
16. (1α,5α,6α)-N-[3-(3-nitrobenzyl-3-azabicyclo[3.1.0]hex-6-yl]-2-hydroxy-2-cyclopentyl-2-phenylacetamide
17. (1α,5α,6α)-N-[3-(4-chlorophenethyl)-3-azabicyclo[3.1.0]hex-6-yl]-2-hydroxy-2-cyclopentyl-2-phenylacetamide
18. (1α,5α,6α)-N-[3-(4-nitrobenzyl)-3-azabicyclo[3.1.0]hex-6-yl]-2-hydroxy-2-cyclopentyl-2-phenylacetamide
19. (1α,5α,6α)-N-[3-(4-phenylpropyl)-3-azabicyclo[3.1.0]hex-6-yl]-2-hydroxy-2-cyclopentyl-2-phenylacetamide
20. (1α,5α,6α)-N-[3-(3-hydroxybenzyl)-3-azabicyclo[3.1.0]hex-6-yl]-2-hydroxy-2-cyclopentyl-2-phenylacetamide
21. (1α,5α,6α)-N-[3-(3-hydroxybenzyl)-3-azabicyclo[3.1.0]hex-6-yl]-2-hydroxy-2-cyclopentyl-2-phenylacetamide
22. (1α,5α,6α)-N-[3-(4-t-butylbenzyl)-3-azabicyclo[3.1.0]hex-6-yl]-2-hydroxy-2-hydroxy-2-cyclopentyl-2-phenylacetamide
23. (1α,5α,6α)-N-[3-(2-methylquinolinyl)-3-azabicyclo[3.1.0]hex-6-yl]-2-hydroxy-2-cyclopentyl-2-phenylacetamide
24. (1α,5α,6α)-N-[3-(3-nitro-4-methoxybenzyl)-3-azabicyclo[3.1.0]hex-6-yl]-2-hydroxy-2-cyclopentyl-2-phenylacetamide
25. (1α,5α,6α)-N-[3-(3-nitro-4-hydroxybenzyl)-3-azabicyclo[3.1.0]hex-6-yl]-2-hydroxy 2-cyclopentyl-2-phenylacetamide
26. (1α,5α,6α)-N-[3-(3,4-dichlorophenyl)-3-azabicyclo[3.1.0]hex-6-yl]-2-hydroxy-2-cyclopentyl-2-phenylacetamide
27. (1α,5α,6α)-N-[3-(3-aminobenzyl)-3-azabicyclo[3.1.0]hex-6-yl]-2-hydroxy-2-cyclopentyl-2-phenylacetamide 28. (1α,5α,6α)-N-[3-(6-aminopyridin-2-yl-methyl)-3-azabicyclo[3.1.0]hex-6-yl]-2-hydroxy-2-cyclopentyl-2-phenylacetamide
29. (1α,5α,6α)-N-[3-(2-phenoxyethyl)-3-azabicyclo[3.1.0]hex-6-yl]-2-hydroxy-2-cyclopentyl-2-phenylacetamide
30. (1α,5α,6α)-N-[3-(3-phenoxypropyl)-3-azabicyclo[3.1.0]hex-6-yl]-2-hydroxy-2-cyclopentyl-2-phenylacetamide
31. (1α,5α,6α)-N-[3-(2-methylpyrollyl)-3-azabicyclo[3.1.0]hex-6-yl]-2-hydroxy-2-cyclopentyl-2-phenylacetamide
32. (1α,5α,6α)-N-[3-(1,4-benzodioxan-6-yl)-3-methyl-3-azabicyclo[3.1.0]hex-6-yl]-2-hydroxy-2-cyclopentyl-2-phenylacetamide
33. (1α,5α,6α)-N-[3-benzyl-3-azabicyclo[3.1.0]hex-6-yl]-2-hydroxy-2-cyclopentyl-2-phenylacetamide
34. (1α,5α,6α)-N-[3-(4-methyl-3-pentyl)-3-azabicyclo-[3.1.0]hex-6-yl]-2-hydroxy-2-cyclopentyl-2-phenylacetamide
35. (1α,5α,6α)-N-[3-(2-(3,4-methylendioxyphenyl)ethyl]-3-azabicyclo-[3.1.0]hex-6-yl]-2-hydroxy-2-cyclobutyl-2-phenylacetamide
36. (1α,5α,6α)-N-[3-benzyl-3-azabicyclo-[3.1.0]hex-6-yl]-2-hydroxy-2-cyclopentyl-2-phenylacetamide
37. (1α,5α,6α)-N-[3-(4-methyl-3-pentenyl)-3-azabicyclo-[3.1.0]hex-6-yl]-2-hydroxy-2-cyclopropyl-2-phenylacetamide
38. (1α,5α,6α)-N-[3-[2-(3,4-methylenedioxyphenyl)ethyl]-3-azabicyclo-[3.1.0]hex-6-yl]-2-hydroxy-2-cyclopropyl-2-phenylacetamide
39. (1α,5α,6α)-N-[3-(4-hydroxy-3-methoxybenzyl)-3-azabicyclo-[3.1.0]hex-6-yl]-2-hydroxy-2-cyclopropyl-2-phenylacetamide
40. (1α,5α,6α)-N-[3-(3-hydroxy-4-methoxybenzyl]-3-azabicyclo-[3.1.0]hex-6-yl]-2-hydroxy-2-cyclopentyl-2-phenylacetamide
41. (1α,5α,6α)-N-[3-(2-phenylcarboethoxyethyl]-3-azabicyclo[3.1.0]hex-6-yl]-2-hydroxy-2-cyclopentyl-2-phenylacetamide
42. (1α,5α,6α)-N-[3-(1-(2-hydroxyphenyl)ethyl]-3-azabicyclo[3.1.0]hex-6-yl]-2-hydroxy-2-cyclopentyl-2-phenylacetamide
43. (1α,5α,6α)-N-[3-(1-(4-methylphenyl)ethyl]-3-azabicyclo[3.1.0]hex-6-yl]-2-hydroxy-2-cyclopentyl-2-phenylacetamide
44. (1α,5α,6α)-N-[3-(1-bromophenylmethylpyridine)-3-azabicyclo-[3.1.0]hex-6-yl]-2-hydroxy-2-cyclopentyl-2-phenylacetamide
45. (1α,5α,6α)-N-[3-(4-pyridylmethyl)-3-azabicyclo[3.1.0]hex-6-yl]-2-hydroxy-2-cyclopentyl-2-phenylacetamide
46. (1α, 5α6α)-N-[3-(1-indanyl)-3-azabicyclo[3.1.0]hex-6-yl]-2-hydroxy-2-cyclopentyl-2-phenylacetamide
47. (1α,5α,6α)-N-[3-(3-methylbenzyl)-3-azabicyclo[3.1.0]hex-6-yl]-2-hydroxy-2-cyclopentyl-2-phenylacetamide
48. (1α,5α,6α)-N-[3-(2,4,6-trimethylbenzyl)-3-azabicyclo[3.1.0]hex-6-yl]-2-hydroxy-2-cyclopentyl-2-phenylacetamide
49. (1α,5α,6α)-N-[3-(2-(3,4-dimethoxyphenyl)-3-azabicyclo[3.1.0]hex-6-yl]-2-hydroxy-2-cyclopentyl-2-phenylacetamide
50. (1α,5α,6α)-N-[3-(2-(3,4-dimethylphenyl)ethyl-3-azabicyclo[3.1.0]hex-6-yl]-2-hydroxy-2-cyclopentyl-2-phenylacetamide
51. (1α,5α,6α)-N-[3-pentyl-3-azabicyclo[3.1.0]hex-6-yl]-2-hydroxy-2-cyclopentyl-2-phenylacetamide
52. (1α,5α,6α)-N-[3-(4-cyanobenzyl)-3-azabicyclo[3.1.0]hex-6-yl]-2-hydroxy-2-cyclopentyl-2-phenylacetamide
53. (1α,5α,6α)-N-[3-(2-cyanobenzyl)-3-azabicyclo[3.1.0]hex-6-yl]-2-hydroxy-2-cyclopentyl-2-phenylacetamide
54. (1α,5α,6α)-N-[3-(2,3,4,5,6-pentafluorobenzyl)-3-azabicyclo[3.1.0]hex-6-yl]-2-hydroxy-2-cyclopentyl-2-phenylacetamide
55. (1α,5α,6α)-N-[3-(4-cyanobenzyl)-3-azabicyclo-[3.1.0]hex-6-yl]-2-hydroxy-2-cyclohexyl-2-phenylacetamide
56. (1α,5α,6α)-N-[3-(3-methylpyridyl)-3-azabicyclocyanobenzyl[3.1.0]hex-6-yl]-2-hydroxy-2-cyclopentyl-2-phenylacetamide
57. (1α,5α,6α)-N-[3-(4-bromo-2-methylthienyl)-3-azabicyclo[3.1.0]hex-6-yl]-2-hydroxy-2-cyclohexyl-2-phenylacetamide
58. (1α,5α,6α)-N-[3-(1-(phenyl)ethyl]-3-azabicyclo[3.1.0]hex-6-yl]-2-hydroxy-2-cyclohexyl-2-phenylacetamide
59. (1α,5α,6α)-N-[3-(2-nitrobenzyl)-3-azabicyclo[3.1.0]hex-6-yl]-2-hydroxy-2-cyclopentyl-2-phenylacetamide
60. (1α,5α,6α)-N-[3-(4-methoxycarbonyl]benzyl]-3-azabicyclo[3.1.0]hex-6-yl]-2-hydroxy-2-cyclopentyl-2-phenylacetamide
61. (1α,5α,6α)-N-[3-(diphenylmethyl)-3-azabicyclo[3.1.0]hex-6-yl]-2-hydroxy-2-cyclopentyl-2-phenylacetamide
62. (1α,5α,6α)-N-[3-(4-carboxybenzyl)-3-azabicyclo[3.1.0]hex-6-yl]-2-hydroxy-2-cyclopentyl-2-phenylacetamide
63. (1α,5α,6α)-N-[3-(2-aminobenzyl)-3-azabicyclo[3.1.0]hex-6-yl]-2-hydroxy-2-cyclopentyl-2-phenylacetamide
64. (1α,5α,6α)-N-[3-(2-carboethoxypropyl)-3-azabicyclo[3.1.0]hex-6-yl]-2-hydroxy-2-cyclopentyl-2-phenylacetamide
65. (1α,5α,6α)-N-[3-(2-(4-acetylphenyl)-3-azabicyclo[3.1.0]hex-6-yl]-2-hydroxy-2-cyclopentyl-2-phenylacetamide
66. (1α,5α,6α)-N-[3-(2-(4-methoxycarbonyl)phenyl)ethyl-3-azabicyclo[3.1.0]hex-6-yl]-2-hydroxy-2-cyclopentyl-2-phenylacetamide
67. (1α,5α,6α)-N-[3-(3-cyanobenzyl)-3-azabicyclo[3.1.0]hex-6-yl]-2-hydroxy-2-cyclopentyl-2-phenylacetamide
68. (1α,5α,6α)-N-[3-(2-cyanobenzyl)-3-azabicyclo[3.1.0]hex-6-yl]-2-hydroxy-2-cyclohexyl-2-phenylacetamide
69. (1α,5α,6α)-N-[3-(3-cyanobenzyl)-3-azabicyclo[3.1.0]hex-6-yl]-2-hydroxy-2-cyclohexyl-2-phenylacetamide
70. (1α,5α,6α)-N-[3-(3-methylbutyl)-3-azabicyclo[3.1.0]hex-6-yl]-2-hydroxy-2-cyclohexyl-2-phenylacetamide
71. (1α,5α,6α)-N-[3-(4-hydroxymethyl phenethyl)-3-azabicyclo[3.1.0]hex-6-yl]-2-hydroxy-2-cyclobentyl-2-phenylacetamide
72. (1α,5α,6α)-N-[3-(3-Fluoro-4-aminobenzyl)-3-azabicyclo[3.1.0]hex-6-yl]-2-hydroxy-2-cyclopentyl-2-phenylacetamide
73. (1α,5α,6α)-N-[3-(1-(3,4-dimethylphenyl)ethyl)-3-azabicyclo[3.1.0]hex-6-yl]-2-hydroxy-2-cyclopentyl-2-phenylacetamide
74. (1α,5α,6α)-N-[3-(2-(3-methylphenoxy)ethyl]-3-azabicyclo[3.1.0]hex-6-yl]-2-hydroxy-2-cyclopentyl-2-phenylacetamide
75. (1α,5α,6α)-N-[3-(3-(3-methylphenoxy)propyl)-3-azabicyclo[3.1.0]hex-6-yl]-2-hydroxy-2-cyclopentyl-2-phenylacetamide
76. (1α,5α,6α)-N-[3-(2-methylbenzyl)-3-azabicyclo[3.1.0]hex-6-yl]-2-hydroxy-2-cyclopentyl-2-phenylacetamide
77. (1α,5α,6α)-N-[3-(2-(2-methylbenzyl)-3-azabicyclo[3.1.0]hex-6-yl]-2-hydroxy-2-cyclopentyl-2-phenylacetamide 78. (1α,5α,6α)-N-[3-(1,3-dioxolan-2-yl-methyl)-3-azabicyclo[3.1.0]hex-6-yl]-2-hydroxy-2-cyclopentyl-2-phenylacetamide 79. (1α,5α,6α)-N-[3-(2-carboxy)propyl-3-azabicyclo[3.1.0]hex-6-yl]-2-hydroxy-2-cyclopentyl-2-phenylacetamide 80. (1α,5α,6α)-N-[3-(1-phenylethyl)-3-azabicyclo[3.1.0]hex-6-yl]-2-hydroxy-2,2-diphenylacetamide 81. (1α,5α,6α)-N-[3-(1-phenylethyl)-3-azabicyclo[3.1.0]hex-6-yl]-2-hydroxy-2-cyclopentyl-2-phenylacetamide 82. (1α,5α,6α)-N-[3-(2-(2,3-dihydrobenzofuran-5-yl)ethyl)-3-azabicyclo[3.1.0]hex-6-yl]-2-hydroxy-2-cyclopropyl-2-phenylacetamide 83. (1α,5α,6α)-N-[3-(1-phenylethyl)-3-azabicyclo[3.1.0]hex-6-yl]-2-hydroxy-2-cyclopropyl-2-phenylacetamide 84. (1α,5α,6α)-N-[3-(1-phenylethyl)-3-azabicyclo[3.1.0]hex-6-yl]-2-hydroxy-2-cyclobutyl-2-phenylacetamide 85. (1α,5α,6α)-N-[3-(2-phenylcarboxy)ethyl-3-azabicyclo[3.1.0]hex-6-yl]-2-hydroxy-2-cycloheptyl-2-phenylacetamide 86. (1α,5α,6α)-N-[3-(2-(3-indoyl)ethyl)-3-azabicyclo[3.1.0]hex-6-yl]-2-hydroxy-2-cyclohexyl-2-phenylacetamide 87. (1α,5α,6α)-N-[3-(2-methylnaphthyl)-3-azabicyclo[3.1.0]hex-6-yl]-2-hydroxy-2-cyclohexyl-2-phenylacetamide 88. (1α,5α,6α)-N-[3-(2-indoyl-3-yl)ethyl-3-azabicyclo[3.1.0]hex-6-yl]-2-hydroxy-2-cyclopentyl-2-phenylacetamide 89. (1α,5α,6α)-N-[3-hexyl-3-azabicyclo[3.1.0]hex-6-yl]-2-hydroxy-2-cyclopentyl-2-phenylacetamide 90. (1α,5α,6α)-N-[3-(1,2,3,4-tetrahydronaphth-1-yl)-3-azabicyclo[3.1.0]hex-6-yl]-2-hydroxy-2-cyclopentyl-2-phenylacetamide 91. (1α,5α,6α)-N-[3-(2-chlorobenzyl)-3-azabicyclo[3.1.0]hex-6-yl]-2-hydroxy-2-cyclopentyl-2-phenylacetamide 92. (1α,5α,6α)-N-[3-(2-(2-methoxyphenyl)ethyl)-3-azabicyclo[3.1.0]hex-6-yl]-2-hydroxy-2-cyclopentyl-2-phenylacetamide 93. (1α,5α,6α)-N-[3-(2-(4-fluorophenyl)ethyl)-3-azabicyclo[3.1.0]hex-6-yl]-2-hydroxy-2-cyclopentyl-2-phenylacetamide 94. (1α,5α,6α)-N-[3-(indan-5-yl)ethyl)-3-azabicyclo[3.1.0]hex-6-yl]-2-hydroxy-2-cyclopentyl-2-phenylacetamide 95. (1α,5α,6α)-N-[3-(1-(naphth-1-yl)ethyl)-3-azabicyclo[3.1.0]hex-6-yl]-2-hydroxy-2-cyclopentyl-2-phenylacetamide 96. (1α,5α,6α)-N-[3-(1-(3,4-methylenedioxyphenyl)ethyl)-3-azabicyclo[3.1.0]hex-6-yl]-2-hydroxy-2-cyclopentyl-2-phenylacetamide 97. (1α,5α,6α)-N-[3-(1,2,3,4-tetrahydronaphth-6-yl)ethyl)-3-azabicyclo[3.1.0]hex-6-yl]-2-hydroxy-2-cyclopentyl-2-phenylacetamide 98. (1α,5α,6α)-N-[3-(1-(cis-(hex-3-enyl)-3-azabicyclo[3.1.0]hex-6-yl]-2-hydroxy-2-cyclopropyl-2-phenylacetamide 99. (1α,5α,6α)-N-[3-(1-(trans-hex-3-enyl)-3-azabicyclo[3.1.0]hex-6-yl]-2-hydroxy-2-cyclopropyl-2-phenylacetamide 100. (1α, 5α6α)-N-[3-(1-(trans-hex-3-enyl)-3-azabicyclo[3.1.0]-2-hydroxy-2-cyclohexyl-2-phenylacetamide 101. (1α,5α,6α)-N-[3-(1-(cis-hex-3-enyl)-3-azabicyclo[3.1.0]hex-6-yl]-2-hydroxy-2-cyclohexyl-2-phenylacetamide 102. (1α,5α,6α)-N-[3-(1-(trans-hex-3-enyl)-3-azabicyclo[3.1.0]hex-6-yl]-2-hydroxy-2-cyclopentyl-2-phenylacetamide 103. (1α,5α,6α)-N-[3-(1-(cis-hex-3-enyl)-3-azabicyclo[3.1.0]hex-6-yl]-2-hydroxy-2-cyclopentyl-2-phenylacetamide 104. (1α,5α,6α)-N-[3-(2-naphthylmethyl)-3-azabicyclo[3.1.0]hex-6-yl]-2-hydroxy-2-cyclopentyl-2-phenylacetamide 105. (1α,5α,6α)-N-[3-(2-phenyl-1-methyl)-2-oxoethyl]-3-azabicyclo[3.1.0]hex-6-yl]-2-hydroxy-2-cyclopentyl-2-phenylacetamide 106. (1α,5α,6α)-N-[3-(2-(4-carbamoylphenyl)ethyl)-3-azabicyclo[3.1.0]hex-6-yl]-2-hydroxy-2-cyclopentyl-2-phenylacetamide 107. (1α,5α,6α)-N-[3-(2-(4-benzyloxycarbonylphenyl)ethyl)-3-azabicyclo[3.1.0]hex-6-yl]-2-hydroxy-2-cyclopentyl-2-phenylacetamide 108. (1α,5α,6α)-N-[3-(1-(2-methylpropyl)benzane-3-azabicyclo[3.1.0]hex-6-yl]-hydroxy-2-cyclopentyl-2-phenylacetamide 109. (1α,5α,6α)-N-[3-(2-(phenyl-1-methyl)-2-oxoethyl)-3-azabicyclo[3.1.0]hex-6-yl]-2-hydroxy-2-cyclohexyl-2-phenylacetamide 110. (1α,5α,6α)-N-[3-hexyl-3-azabicyclo[3.1.0]hex-6-yl]-2-hydroxy-2-cyclohexyl-2-phenylacetamide 111. (1α,5α,6α)-N-[3-(2-(4-cyanophenyl)ethyl)-3-azabicyclo[3.1.0]hex-6-yl]-2-hydroxy-2-cyclopentyl-2-phenylacetamide 112. (1α,5α,6α)-N-[3-(2-(4-sulphamoylphenyl)ethyl)1-3-azabicyclo[3.1.0]hex-6-yl]-2-hydroxy-2-cyclopentyl-2-phenylacetamide 113. (1α,5α,6α)-N-[3-cyclohexylmethyl-3-azabicyclo[3.1.0]hex-6-yl]-2-hydroxy-2-cyclopentyl-2-phenylacetamide 114. (1α,5α,6α)-N-[3-benzyl-3-azabicyclo[3.1.0]hex-6-yl]-2,2-diphenylacetamide 115. (1α,5α,6α)-N-[3-benzyl-3-azabicyclo[3.1.0]hex-6-yl]-2-chloro-2-cyclohexyl-2-phenylacetamide 116. (1α,5α,6α)-N-[3-benzyl-3-azabicyclo[3.1.0]hex-6-yl]-2-cyclohexyl-2-phenylacetamide 117. (1α,5α,6α)-N-[3-benzyl-3-azabicyclo[3.1.0]hex-6-yl]-2-hydroxy-2-phenylacetamide 118. (1α,5α,6α)-N-[3-benzyl-3-azabicyclo[3.1.0]hex-6-yl]-2-cyclopentyl-2-phenylacetamide 119. (1α,5α,6α)-N-[3-benzyl-3-azabicyclo[3.1.0]hex-6-yl]-2-hydroxy-2-phenyl propionamide 120. N-methyl-N-(1α,5α,6α)-N-[3-(1-phenyl-ethyl)-3-azabicyclo[3.1.0]-hex-6-yl]-2-cyclopentyl-2-hydroxy-2-phenylacetamide 121. N-methyl-N-(1α,5α,6α)-N-[3-(3,4-methylenedioxyethyl)-3-azabicyclo[3.1.0]-hex-6-yl]-2-cyclopentyl-2-hydroxy-2-phenylacetamide 122. N-methyl-N-(1α,5α,6α)-N-[3-(9-benzyl-3-azabicyclo[3.1.0]-hex-6-yl]-2-cyclopentyl-2-hydroxy-2-phenylacetamide 123. N-methyl-(1α,5α,6α)-N-[3-(3,4-methylenedioxyethyl)-3-azabicyclo[3.1.0]-hex-6-yl]-2-cyclohexyl-2-hydroxy-2-phenylacetamide 124. N-methyl-N-(1α,5α,6α)-N-[3-(4-methyl-3-pentenyl)-3-azabicyclo[3.1.0]-hex-6-yl]-2-cyclohexyl-2-hydroxy-2-phenylacetamide 125. N-methyl-N-(1α,5α,6α)-N-[3-(4-methyl-3-pentenyl)-3-azabicyclo[3.1.0]-hex-6-yl]-2-cyclopentyl-2-hydroxy-2-phenylacetamide 126. N-methyl-N-(1α,5α,6α)-N-[3-(4-methyl-3-pentenyl)-3-azabicyclo[3.1.0]-hex-6-yl]-2-cyclopentyl-2-hydroxy-2-phenylacetamide L (+)tartarate salt.

TABLE I

Formula I: Ar—C(R1)(R2)—W—C(=O)—X—Y—N(R3)—[bicyclic(CH2)m]N—R4

| Compound No. | Ar | R$_1$ | R$_2$ | R$_3$ | R$_4$ |
|---|---|---|---|---|---|
| 1 | 4-MeO-C$_6$H$_4$ | OH | cyclopentyl | H | 2-methyl-2-butenyl |
| 2 | phenyl | OH | cyclohexyl | H | 2-thienylmethyl |
| 3 | phenyl | OH | cyclopentyl | H | 2-thienylmethyl |
| 4 | phenyl | OH | cyclopentyl | H | (5-nitrofuran-2-yl)methyl |
| 5 | phenyl | OH | cyclopentyl | H | isohexyl |
| 6 | phenyl | OH | cyclopentyl | H | (2,3-dihydrobenzo[1,4]dioxin-6-yl)propyl |
| 7 | phenyl | OH | cyclopentyl | H | 3-(3,4,5-trimethoxyphenyl)propyl |
| 8 | phenyl | OH | cyclopentyl | H | 4-(benzo[1,3]dioxol-5-yl)butyl |
| 9 | phenyl | OH | cyclopentyl | H | 3,4,5-trimethoxybenzyl (ethyl linker) |
| 10 | phenyl | OH | cyclopentyl | H | 3,5-dimethoxyphenethyl |
| 11 | phenyl | OH | cyclopentyl | H | 3,4-dimethoxyphenethyl |

TABLE I-continued
Formula I
| Compound No. | Ar | R₁ | R₂ | R₃ | R₄ |
|---|---|---|---|---|---|
| 12 |  | OH | 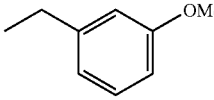 | H |  |
| 13 |  | OH | 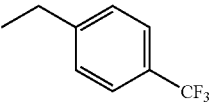 | H |  |
| 14 |  | OH | 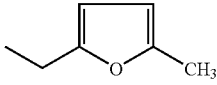 | H |  |
| 15 |  | OH | 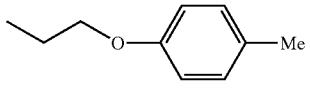 | H |  |
| 16 |  | OH | 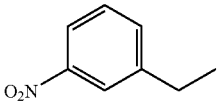 | H |  |
| 17 |  | OH | 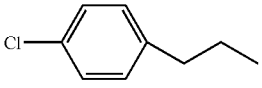 | H |  |
| 18 |  | OH | 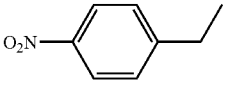 | H |  |
| 19 |  | OH | 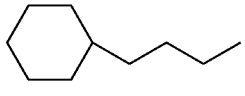 | H |  |
| 20 |  | OH | 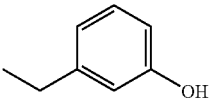 | H |  |
| 21 |  | OH | 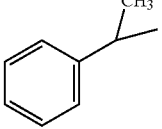 | H |  |
| 22 |  | OH | 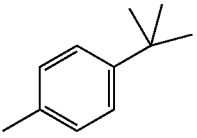 | H | |

TABLE I-continued
Formula I
| Compound No. | Ar | R₁ | R₂ | R₃ | R₄ |
|---|---|---|---|---|---|
| 23 |  | OH | 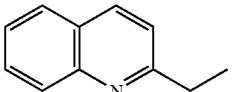 | H |  |
| 24 |  | OH | 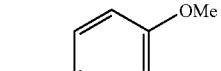 | H |  |
| 25 |  | OH | 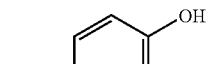 | H |  |
| 26 |  | OH | 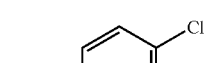 | H |  |
| 27 |  | OH | 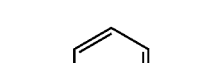 | H |  |
| 28 |  | OH | 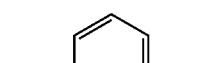 | H |  |
| 29 |  | OH | 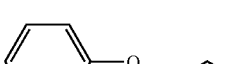 | H |  |
| 30 |  | OH | 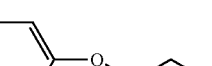 | H |  |
| 31 |  | OH |  | H |  |
| 32 |  | OH |  | H |  |
| 33 |  | OH | 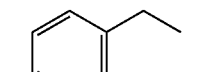 | H |  |

TABLE I-continued
Formula I
| Compound No. | Ar | R₁ | R₂ | R₃ | R₄ |
|---|---|---|---|---|---|
| 34 |  | OH |  | H | 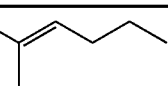 |
| 35 |  | OH |  | H | 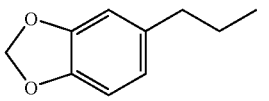 |
| 36 |  | OH |  | H | 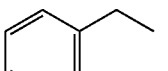 |
| 37 |  | OH |  | H | 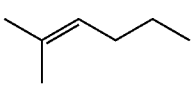 |
| 38 |  | OH |  | H | 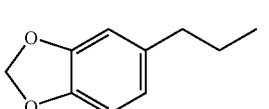 |
| 39 |  | OH | 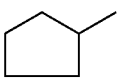 | H | 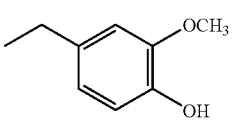 |
| 40 |  | OH | 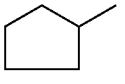 | H | 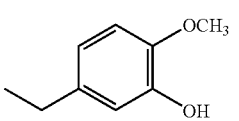 |
| 41 |  | OH | 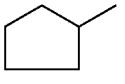 | H | 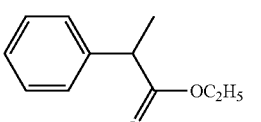 |
| 42 |  | OH | 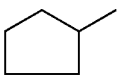 | H | 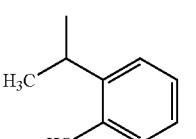 |
| 43 |  | OH | 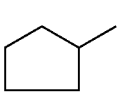 | H | 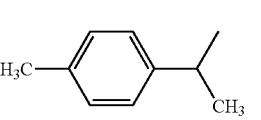 |
| 44 |  | OH | 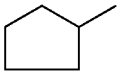 | H | 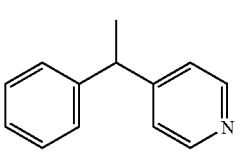 |

TABLE I-continued
Formula I
| Compound No. | Ar | R₁ | R₂ | R₃ | R₄ |
|---|---|---|---|---|---|
| 45 | 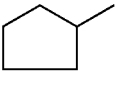 | OH | 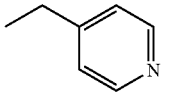 | H |  |
| 46 | 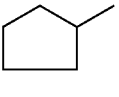 | OH | 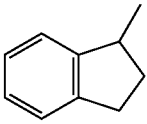 | H |  |
| 47 | 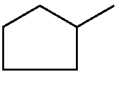 | OH | 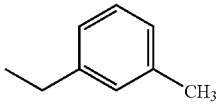 | H |  |
| 48 | 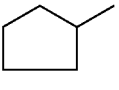 | OH | 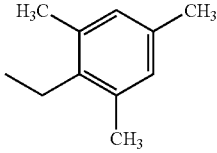 | H |  |
| 49 | 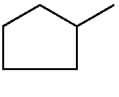 | OH | 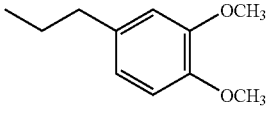 | H |  |
| 50 | 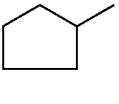 | OH | 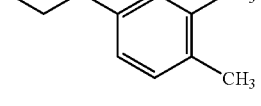 | H |  |
| 51 | 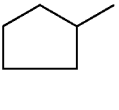 | OH |  | H |  |
| 52 | 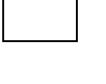 | OH | 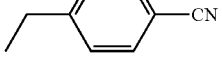 | H |  |
| 53 |  | OH | 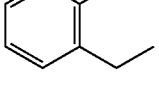 | H |  |
| 54 | 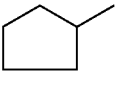 | OH | 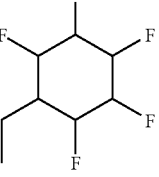 | H |  |

TABLE I-continued
Formula I
| Compound No. | Ar | R₁ | R₂ | R₃ | R₄ |
|---|---|---|---|---|---|
| 55 |  | OH | 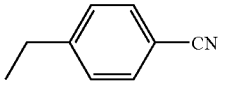 | H |  |
| 56 |  | OH | 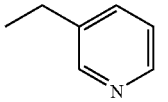 | H |  |
| 57 |  | OH | 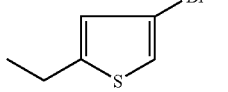 | H |  |
| 58 |  | OH | 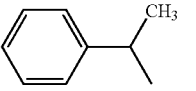 | H |  |
| 59 |  | OH | 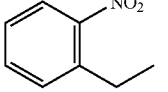 | H |  |
| 60 |  | OH | 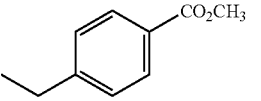 | H |  |
| 61 |  | OH | 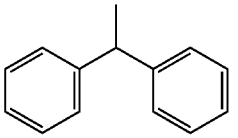 | H |  |
| 62 |  | OH | 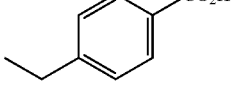 | H |  |
| 63 |  | OH | 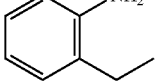 | H |  |
| 64 |  | OH | 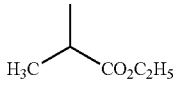 | H |  |
| 65 |  | OH | 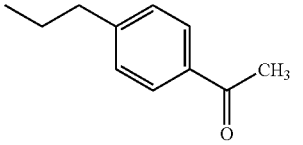 | H | 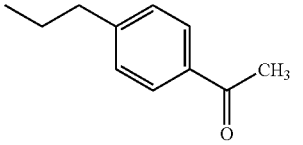 |

TABLE I-continued
Formula I
$$Ar-\underset{R_2}{\overset{R_1}{C}}-W-\underset{O}{\overset{}{C}}-X-Y-\underset{R_3}{N}-\text{(CH}_2\text{)}_m-N-R_4$$
| Compound No. | Ar | R₁ | R₂ | R₃ | R₄ |
|---|---|---|---|---|---|
| 66 |  | OH |  | H | 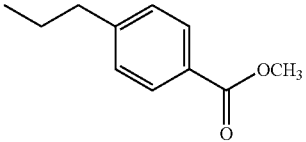 |
| 67 |  | OH |  | H | 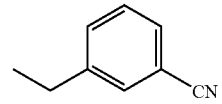 |
| 68 |  | OH |  | H | 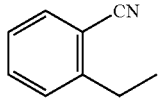 |
| 69 |  | OH |  | H | 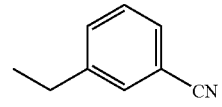 |
| 70 |  | OH |  | H |  |
| 71 |  | OH |  | H | 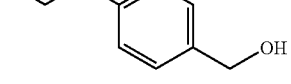 |
| 72 |  | OH |  | H | 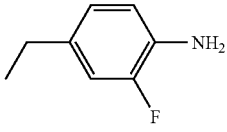 |
| 73 |  | OH |  | H | 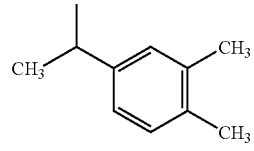 |
| 74 |  | OH |  | H | 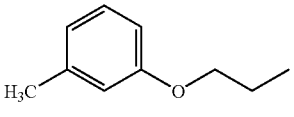 |
| 75 |  | OH |  | H | 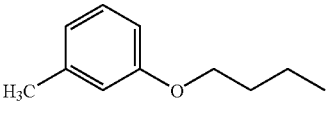 |
| 76 |  | OH |  | H | 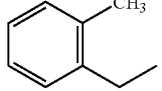 |

TABLE I-continued

Formula I

| Compound No. | Ar | R₁ | R₂ | R₃ | R₄ |
|---|---|---|---|---|---|
| 77 | phenyl | OH | cyclopentyl | H | 2-methylphenyl-propyl |
| 78 | phenyl | OH | cyclopentyl | H | 2-ethyl-1,3-dioxolane |
| 79 | phenyl | OH | cyclopentyl | H | (CH₃)₂CHCO₂H |
| 80 | phenyl | OH | phenyl | H | phenyl-isopropyl |
| 81 | phenyl | OH | methylcyclooctyl | H | phenyl-isopropyl |
| 82 | phenyl | OH | cyclopropyl | H | 5-propyl-2,3-dihydrobenzofuran |
| 83 | phenyl | OH | cyclopropyl | H | phenyl-isopropyl |
| 84 | phenyl | OH | methylcyclobutyl | H | phenyl-isopropyl |
| 85 | phenyl | OH | methylcyclopentyl | H | phenyl-CH(CH₃)COOH |
| 86 | phenyl | OH | cyclohexyl | H | 3-propyl-indole |
| 87 | phenyl | OH | cyclohexyl | H | 2-ethylnaphthalene |
| 88 | phenyl | OH | cyclopentyl | H | 3-propyl-indole |

TABLE I-continued
Formula I
| Compound No. | Ar | R₁ | R₂ | R₃ | R₄ |
|---|---|---|---|---|---|
| 89 | 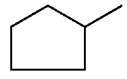 | OH | 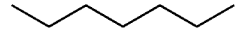 | H |  |
| 90 | 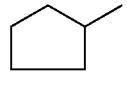 | OH | 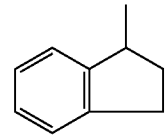 | H |  |
| 91 | 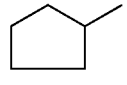 | OH | 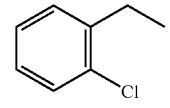 | H |  |
| 92 | 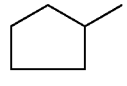 | OH | 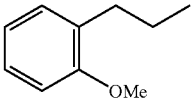 | H |  |
| 93 | 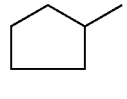 | OH | 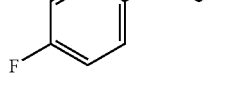 | H |  |
| 94 | 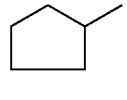 | OH | 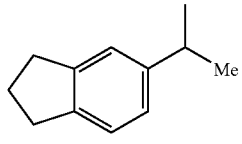 | H |  |
| 95 | 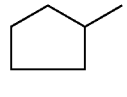 | OH | 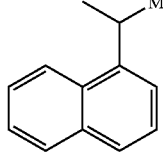 | H |  |
| 96 | 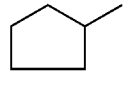 | OH | 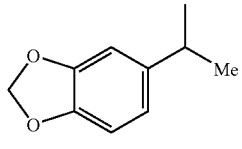 | H |  |
| 97 | 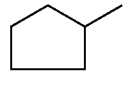 | OH | 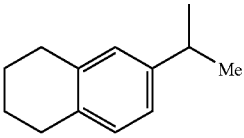 | H |  |
| 98 | 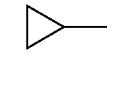 | OH | 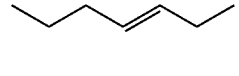 | H | |

TABLE I-continued
Formula I
| Compound No. | Ar | R₁ | R₂ | R₃ | R₄ |
|---|---|---|---|---|---|
| 99 |  | OH | 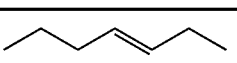 | H |  |
| 100 | 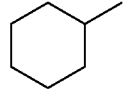 | OH | 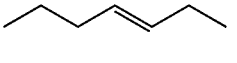 | H |  |
| 101 | 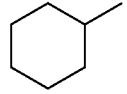 | OH | 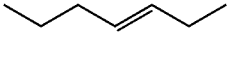 | H |  |
| 102 | 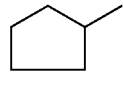 | OH | 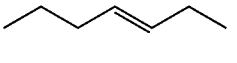 | H |  |
| 103 | 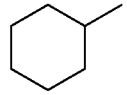 | OH | 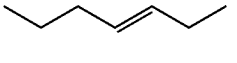 | H |  |
| 104 | 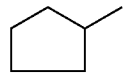 | OH | 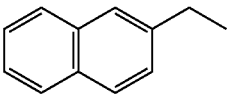 | H |  |
| 105 | 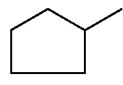 | OH | 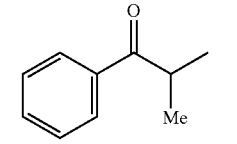 | H |  |
| 106 | 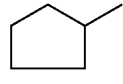 | OH | 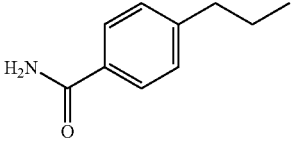 | H |  |
| 107 | 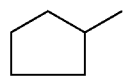 | OH | 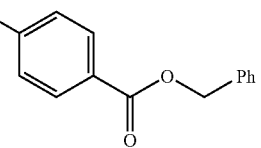 | H |  |
| 108 | 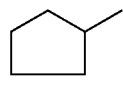 | OH | 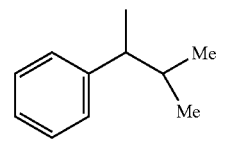 | H |  |

TABLE I-continued

Formula I

Ar—C(R1)(R2)—W—C(=O)—X—Y—N(R3)—[bicyclic (CH2)m]—N—R4

| Compound No. | Ar | R1 | R2 | R3 | R4 |
|---|---|---|---|---|---|
| 109 | phenyl | OH | cyclohexyl | H |  |
| 110 | phenyl | OH | cyclohexyl | H | n-hexyl |
| 111 | phenyl | OH | cyclopentyl | H |  |
| 112 | phenyl | OH | cyclopentyl | H | 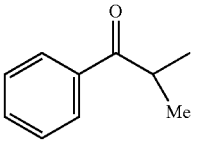 |
| 113 | phenyl | OH | cyclopentyl | H | cyclohexylethyl |
| 114 | phenyl | H | phenyl | H | phenethyl |
| 115 | phenyl | Cl | cyclohexyl | H | phenethyl |
| 116 | phenyl | H | cyclohexyl | H | phenethyl |
| 117 | phenyl | OH | H | H | phenethyl |
| 118 | phenyl | H | cyclopentyl | H | phenethyl |
| 119 | phenyl | OH | CH3 | H | phenethyl |
| 120 | phenyl | OH | cyclopentyl | CH3 |  |

TABLE I-continued

Formula I

| Compound No. | Ar | $R_1$ | $R_2$ | $R_3$ | $R_4$ |
|---|---|---|---|---|---|
| 121 |  | OH | 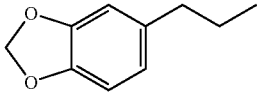 | $CH_3$ |  |
| 122 |  | OH | 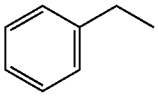 | $CH_3$ |  |
| 123 | 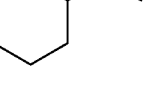 | OH | 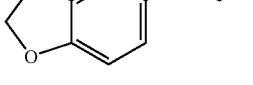 | $CH_3$ |  |
| 124 | 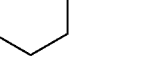 | OH |  | $CH_3$ |  |
| 125 |  | OH |  | $CH_3$ |  |
| 126 |  | OH | 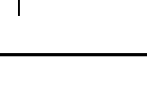 | $CH_3$ | |

(wherein, W is $(CH_2)p$ where p = 0, X is no atom and Y is $(CH_2)q$ where q = 0, m = 0)

Compounds or compositions disclosed may be administered to an animal for treatment orally, or by parenteral route. Pharmaceutical compositions disclosed herein can be produced and administered in dosage units, each unit containing a certain amount of at least one compound described herein and/or at least one physiologically acceptable salt addition thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes within its scope prodrugs of the compounds of Formulae I, II, III, I, V and VI. In general, such prodrugs will be functional derivatives of these compounds, which readily are converted in vivo into the defined compounds. Conventional procedures for the selection and preparation of suitable prodrugs are known.

The present invention also includes the enantiomers, diastereomers, N-Oxides, polymorphs, solvates and pharmaceutically acceptable salts of these compounds as well as metabolites having the same type of activity. The present invention further includes pharmaceutical composition comprising the molecules of Formulae I, II, III, IV, V and VI or prodrugs, metabolite enantiomers, diastereomers. N-oxides, polymorphs solvates or pharmaceutically acceptable salts thereof, in combination with pharmaceutically acceptable carrier and optionally included excipient.

The examples mentioned below demonstrate the general synthetic procedure as well as the specific preparation of the preferred compound. The examples are provided to illustrate particular aspects of the disclosure and should not be constrained to limit the scope of the present invention, as defined by the claims.

Experimental Details

Various solvents, such as acetone, methanol, pyridine, ether, tetrahydrofuran, hexanes, and dichloromethane, were dried using various drying reagents according to procedures well known in the literature. IR spectra were recorded as nujol mulls or a thin neat film on a Perkin Elmer Paragon instrument, Nuclear Magnetic Resonance (NMR) were recorded on a Varian XL-300 MHz instrument using tetramethylsilane as an internal standard.

EXAMPLE 1
Preparation of (1α, 5α, 6α)-N-[3-(4-methyl-3-pentenyl)-3-azabicyclo[3.1.0]hex-6-yl]-2-hydroxy-2-cyclopentyl-2-(4-methoxy)phenyl acetamide (Compound No.1)

Step-1a: Synthesis of
2-Hydroxy-2-cyclopentyl-2-(4-methoxy)phenylacetic acid

This was prepared following the procedure described in J. Amer. Chem. Soc. 75, 2654 (1953).

Step-1b: Synthesis of (1α, 5α, 6α)-6-amino-3-azabicyclo[3.1.0]hexane:

This was synthesized as per reported procedure of Braish, T. F. et. al., Synlett. 1100 (1996).

Step-1c: Synthesis of (1α, 5α, 6α)-6-tert-butoxy carbonylamino-3-azabicyclo[3.1.0]hexane.

This was synthesized as per reported procedure of Braish, T. F. et. al., Synlett. 1110 (1996).

Step-1d: Synthesis (1α, 5α, 6α)-N-3-(4-methyl-3-pentenyl-6-tert butoxycarbonylamino-3-azabicyclo [3.1.0]hexane.

To a solution of compound of step-1c (1 mmol) in 10 ml of acetonitrile was added 5-bromo-4-methyl pent-3-ene (0.75 mmol) followed by the addition of potassium carbonate (3 mmol) and potassium iodide (2 mmol). The reaction mixture was refluxed for 5 hours and then brought to room temperature and filtered. The filtrate was concentrated under reduced pressure and the residue was purified by column chromatography (60×20 mesh size silica gel). The compound was eluted with 1:1 EtOAc:Hexane mixture.

$^1$HNMR (CDCl$_3$): δ value: 5.09-5.04 (t, 4H), 4.56 (bs, 1H), 3.11-3.08 (d, 2H), 2.76 (s, 1H), 2.36-2.31 (m, 4H), 2.11-2.03 (m, 2H), 1.67 (s, 3H), 1.52-1.43 (m, 13H) IR (DCM): 1706 cm$^{-1}$

Step-1e: Synthesis of (1α, 5α, 6α)-3-N-(4-methyl-3-pentenyl)-6-amino-3-azabicyclo[3.1.0]hexane hydrochloride To a solution of compound of step-1d in EtOAc (20 ml) at 0° C. was added saturated solution of hydrochloric acid in EtOAc. The reaction mixture was stirred at room temperature for 16 hours and then concentrated under reduced pressure to give a solid.

m.p.: 231° C.

Step-1f: Synthesis of (1α, 5α, 6α)-N-[3-(4-methyl-3-pentenyl)-3-azabicyclo[3.1.0]hex-6-yl]-2-hydroxy-2-cyclopentyl-2-(4-methoxy)phenyl acetamide (Compound No.1)

A solution of 2-hydroxy-2-cyclopentyl-2-(4-methoxy) phenylacetic acid (1 mmol) and (1α, 5α, 6α)-3-N-(4-methyl-3-pentenyl)-6-amino-3-azabicyclo[3.1.0]hexane hydrochloride (1 mmol) in DMF (5 ml) was cooled to 0° C. The reaction mixture was treated with 1-hydroxybenzotriazole (HOBT, 1.1 mmol) and N-methyl morpholine (NMM, 4mmol) and stirred at 0° C. for half an hr. EDC.HCl (1-[3-(dimethylamino)propyl]-3-ethyl-carbodiimide hydrochloride; 1 mmol) was added and the reaction mixture was stirred at 0° C. for 1 hr. and then at room temperature overnight. The reaction mixture was poured into saturated sodium bicarbonate solution and extracted with EtOAc. The organic layer was washed with water, dried over sodium sulphate and concentrated under reduced pressure. The residue was purified by column chromatography (100×200 mesh size silicagel) eluting the compound with 70:30 EtOAc-hexane mixture.

$^1$HNMR (CDCl$_3$, δ-value): 7.54-6.84 (m, 4-Ar—H); 6.35 (bs, 1H) 5.04 (t, 1H); 3.79 (s, 3H); 3.19-1.17 (m, 26H) IR (DCM): 1652 cm$^{-1}$

EXAMPLE 2

Preparation of (1α, 5α, 6α)-N-[3-(2-Thienylmethyl)-3-azabicyclo[3.1.0]hex-6-yl]-2-hydroxy-2-cyclohexyl-2-phenylacetamide (Compound No.2)

Step-2a: Synthesis of 2-hydroxy-2-cyclohexyl-2-phenylacetic acid

This was prepared by following the procedure in J. Amer. Chem. Soc., 75, 2654 (1953).

Step-2b: Synthesis of (1α, 5α, 6α)-N-[3-benzyl-3-azabicyclo[3.1.0]-hex-6-yl]-2-hydroxy-2-cyclohexyl-2-phenylacetamide The compound was synthesized by procedure of Example 1, step-f, using 2-hydroxy-2-cyclohexyl-2-phenylacetic acid in place of 2-hydroxy-2-cyclopentyl-2-(4-methoxy)phenylacetic acid and (1α, 5α, 6α)-3-benzyl-3-azabicyclo-6-amino [3.1.0]hexane instead of (1α, 5α, 6α)-3-N-(4-methyl-3-pentenyl)-6-amino-3-azabicyclo[3.1.0]hexane hydrochloride.

Step-2c: Synthesis of (1α, 5α, 6α)-N-[3-azabicyclo [3.1.0]-hex-6-yl]-2-cyclohexyl-2-hydroxy-2-phenylacetamide The compound of Step-b (1 mmol) in MeOH (20 ml) was added to a suspension of Pd—C in MeOH (10 ml) and the reaction mixture was hydrogenated in parr apparatus at 45 psi for 3 hrs. The reaction mixture was filtered over celite and concentrated under reduced pressure to give the compound.

$^1$HNMR (CDCl$_3$-δ value): 7.47-6.74 (m, 5ArH), 3.24-3.16 (m, 3H), 3.07-3.02 (m, 2H), 2.9-1.23 (m, 13H). IR (DCM): 1660 cm$^{-1}$

Step-2d: Synthesis of (1α, 5α, 6α)-N-[3-(2-Thienylmethyl)-3-azabicyclo[3.1.0]hex-6-yl]-2-hydroxy-2-cyclohexyl-2-phenylacetamide (Compound No.2)

A solution of compound of step c (1 mmol) and 2-formylthiophene (1.1 mmol) in dry THF was stirred over molecular sieves for 2 hours and then sodium triacetoxy borohydride was added and the reaction mixture stirred at room temperature overnight. The reaction mixture was filtered, concentrated under reduced pressure and EtOAc was added. The organic layer was washed with water, dried and concentrated under reduced pressure. The residue was purified by column chromatography (100-200 mesh, silica gel), eluting the compound with 40:60 EtOAc-hexane.

m.pt.: 153-154° C. 1HNMR (CDCl$_3$, δ value): 7.59-6.81 (m, 8 ArH), 6.59 (bs, 1H); 3.73 (s, 2H), 3.12-1.23 (m, 18H). IR (KBr): 1656 cm$^{-1}$

EXAMPLE 3

Preparation of (1α, 5α, 6α)-N-[3-(2-thienylmethyl)-3-azabicyclo[3.1.0]hex-6-yl]-2-hydroxy-2-cyclopentyl-2-phenylacetamide (Compound No.3)

Step-3a: Synthesis of 2-hydroxy-2-cylopentyl-2-phenyl acetic acid

This was prepared by following the procedure in J. Amer. Chem. Soc. 75, 2654 (1953).

Step-3b: Synthesis of (1α, 5α, 6α)-N-[3-benzyl-3-azabicyclo[3.1.0]-hex-6-yl]-2-hydroxy-2-cyclopentyl-2-phenylacetamide This was synthesized by procedure of Example 2, Step b, using 2-hydroxy-2-cyclopentyl-2-phenylacetic acid in place of 2-hydroxy-2-cyclopentyl-2-(4-(methoxy)phenylacetic acid and (1α, 5α, 6α)-3-benzyl-3-azabicyclo-6-amino[3.1.0]hexane instead of (1α, 5α, 6α)-3-N-(4-methyl-3-pentyl)-6-amino-3-azabicyclo[3.1.0]hexane hydrochloride.

Step-3c: Synthesis of (1α, 5α, 6α)-N-[3-azabicyclo-[3.10]hex-6-yl]-2-cyclopentyl-2-hydroxy-2-phenylacetmide The compound was synthesized by following the procedure of Example-2, Step-c, but using the compound (1α, 5α, 6α)-N-[3-benzyl-3-azabicyclo[3.1.0]hex-6-yl]-2-hydroxy-2-cyclopentyl-2-phenylacetamide.

Step-3d: Synthesis of (1α, 5α, 6α)-N-[3-(2-thienylmethyl)-3-azabicyclo[3.1.0]hex-6-yl]-2-hydroxy-2-cyclopentyl-2-phenylacetamide (Compound No.3)

The compound was synthesized by following the procedure of Example-2, Step-d, using (1α, 5α, 6α)-N-[3-azabicyclo-[3.1.0]-hex-6-yl]-2-hydroxy-2-cyclopentyl-2-phenylacetamide instead of (1α, 5α, 6α)-N-[3-azabicyclo-[3.1.0]-hex-6-yl]-2-hydroxy-2-cyclohexyl-2-phenylacetamide.

$^1$HNMR (CDCl$_3$-δ values): 7.58-6.82 (m, 8ArH), 6.36 (bs, 1H), 3.74 (s, 2H), 3.11-3.10 (m, 16H) IR (DCM): 1658 cm$^{-1}$

EXAMPLE 4

Preparation of (1α, 5α, 6α)-N-[3-(5-nitro-2-furylmethyl)-3-azabicyclo[3.1.0]hex-6-yl]-2-hydroxy- A solution of (1α, 5α, 6α)-N-[3-azabicyclo[3.1.0]-hex-6-yl]-2-hydroxy-2-cyclopentyl-2-phenylacetamide (1 mmol) in TBF containing acetic acid (3.7 mmol); 5-nitrofurfural (2.5 mmol) and sodium triacetoxyborohydride (3.2 mmol) was stirred at room temperature overnight. The reaction mixture was poured into saturated bicarbonate solution and extracted with EtOAc. The organic layer was washed with water and dried. The crude compound obtained after removing the solvents was purified by column chromatography (100-200 mesh silica gel) eluting the compound with 20:80 EtOAc:Hexane mixture.

$^1$HNMR (CDCl$_3$ δ-value): 7.58-7.23 (m, 5ArH), 6.44 (bs, 1H); 6.37 (d, 1H), 3.66 (s, 2H), 3.14-2.90 (m, 5H), 2.52-2.48 (m, 2H), 1.60-1.47 (m, 8H), 1.46-1.42 (m, 2H) IR (DCM): 1655 cm$^{-1}$

EXAMPLE 5

Preparation of (1α, 5α, 6α)-N-[3-(4-methyl-pentyl)-3-azabicyclo[3.1.0]-hex-6-yl]-2-hydroxy-2-cyclopentyl-2-phenylacetamide (Compound No.5)

A solution of (1α, 5α, 6α)-N-3-azabicyclo[3.1.0]-hex-6-yl]-2-hydroxy-2-phenylacetamide (1 mmol) in 15 ml of acetonitrile containing 4-methylpentyl methanesulphonate (2 mmol) and potassium carbonate (2 mmol) was refluxed for 8 hours. The reaction mixture was filtered and concentrated under reduced pressure. The residue was purified by column chromatography (100-200 mesh, silicagel) eluting the compound with 80:20:EtOAc-hexane mixture.

1HNMR (CDCl$_3$, δ value): 7.63-7.26 (m, 5ArH); 6.37 (bs, 1H), 3.14-3.07 (m, 4H); 2.85 (s, 1H); 2.33-2.28 (m, 3H), 1.7-0.82 (m, 21H) IR (DCM): 1651 cm$^{-1}$

EXAMPLE 6

Preparation of (1α, 5α, 6α)-N-[3-(2-(1,4-benzodioxan-6-yl)ethyl)-3-azabicyclo[3.1.0]-hex-6-yl]-2-hydroxy-2-cyclopentyl-2-phenylacetamide (Compound No.6)

Step-6a: Synthesis of 6-(2-bromoethyl)-1,4-benzodioxan

The compound was synthesized following the procedure of EP 0388054 A1.

Step-6b: Synthesis of (1α, 5α, 6α)-N-[3-(2-(1,4-benzodioxan-6-yl)ethyl)-3-azabicyclo[3.1.0]-hex-6-yl]-2-hydroxy-2-cyclopentyl-2-phenylacetamide The compound was synthesized following the procedure of Example-5 using 6-(2-bromoethyl)-1,4-benzodioxan, instead of 4-methylpentyl methane sulphonate.

$^1$HNMR (CDCl$_3$, δ values): 7.60-7.23 (m, 5ArH), 6.76-6.56 (m, 3H), 5.30 (s, 1H), 4.22 (s, 4H), 3.24-2.57 (m, 10H), 1.67-0.89 (m, 10H) IR (DCM): 1661 cm$^{-1}$

EXAMPLE 7

Preparation of (1α, 5α, 6α)-N-[3-(3,4,5-trimethoxyphenethyl)-3-azabicyclo[3.1.0]-hex-6-yl]-2-hydroxy-2-cyclopentyl-2-phenylacetamide (Compound No.7)

Step-7a: Synthesis of 3,4,5-trimethoxyphenethylbromide

The compound was synthesized following the procedure described in EP 0388054 A1 and starting with 3,4,5-trimethoxyphenylacetic acid.

Step-7b: Synthesis of (1α, 5α, 6α)-N-[3-(3,4,5-trimethoxyphenethyl)-3-azabicyclo[3.1.0]-hex-6-yl]-2-hydroxy-2-cyclopentyl-2-phenylacetamide The compound was synthesized following the procedure of Example 5, using 3,4,5-trimethoxyphenethyl bromide instead of 4-methylpentyl methane sulphonate.

$^1$HNMR (CDCl$_3$): 7.59-6.42 (m, 7ArH), 6.37 (bs, 1H), 3.82 (s, 9H), 3.19-0.89 (m, 20H). IR (DCM): 1653 cm$^{-1}$

EXAMPLE 8

Preparation of (1α, 5α, 6α)-N-[3-[3-(3,4-methylenedioxyphenyl)propyl)]-3-azabicyclo[3.1.0]-hex-6-yl]-2-hydroxy-2-cyclopentyl-2-phenylacetamide (Compound No.8)

The compound was synthesized by following the procedure of Example 5, using 3-(3,4-methylenedioxyphenyl)propylbromide instead of 4-methylpentyl methane sulphonate.

1HNMR (CDCl$_3$): 7.59-6.56 (m, 8ArH), 5.29 (s, 2H), 3.19-0.89 (m, 22H) IR (DCM): 1654 cm$^{-1}$

EXAMPLE 9

Preparation of (1α, 5α, 6α)-N-[3-(3,4,5-trimethoxy-benzyl)-3-azabicyclo[3.1.0] hex-6-yl]-2-hydroxy-2-cyclopentyl-2-phenylacetamide (Compound No.9)

Step-9a: Synthesis of 3,4,5-trimethoxybenzylchloride

The compound was synthesized following the procedure described in EP0388054 A1 and starting with 3,4,5-trimethoxybenzoic acid.

Step-9b: Synthesis of (1α, 5α, 6α)-N-[3-(3,4,5-trimethoxybenzyl)-3-azabicyclo[3.1.0]hex-6-yl]-2-hydroxy-2-cyclopentyl-2-phenylacetamide The compound was prepared by following the procedure of Example-5, using 3,4,5-trimethoxybenzylchloride instead of 4-methylpentyl methanesulphonate.

$^1$HNMR (CDCl$_3$, δ-values): 7.59-6.46 (m, 7ArH), 6.40 (bs, 1H), 3.82 (s, 9H), 3.46 (s, 2H), 3.09-1.01 (m, 16H) IR (DCM): 1653 cm$^{-1}$

EXAMPLE 10

Preparation of (1α, 5α, 6α)-N-[3-(3,5-dimethoxy-benzyl)-3-azabicyclo[3.1.0]-hex-6-yl]-2-hydroxy-2-cyclopentyl-2-phenylacetamide (Compound No.10)

To a solution of (1α, 5α6α)-N-[3-azabicyclo[3.1.0]hex-6-yl]-2-cyclopentyl-2-hydroxy-2-phenylacetamide (1 mmol), 3,5-dimethoxybenzylchloride (1.3 mmol), potassium carbonate (2 mmol) and potassium iodide (2 mmol) in acetonitrile was refluxed for 8 hours. The reaction mixture was filtered, concentrated under reduced pressure and the residue was purified by column chromatography (100-200 mesh size silicagel) eluting the compound with 1:1 EtOAc-hexane mixture.

$^1$HNMR (CDCl$_3$, δ values): 7.58-6.44 (m, 8ArH), 6.33 (bs, 1H), 3.76 (s, 6H), 3.52 (s, 2H), 3.11-3.10 (m, 16H)

EXAMPLE 11

Preparation of (1α, 5α, 6α)-N-[3-(3,4-dimethoxy-benzyl)-3-azabicyclo[3.1.0]hex-6-yl]-2-hydroxy-2-cyclopentyl-2-phenylacetamide (Compound No.11)

The compound was synthesized by following the procedure of Example 10 but using 3,4-dimethoxybenzylchloride instead of 3,5-dimethoxybenzylchloride.

$^1$HNMR (CDCl$_3$, δ-values): 7.58-6.74 (m, 8ArH), 6.42 (bs, 1H), 3.84 (s, 2H), 3.49-0.89 (m, 16H) IR (DCM): 1657 cm$^{-1}$

EXAMPLE 12

Preparation of (1α, 5α, 6α)-[3-(3-methoxybenzyl)-3-azabicyclo[3.1.0]hex-6-yl]-2-hydroxy-2-cyclopentyl-2-phenylacetamide (Compound No.12)

The compound was synthesized following the procedure of Example 10, using 3-methoxybenzylchloride instead of 3,5-dimethoxybenzylchloride.

The pure product was eluted with 20:80 EtOAc-hexane mixture.

$^1$HNMR (CDCl$_3$, δ values): 7.60-6.76 (m, 9Ar—H), 6.44 (bs, 1H), 3.78 (s, 3H), 3.57 (s, 2H), 3.13-0.89 (m, 16H) IR (DCM): 1661 cm$^{-1}$

EXAMPLE 13

Preparation of (1α, 5α, 6α)-N-[3-(4-trifluoromethyl-benzyl)-3-azabicyclo[3.1.0]hex-6-yl]-2-hydroxy-2-cyclopentyl 2-phenyl acetamide (Compound No.13)

A solution of ((1α, 5α, 6α)-N-[3-azabicyclo[3.1.0]hex-6-yl]-2-hydroxy-2-cyclopentyl-2-phenylacetamide (1 mmol), 4-trifluoromethylbenzaldehyde (2.64 mmol), sodium triacetoxyborohydride (3.3 mmol) and acetic acid (3.8 mmol) in THF was stirred at room temperature for 4 days. The reaction mixture was poured into saturated aqueous sodium bicarbonate solution and extracted with dichloromethane. The organic layer was washed with water, dried and concentrated under reduced pressure. The residue was purified by column chromatography (100-200 mesh size silicagel) and compound was eluted with 20:80 EtOAc-hexane mixture $^1$HNMR (CDCl$_3$, δ-values): 7.60-7.23 (m, 9ArH), 6.49 (ds, 1H), 3.68 (s, 2H), 3.12-1.10 (m, 16H) IR (DCM): 1651 cm$^{-1}$

EXAMPLE 14

Preparation of (1α, 5α, 6α)-N-[3-(5-methyl-2-furyl-methyl)-3-azabicyclo[3.1.0], hex-6-yl]-2-hydroxy-2-cyclopentyl-2-phenylacetamide (Compound No.14)

The compound was synthesized by following the procedure of Example 13, using 5-methyl-2-furancarboxaldehyde instead of 4-trifluoromethylbenzaldehyde.

1HNMR (CDCl$_3$, δ-values): 7.57-5.99 (m, 7ArH), 5.84 (s, 1H), 3.53 (s, 2H), 3.09-249 (m, 7H), 2.24 (s, 3H), 1.63-1.16 (m, 9H). IR (DCM): 1638 cm$^{-1}$

EXAMPLE 15

Preparation of (1α, 5α, 6α)-N-[3-(2-(4-methylphenoxy)ethyl)-3-azabicyclo[3.1.0]hex-6-yl]-2-hydroxy-2-cyclopentyl-2-phenylacetamide (Compound No.15)

The compound was synthesized by following the procedure of Example 10, using 4-methylphenoxyethyl bromide instead of 3,5-dimethoxybenzylchloride.

The compound was eluted with 30:70—EtOAc-hexane mixture.

$^1$HNMR (CDCl$_3$, δ values): 7.58-6.73 (m, 9ArH), 6.48 (s, 1H), 4.01 (t, 3H), 3.25-2.63 (m, 9H), 2.26 (s, 3H), 1.62-1.18 (m, 9H) IR (DCM): 1652 cm$^{-1}$

EXAMPLE 16

Preparation of (1α, 5α, 6α)-N-[3-[3-nitrobenzyl)-3-azabicyclo[3.1.0]hex-6-yl]-2-hydroxy-2-cyclopentyl-2-phenylacetamide (Compound No.16)

The compound was prepared by following the procedure of Example 13 but using 3-nitrobenzaldehyde instead of 4-trifluoromethylbenzaldehyde.

$^1$HNMR (CDCl$_3$, δ-values): 8.09-7.23 (m, 9ArH), 6.47 (bs, 1H), 3.67 (6, 2H), 3.22-1.23 (m, 16H) IR (DCM): 1654 cm$^{-1}$

EXAMPLE 17

Preparation of (1α, 5α, 6α)-N-[3-(4-chlorophenethyl)-3-azabicyclo[3.1.0]hex-6-yl]-2-hydroxy-2-cyclopentyl-2-phenylacetamide (Compound No.17)

The compound was synthesized following the procedure of Example 5 but using 4-chlorophenylthylmethane sulphonate instead of 4-methylpentyl methanesulphonate.

$^1$HNMR (CDCl$_3$ δ-values): 7.58-7.06 (m, 9ArH), 6.39 (s, 1H), 3.16-3.11 (t, 2H), 3.02-0.87 (m, 18H) IR (DCM): 1657 cm$^{-1}$

EXAMPLE 18

Preparation of (1α, 5α6α)-N-[3-(4-nitrobenzyl)-3-azabicyclo[3.1.0]hex-yl]-2-hydroxy-2-cyclopentyl-2-phenylacetamide (Compound No.18)

The compound was synthesized using the procedure of Example 10, using 4-nitrobenzyl chloride instead of 3,5-dimethoxy benzyl chloride.

m.pt: 85-87° C. $^1$HNMR (CDCl$_3$, δ values): 7.58-7.06 (m, 9ArH), 6.39 (s, 1H), 3.16-3.11 (t, 2H), 3.02-0.87 (m, 18H) IR (DCM): 1657 cm$^{-1}$

EXAMPLE 19

Preparation of (1α, 5α, 6α)-N-[3-(3-phenylpropyl)-3-azabicyclo[3.1.0]hex-6-yl]-2-hydroxy-2-cyclopentyl-2-phenylacetamide (Compound No.19)

The compound was synthesized by following the procedure of Example 13, using phenylpropionaldehyde instead of 4-trifluoromethyl benzaldehyde.

$^1$HNMR(CDCl$_3$, δ-values): 7.59-7.12 (m, 10 ArH), 6.38 (bs, 1H), 3.11-1.25 (m, 22H)

EXAMPLE 20

Preparation of (1α, 5α, 6α)-N-[3-(3-hydroxybenzyl)-3-azabicyclo[3.1.0]hex-6-yl]-2-hydroxy-2-cyclopentyl-2-phenylacetamide (Compound No.20)

The compound was synthesized by following the procedure of Example 13, using 3-hydroxybenzaldehyde instead of 4-trifluoromethyl benzaldehyde.

$^1$HNMR (CDCl$_3$, δ-values): 7.59-6.67 (m, 9ArH), 6.54 (bs, 1H), 3.47 (s, 2H), 3.04-0.83 (m, 16H)

EXAMPLE 21

Preparation of (1α, 5α, 6α)-N-[3-(1-phenylethyl)-3-azabicyclo[3.1.0]hex-6-yl]-2-hydroxy-2-cyclopentyl-2-phenylacetamide (Compound No.21)

The compound was synthesized by following the procedure of Example 13, using acetophenone instead of 4-trifluoromethyl benzaldehyde.

$^1$HNMR (CDCl$_3$, δ-values): 7.58-7.15 (m, 10ArH), 6.36 (bs, 1H), 3.29 (q, 1H), 3.19-1.23 (m, 20H) IR (DCM): 1652 cm$^{-1}$

EXAMPLE 22

Preparation of (1α, 5α, 6α)-N-[3-(4-t-butylbenzyl)-3-azabicyclo[3.1.0]hex-6-yl]-2-hydroxy-2-cyclopentyl-2-phenylacetamide (Compound No.22)

The compound was synthesized by following the procedure of Example 10, using 4-t-butylbenzylbromide instead of 3,5-dimethoxybenzylbromide.

m.pt.: 60-62° C. $^1$HNMR (CDCl$_3$, δ-values): 7.58-7.12 (m, 9ArH), 6.35 (bs, 1H), 3.40 (s, 2H), 3.13-1.36 (m, 16H), 1.29 (s, 9H) IR (DCM): 1652 cm$^{-1}$

EXAMPLE 23

Preparation of (1α, 5α, 6α)-N-[3-(2-methylquinolinyl)-3-azabicyclo[3.1.0]hex-6-yl]-2-hydroxy-2-cyclopentyl-2-phenylacetamide (Compound No.23)

The compound was synthesized by following the procedure of Example 10 but using 2-chloromethyl quinoline instead of 3,5-dimethoxybenzylbromide.

m.pt.: 54-57° C. $^1$HNMR (CDCl$_3$, δ-values): 8.08-7.26 (m, 11ArH), 6.44 (bs, 1H), 3.87 (s, 2H), 3.13-1.15 (m, 16H) IR (DCM): 1646 cm$^{-1}$

EXAMPLE 24

Preparation of (1α, 5α, 6α)-N-[3-(3-nitro-4-methoxybenzyl)-3-azabicyclo[3.1.0]hex-6-yl]-2-hydroxy-2-cyclopentyl-2-phenylacetamide (Compound No.24)

The compound was synthesized by following the procedure of Example 13 but using 3-nitro-4-methoxybenzaldehyde instead of 4-trifluoromethyl benzaldehyde.

$^1$HNMR (CDCl$_3$, δ-values): 7.68-6.97 (m, 8ArH), 6.46 (bs, 1H), 3.93 (s, 3H), 3.50 (s, 2H), 3.04-1.10 (m, 16H) IR (DCM): 1650 cm$^{-1}$

EXAMPLE 25

Preparation of (1α, 5α, 6α)-N-[3-(3-nitro-4-hydroxybenzyl)-3-azabicyclo[3.1.0]hex-6-yl]-2-hydroxy-2-cyclopentyl-2-phenylacetamide (Compound No.25)

The compound was synthesized by following the procedure of Example 13 but using 3-nitro-4-hydroxy benzaldehyde instead of 4-trifluoromethyl benzaldehyde.

IR (DCM): 1658 cm$^{-1}$ $^1$HNMR (CDCl$_3$, δ-values): 7.91-7.05 (m, 8ArH), 6.44 (bs, 1H), 3.49 (s, 2H), 3.04-1.23 (m, 16H)

EXAMPLE 26

Preparation of (1α, 5α, 6α)-N-[3-(3,4-dichlorophenyl)-3-azabicyclo[3.1.0]hex-6-yl]-2-hydroxy-2-cyclopentyl-2-phenylacetamide (Compound No.26)

The compound was synthesized by following the procedure of Example 10, using 3,4-dichlorophenethyl methanesulphonate instead of 4-methylpentyl methane sulphonate.

$^1$HNMR (CDCl$_3$): 7.581-6.7 (m, 8ArH), 6.39 (bs, 1H), 3.14-0.88 (m, 20H)

EXAMPLE 27

Preparation of (1α, 5α, 6α)-N-[3-(3-aminobenzyl)-3-azabicyclo[3.1.0]hex-6-yl]-2-hydroxy-2-cyclopentyl-2-phenylacetamide (Compound No.27)

The solution of compound of Example 15 (1 mmol) in methanol was cooled in an ice bath and to it raney nickel and hydrazine hydrate (2 mmol) were added. The reaction mixture was further stirred for 2 hours in an ice bath. It was filtered over celite, the filtrate was concentrated, and the residue taken in DCM. The residue was washed with water, dried and purified by column chromatography (100-200 mesh, silicagel) eluting the compound with 70:30 EtOAc-hexane mixture.

$^1$HNMR (CDCl$_3$, δ-values: 7.59-6.52 (m, 9ArH), 6.37 (bs, 1H), 3.44 (s, 2H), 3.077-1.25 (m, 16H) IR (DCM): 1645 cm$^{-1}$

EXAMPLE 28

Preparation of (1α, 5α, 6α)-N-[3-(6-aminopyridin-2-yl-methyl)-3-azabicyclo[3.1.0]hex-6-yl]-2-hydroxy-2-cyclopentyl-2-phenylacetamide (Compound No.28)

Step-a: Synthesis of 6-tert-butoxy carbonyl amino-2-pyridine methyl methane sulphonate The compound was synthesized following the procedure described in J. Med. Chem., 2000, Vol. 43 (26), 5017-5029

Step-b: Synthesis of (1α, 5α, 6α)-N-[3-(6-tert-butoxycarbonyl aminopyridin-2-yl methyl)-3-azabicyclo[3.1.0]hex-6-yl]-2-hydroxy-2-cyclopentyl-2-phenylacetamide To a solution of compound of Step-a (1 mmol) in acetonitrile was added (1α, 5α, 6α)-N-[3-(azabicyclo[3.1.0]hex-6-yl]-2-hydroxy-2-cyclopentyl phenyl acetamide (1 mmol), potassium carbonate (3 mmol) and the RM was stirred overnight at RT. The RM was poured into water and extracted with EtOAc. The organic layers were dried and concentrated under reduced pressure. The residue was purified by column chromatography eluting the compound with 5:95 MeOH-DCM.

m.pt: 60° C. $^1$HNMR (CDCl$_3$, δ-values): 7.74-6.93 (m, 8ArH), 6.39 (bs, 1H), 3.54 (s, 2H), 3.10-2.43 (m, 6H), 1.65-1.01 (m, 19H) IR (DCM): 1658 cm$^{-1}$

Step-c: Synthesis of Preparation of (1α, 5α, 6α)-N-[3-(6-aminopyridin-2-yl-methyl)-3-azabicyclo[3.1.0]hex-6-yl]-2-hydroxy-2-cyclopentyl-2-phenylacetamide The compound of Step-b (1 mmol) was taken in EtOAc and EtOAc saturated with hydrochloric acid was added to the RM. The RM was stirred at RT for 3 days. The RM was cooled to 0° C. purified with aq. NaHCO$_3$. The organic layer was purified by 10% MeOH-DCM.

$^1$HNMR (CDCl$_3$): 7.59-6.33 (m, 8H), 3.57 (s, 2H), 3.14-2.44 (m, 7H), 1.89-1.15 (m, 9H)

EXAMPLE 29

Preparation of (1α, 5α, 6α)-N-[3-(2-phenoxyethyl)-3-azabicyclo[3.1.0]hex-6-yl]-2-hydroxy-2-cyclopentyl-2-phenylacetamide (Compound No.29)

The compound was synthesized following the procedure of Example 10 but using 2-phenoxyethylbromide instead of 3,5-dimethoxybenzylbromide.

$^1$HNMR (CDCl$_3$, δ-values): 7.58-6.83 (m, 10ArH), 6.38 (bs, 1H), 3.96 (t, 2H), 3.077-1.25 (m, 16H) IR (DCM): 1645 cm$^{-1}$

EXAMPLE 30

Preparation of (1α, 5α, 6α)-N-[3-(3-phenoxypropyl)-3-azabicyclo[3.1.0]hex-6-yl]-2-hydroxy-2-cyclopentyl-2-phenylacetamide (Compound No.30)

The compound was synthesized following the procedure of Example 10 using 3-phenoxypropylbromide instead of 3,5-dimethoxybenzylbromide.

$^1$HNMR (CDCl$_3$, δ values): 7.58-6.84 (m, 10ArH), 6.38 (bs, 1H), 3.93 (t, 2H), 3.13-1.42 (m, 20H) IR (DCM): 1652 cm$^{-1}$

EXAMPLE 31

Preparation of (1α, 5α, 6α)-N-[3-(2-methylpyrollyl)-3-azabicyclo[3.1.0]hex-6-yl]-2-hydroxy-2-cyclopentyl-2-phenylacetamide (Compound No.31)

The compound was synthesized following the procedure of Example 13 but using pyrrole-2-carboxaldehyde instead of 4-trifluoromethyl benzaldehyde.

$^1$HNMR (CDCl$_3$, δ-values): 9.17 (s, 1H), 7.58-6.05 (m, 8ArH), 5.96 (bs, 1H), 3.61 (s, 2H), 3.07-1.15 (m, 16H) IR (DCM): 1645 cm$^{-1}$

EXAMPLE 32

Preparation of (1α, 5α, 6α)-N-[3-(1,4-benzodioxan-6-yl)-methyl-3-azabicyclo[3.1.0]hex-6-yl]-2-hydroxy-2-cyclopentyl-2-phenylacetamide (Compound No.32)

The compound was synthesized following the procedure of Example 13 using 1,4-benzodioxan-6-carboxaldehyde instead of 4-trifluoromethyl benzaldehyde.

m.pt.: 61-64° C. $^1$HNMR (CDCl$_3$, δ-values): 7.57-6.65 (m, 8ArH), 6.33 (bs, 1H), 4.22 (s, 4H), 3.41 (s, 2H), 3.04-1.10 (m, 16H) IR (DCM): 1655 cm$^{-1}$

EXAMPLE 33

Preparation of (1α, 5α, 6α)-N-[3-benzyl-3-azabicyclo[3.1.0]hex-6-yl]-2-hydroxy-2-cyclobutyl-2-phenylacetamide (Compound No.33)

The compound was prepared by the following procedure:

Step-a: Synthesis of 2-hydroxy-2-cyclobutyl-2-phenylacetic acid

This was synthesized as per reported procedure of Saul B. Kadin and Joseph G. Cannon, J. Org. Chem., 1962, 27, 240-245.

Step-b: Synthesis of (1α, 5α6α)-N-[3-benzyl-3-azabicyclo[3.1.0]hex-6-yl]-2-hydroxy-2-cyclobutyl-2-phenylacetamide This compound was prepared by following the procedure of Example 2, Step-b but using 2-hydroxy-2-cyclobutyl-2-phenylacetic acid instead of 2-hydroxy-2-cyclohexyl-2-phenyl acetic acid.

¹HNMR (CDCl₃, δ-values): 7.47-6.19 (m, 10ArH), 6.19 (bs, 1H), 3.52 (s, 2H), 3.36-3.27 (m, 1H), 3.06-2.98 (m, 3H), 2.35-2.32 (m, 2H), 1.88-1.74 (m, 8H).

EXAMPLE 34

Preparation of (1α, 5α, 6α)-N-[3-(4-methyl-3-pentyl)-3-azabicyclo[3.1.0]hex-6-yl]-2-hydroxy-2-cyclobutyl-2-phenylacetamide (Compound No.34)

Step-a: Synthesis of (1α, 5α, 6α)-N-[3-azabicyclo [3.1.0]hex-6-yl]-2-cyclobutyl-2-hydroxy-2-phenylacetamide The compound was prepared following the procedure of Example 2, Step-c by using (1α, 5α, 6α)-N-[3-benzyl-3-azabicyclo[3.1.0]hex-6-yl]-2-cyclobutyl-2-hydroxy-2-phenyacetamide instead of (1α, 5α, 6α)-N-[3-benzyl-3-bicyclo [3.1.0]hex-6-yl-2-cyclohexyl-2-hydroxy-2-phenylacetamide.

Step-b: Synthesis of compound (1α, 5α, 6α)-N-[3-benzyl-3-azabicyclo[3.1.0]hex-6-yl]-2-hydroxy-2-cyclobutyl-2-phenylacetamide The compound was synthesized following the procedure of Example 5 using (1α, 5α, 6α)-N-[3-azabicyclo[3.1.0]-hex-6-yl-2-cyclobutyl-2-hydroxy-2-phenylacetamide instead of (1α, 5α, 6α)-N-[3-azabicyclo[3.1.0]-hex-6-yl]-2-cyclopentyl-2-hydroxy-2-phenylacetamide and 5-bromo-2-methyl-pent-3-ene instead of 4-methylpentyl methane sulphonate.

¹HNMR (CDCl₃, δ-values): 7.48-7.26 (m, 5ArH), 6.13 (bs, 1H), 5.07-5.03 (t, 1H), 3.49 (bs, 1H), 3.34 (m, 1H), 3.10 (m, 2H), 2.86 (s, 1H), 2.33 (m, 4H), 2.09-1.57 (m, 16H). IR (DCM): 1651 cm⁻¹

EXAMPLE 35

Preparation of (1α, 5α, 6α)-N-[3-[2-(3,4-methylendioxyphenyl)ethyl]-3-azabicyclo[3.1.0]hex-6-yl]-2-hydroxy-2-cyclobutyl-2-phenylacetamide (Compound No.35)

The compound was prepared by following the procedure of Example 10 but using 3,4-methylenedioxy phenethylbromide instead of 3,5-dimethoxybenzyl bromide and (1α, 5α, 6α)-N-3-[azabicyclo[3.1.0]hex-6-yl]-2-hydroxy-2-cyclobutyl-2-phenylacetamide instead of (1α, 5α, 6α)-N-[3-azabicyclo[3.1.0]hex-6-yl]-2-hydroxy-2-cyclopentyl-2-phenyl-acetamide.

¹HNMR (CDCl₃): 7.48-7.29 (m, 5H), 6.7-6.58 (m, 3H), 6.16 (s, 1H), 5.9 (s, 2H), 3.33 (m, 1H), 3.13 (m, 2H), 2.84 (s, 1H), 2.56 (m, 4H) 2.33 (m, 2H),2.054-1.6 (m, 8H).

EXAMPLE 36

Preparation of (1α, 5α, 6α)-N-[3-benzyl-3-azabicyclo [3.1.0]hex-6-yl]-2-hydroxy-2-cyclopropyl-2-phenylacetamide (Compound No.36)

Step-a: Synthesis of 2-hydroxy-2-cyclopropyl-2-phenylacetic acid

The compound was synthesized as per reported procedure of Saul B. Kadin and Joseph G. Cannon, J. Org. Chem. 1962, 27, 240-245.

Step-b: Synthesis of (1α, 5α6α)-N-[3-benzyl-3-azabicyclo[3.1.0]hex-6-yl]-2-hydroxy-2-cyclopropyl-2-phenylacetamide The above compound was prepared by following the procedure of Example 2, Step-b using 2-hydroxy-2-cyclopropyl-2-phenylacetic acid instead of 2-hydroxy-2-cyclohexyl-2-phenylacetic acid.

¹HNMR (CDCl₃, δ-values): 7.59-7.29 (m, 5H), 6.05 (bs, 1H), 3.54 (s, 2H), 3.06 (m, 3H), 2.37 (m, 2H), 2.04 (s, 1H), 1.54-1.45 (m, 3H), 0.54 (m, 4H). IR (DCM): 1648 cm⁻¹

EXAMPLE 37

Preparation of (1α, 5α, 6α)-N-[3-[4-methyl-3-pentenyl)-3-azabicyclo [3.1.0]hex-6-yl]-2-hydroxy-2-cyclopropyl-2-phenylacetamide (Compound No.37)

Step-a: Synthesis of (1α, 5α, 6α)-N-[3-azabicyclo [3.1.0]hex-6-yl]-2-cyclopropyl-2-hydroxy-2-phenylacetamide The compound was prepared by following the procedure of Example 2 step-c, using (1α, 5α, 6α)-N-[3-benzyl-3-azabicyclo-[3.1.0]hex-6-yl]-2-cyclopropyl-2-phenylacetamide instead of (1α, 5α, 6α)-N-[3-benzyl-3-azabicyclo-[3.1.0] hex-6-yl]-2-hydroxy-2-cyclohexyl-2-phenylacetamide.

Step-b: Synthesis of (1α, 5α, 6α)-N-[3-[4-methyl-3-pentenyl)-3-azabicyclo [3.1.0]hex-6-yl]-2-2-hydroxy-2-cyclopropyl-2-phenylacetamide The compound was synthesized following the procedure of Example 5 using(1α, 5α, 6α)-N-[3-azabicyclo[3.1.0]hex-6-yl]-2-cyclopropyl-2-hydroxy-2-phenylacetamide instead of (1α, 5α, 6α)-N-[3-azabicyclo[3.1.0]hex-6-yl]-2-cyclopentyl-2-hydroxy-2-phenylacetamide and 5-bromo-5-methyl-pent-3-one instead of 4-methylpentyl methane sulphonate.

¹HNMR (CDCl₃, δ-values): 7.59-7.29 (m, 5H), 6.00 (s, 1H), 5.06 (t, 1H), 3.44 (bs, 1H), 3.12 (m, 2H), 2.94 (s, 1H), 2.34 (m, 4H), 2.06 (m, 2H), 1.66-1.45 (m, 0H), 0.56 (m, 4H) IR (DCM): 1651 cm⁻¹

EXAMPLE 38

Preparation of (1α, 5α, 6α)-N-[3-2-(3,4-methylenedioxyphenyl)ethyl]-3-azabicyclo [3.1.0]hex-6-yl]-2-hydroxy-2-cyclopropyl-2-phenylacetamide (Compound No.38)

The compound was prepared following the procedure of Example 10 using 3,4-methylenedioxyphenethylbromide instead of 3,4-dimethoxybenzylbromide and (1α, 5α, 6α)-N-[3-azabicyclo[3.1.0]hex-6-yl]-2-hydroxy-2-cyclopropyl-2- phenylacetamide instead of (1α, 5α, 6α)-N-[3-azabicyclo[3.1.0]hex-6-yl]-2-hydroxy-2-cyclopentyl-2-phenylacetamide.

¹HNMR (CDCl₃, δ-values): 7.59-7.30 (m, 5H), 6.67-6.66 (m, 3H), 6.03 (s, 1H), 5.9 (s, 2H), 3.17 (m, 2H), 2.92 (s, 1H), 2.58 (m, 4H), 2.36 (m, 2H), 1.65-1.47 (m, 3H), 0.08 (m, 1H), 0.05 (m, 4H) IR (DCM): 1649 cm⁻¹

EXAMPLE 39

Preparation of (1α, 5α6α)-N-[3-(4-hydroxy-3-methoxybenzyl)]-3-azabicyclo[3.1.0]hex-6-yl]-2-hydroxy-2-cyclopentyl-2-phenylacetamide (Compound No.39)

The compound was prepared following the procedure of Example 13 using 4-hydroxy-3-methoxybenzaldehyde instead of 4-trifluoromethylbenzaldehyde.

m.pt: 68-73° C. ¹HNMR (CDCl₃, δ values): 7.58-6.78 (m, 8ArH), 6.66 (bs, 1H), 6.41 (s, 1H), 5.85 (s, 3H), 3.46 (s, 2H), 3.05-1.11 (m, 17H) IR DCM: 1654 cm⁻¹

EXAMPLE 40

Preparation of (1α, 5α6α)-N-[3-(3-hydroxy-4-methoxybenzyl)]-3-azabicyclo[3.1.0]hex-6-yl]-2-hydroxy-2-cyclopentyl-2-phenylacetamide (Compound No.40)

The compound was prepared following the procedure of Example 13 using 3-hydroxy-4-methoxybenzaldehyde instead of 4-trifluoromethylbenzaldehyde.

m.pt: 66-73° C. ¹HNMR (CDCl₃, δ-value): 7.57-6.67 (m, 8ArH), 6.37 (bs, 1H), 3.85 (s, 3H), 3.45 (s, 2H), 3.13-2.94 (m, 4H), 2.38-2.35 (m, 2H), 1.67-1.25 9m, 10H) IR (DCM): 1655 cm⁻¹

EXAMPLE 41

Preparation of (1α, 5α, 6α)-N-[3-(2-phenylcarboethoxyethyl]-3-azabicyclo[3.1.0]hex-6-yl]-2-hydroxy-2-cyclopentyl-2-phenylacetamide (Compound No.41)

The compound was synthesized following the procedure of Example 10 using 2-bromoethylphenylacetate instead of 3,5-dimethoxybenzylchloride.

¹HNMR (CDCl₃, δ values): 7.58-7.26 (m, 10ArH), 6.38 (bs, 1H), 4.12-4.01 (m, 3H), 3.15-2.33 (m, 6H), 1.60-0.85 (m, 13H) IR (DCM): 1646 and 1741 cm⁻¹

EXAMPLE 42

Preparation of (1α, 5α6α)-N-[3-[1-(2-hydroxyphenyl)ethyl]-3-azabicyclo[3.1.0]hex-6-yl]-2-hydroxy-2-cyclopentyl-2-phenylacetamide (Compound No.42)

The compound was synthesized following the procedure of Example 13 using 2-hydroxyacetophenone instead of 4-trifluoromethyl benzaldehyde.

¹HNMR (CDCl₃, δ-values): 7.57-6.70 (m, 9ArH), 6.45 (bs, 1H), 3.38-1.16 (m, 20H) IR (DCM): 1655 cm⁻¹

EXAMPLE 43

Preparation of (1α, 5α, 6α)-N-[3-[1-(4-methylphenyl)ethyl]-3-azabicyclo[3.1.0]hex-6-yl]-2-hydroxy-2-cyclopentyl-2-phenylacetamide (Compound No.43)

The compound was synthesized by following the procedure of Example 13 using 4-methylacetophenone instead of 4-trifluoromethylbenzaldehyde.

¹HNMR (CDCl₃, δ-values): 7.58-7.04 (m, 9ArH), 6.33 (bs, 1H), 3.28-1.45 (m, 12H), 1.25-1.21 (m, 11H)) IR (DCM): 1646 cm⁻¹

EXAMPLE 44

Preparation of (1α, 5α, 6α)-N-[3-(3-(1-bromophenylmethyl)pyridine)-3-azabicyclo[3.1.0]hex-6-yl]-2-hydroxy-2-cyclopentyl-2-phenylacetamide (Compound No.44)

The above compound was prepared by following the procedure of Example 10 using 3-(1-bromophenyl methyl)pyridine hydrochloride instead of 3,5-dimethoxybenzylbromide.

¹HNMR (CDCl₃, δ-values): 8.45-7.06 (m, 14ArH), 6.46 (bs, 1H), 4.17 (s, 1H), 3.12-0.91 (m, 16H) IR (DCM): 1660 cm⁻¹

EXAMPLE 45

Preparation of (1α, 5α, 6α)-N-[3-(4-pyridylmethyl)-3-azabicyclo[3.1.0]hex-6-yl]-2-hydroxy-2-cyclopentyl-2-phenylacetamide (Compound No.45)

The compound was synthesized following the procedure of Example 10 using 4-chloromethylpyridine hydrochloride instead of 3,5-dimethoxybenzylbromide.

m.pt: 70-73° C. ¹HNMR (CDCl₃, δ-values): 7.40-7.16 (m, 15ArH), 6.27 (bs, 1H), 3.82 (s, 1H), 3.33-1.24 (m, 11H) IR (DCM): 1657 cm⁻¹

EXAMPLE 46

Preparation of (1α, 5α, 6α)-N-[3-(1-indanyl)-3-azabicyclo[3.1.0]hex-6-yl]-2-hydroxy-2-cyclopentyl-2-phenylacetamide (Compound No.46)

To a solution of (1α, 5α, 6α)-N-(3-azabicyclo[3.1.0]hex-6-yl]-2-hydroxy-2-cyclopentyl-2-phenylacetamide (1 mmol) in THF was added 1-bromoindan (1.5 mmol) and N-ethyldiisopropylamine (4 mmol) under nitrogen atmosphere. The reaction mixture was stirred at room temperature for 5 days. The reaction mixture was poured into saturated sodium bicarbonate solution and extracted with EtOAc. The organic layer was dried, concentrated under reduced pressure and purified by column chromatography (silicagel, 100-200 mesh) eluting the compound with 30:70 EtOAc-hexane.

¹HNMR (CDCl₃, δ-values): 7.58-7.12 (m, 9ArH), 6.36 (bs, 1H), 4.26-4.22 (t, 1H), 3.06-0.85 (m, 20H) IR (DCM): 1652 cm⁻¹

EXAMPLE 47

Preparation of (1α, 5α, 6α)-N-[3-(3-methylbenzyl)-3-azabicyclo[3.1.0]hex-6-yl]-2-hydroxy-2-cyclopentyl-2-phenylacetamide (Compound No.47)

The compound was synthesized following the procedure of Example 13 using 3-methylbenzaldehyde instead of 4-trifluoromethylbenzaldehyde.

$^1$HNMR (CDCl$_3$, δ-values): 7.58-6.99 (m, 9ArH), 6.36 (bs, 1H), 3.49 (s, 2H), 3.06-0.87 (m, 19H) IR (DCM): 1645 cm$^{-1}$

EXAMPLE 48

Preparation of (1α, 5α, 6α)-N-[3-(2,4,6-trimethylbenzyl)-3-azabicyclo[3.1.0]hex-6-yl]-2-hydroxy-2-cyclopentyl-2-phenylacetamide (Compound No.48)

The compound was synthesized following the procedure of Example 13 using 2,4,6-trimethylbenzaldehyde instead of 4-trifluoromethylbenzaldehyde.

$^1$HNMR (CDCl$_3$, δ-values): 7.56-7.22 (m, 7ArH), 6.30 (bs, 1H), 3.49 (s, 2H), 3.10-0.85 (m, 25H). IR (DCM): 1646 cm$^{-1}$

EXAMPLE 49

Preparation of (1α, 5α, 6α)-N-[3-[2-(3,4-dimethoxyphenyl)ethyl-3-azabicyclo[3.1.0]hex-6-yl]-2-hydroxy-2-cyclopentyl-2-phenylacetamide (Compound No.49)

Step-a: Synthesis of 3,4-dimethoxyphenethylbromide

The compound was synthesized as per reported procedure in EP 0388054A1, using 1,2-dimethoxybenzene instead of 2,3-dihydrobenzofuran.

Step-b: Synthesis of (1α, 5α, 6α)-N-[3-[2-(3,4-dimethoxyphenyl)ethyl-3-azabicyclo[3.1.0]hex-6-yl]-2-hydroxy-2-cyclopentyl-2-phenylacetamide The compound was synthesized following the procedure described in Example 10 using 3,4-dimethoxyphenethyl bromide instead of 3,5-dimethoxybenzylbromide.

$^1$HNMR (CDCl$_3$, δ-values): 7.58-7.56 (d, 2ArH), 7.36-7.23 (m, 3H), 6.77-6.67 (m, 3H), 6.39 (bs, 1H), 3.88-3.83 (s, 6H), 3.18-3.15 (d, 2H), 3.15-2.37 (m, 10H), 1.73-0.87 (m, 10H) IR (DCM): 1642 cm$^{-1}$

EXAMPLE 50

Preparation of (1α, 5α6α)-N-[3-[2-(3,4-dimethylphenyl)ethyl-3-azabicyclo[3.1.0]hex-6-yl]-2-hydroxy-2-cyclopentyl-2-phenylacetamide (Compound No.50)

Step-a: Synthesis of 3,4-dimethylphenethylbromide

The compound was synthesized as per reported procedure in EP0388054A1 using o-xylene instead of 2,3-dihydrobenzofuran.

Step-b: Synthesis of (1α, 5α, 6α)-N-[3-[2-(3,4-dimethylphenyl)ethyl-3-azabicyclo[3.1.0]hex-6-yl]-2-hydroxy-2-cyclopentyl-2-phenylacetamide The compound was synthesized following the procedure described in Example 10 using 3,4-dimethylphenethyl bromide instead of 3,5-dimethoxy benzylbromide.

$^1$HNMR (CDCl$_3$): 7.58-7.56 (d, 2ArH), 7.38-7.28 (m, 2ArH), 7.28-6.36 (m, 2ArH), 7.02-7.00 (d, 1ArH), 6.92-6.87 (m, 2ArH), 6.36 (bs, 1H), 3.16-3.13 (m, 3H), 3.02-2.99 (m, 1H), 2.85 (bs, 1H), 2.63-2.53 (m, 4H), 2.37-2.34 (m, 2H), 2.20 (bs, 6H), 1.63-1.25 (m, 11H) IR (DCM): 1646 cm$^{-1}$

EXAMPLE 51

Preparation of (1α, 5α, 6α)-N-[3-pentyl-3-azabicyclo[3.1.0]hex-6-yl]-2-hydroxy-2-cyclopentyl-2-phenylacetamide (Compound No.51)

The compound was synthesized following the procedure of Example 10, using 1-bromopentane instead of 3,5-dimethoxybenzylchloride.

$^1$HNMR (CDCl$_3$, δ-values): 7.58-7.55 (d, 2ArH), 7.35-7.22 (m, 3H), 6.35 (bs, 1H), 3.09-3.06 (m, 3H), 2.98 (m, 1H), 2.85 (bs, 1H), 2.31-2.27 (m, 4H), 1.77-0.83 (m, 7H)

EXAMPLE 52

Preparation of (1α, 5α, 6α)-N-[3-(4-cyanobenzyl)-3-azabicyclo[3.1.0]hex-6-yl]-2-hydroxy-2-cyclopentyl-2-phenylacetamide (Compound No.52)

The compound was prepared following the procedure of Example 10, using 4-cyanobenzylbromide instead of 3,5-dimethoxybenzylchloride.

$^1$HNMR (CDCl$_3$, δ-values): 7.58-7.53 (m, 4ArH), 7.34-7.26 (m, 5ArH), 6.47 (bs, 1H), 3.57 (s, 2H), 3.06-2.97 (m, 4H), 2.35 (d, 2H, J=7.6), 1.64-1.45 (m, 8H), 1.25-1.16 (m, 2H), IR (KBr): 1652 cm$^{-1}$, 2228 cm$^{-1}$

EXAMPLE 53

Preparation of (1α, 5α, 6α)-N-[3-(2-cyanobenzyl)-3-azabicyclo [3.1.0]hex-6-yl]-2-hydroxy-2-cyclopentyl-2-phenylacetamide (Compound No.53)

To a solution of (1α, 5α6α)-N-[3-azabicyclo[3.1.0]hex-6-yl]-2-hydroxy-2-cyclopentyl-2-phenylacetamide (1 mmol) in DMF (10 ml) was added 2-cyanobenzylbromide (1.2 mmol), potassium carbonate (2 mmol) and potassium iodide (2 mmol). The reaction mixture was stirred overnight at room temperature, poured into water and extracted with ethyl acetate. The organic layer was dried and concentrated under reduced pressure. The residue was purified by column chromatography (100-200 mesh silicagel) eluting the compound with 25.75 EtOAc-hexane mixture.

$^1$HNMR (CDCl$_3$, δ-value): 7.59-7.23 (m, 10ArH), 6.40 (bs, 1H), 3.73 (s, 2H), 3.09-2.96 (m, 5H), 2.48-2.43 (m, 2H), 1.55-1.25 (m, 8H), 1.30-1.25 (m, 2H) IR (KBr): 1651 cm$^{-1}$, 2225 cm$^{-1}$

EXAMPLE 54

Preparation of (1α, 5α, 6α)-N-[3-(2,3,4,5,6-pentafluorobenzyl)-3-azabicyclo [3.1.0]hex-6-yl]-2-hydroxy-2-cyclopentyl-2-phenylacetamide (Compound No.54)

The compound was synthesized following the procedure of Example 10 using 2,3,4,5,6-pentafluorobenzylbromide instead of 3,5-dimethoxybenzylchloride.

$^1$HNMR (CDCl$_3$, δ-values): 7.57-7.22 (m, 5ArH), 6.38 (s, 1H), 3.72 (s, 2H), 3.05-1.23 (m, 16H), IR (KBr): 1653 cm$^{-1}$

EXAMPLE 55

Preparation of (1α, 5α, 6α)-N-[3-(4-cyanobenzyl)-3-azabicyclo [3.1.0]hex-6-yl]-2-hydroxy-2-cyclohexyl-2-phenylacetamide (Compound No.55)

The compound was prepared following the procedure of Example 53, using cyanobenzylbromide instead of 2-cyanobenzylbromide.

m.pt.:66° C. $^1$HNMR (CDCl$_3$, δ-value): 7.66-7.46 (m, 4ArH), 7.33-7.26 (m, 5ArH), 6.66 (bs, 1H), 3.57 (s, 2H), 3.07-2.98 (m, 3H), 2.69 (m, 1H), 2.44-2.33 (m, 3H), 1.81-1.77 (m, 1H), 1.46-1.43 (m, 2H), 1.25-1.11 (m, 7H), 0.90-0.82 (m, 2H) IR (KBr): 1655 cm$^{-1}$, 2228 cm$^{-1}$

EXAMPLE 56

Preparation of (1α, 5α, 6α)-N-[3-(3-methylpyridyl)-3-azabicyclo [3.1.0]hex-6-yl]-2-hydroxy-2-cyclopentyl-2-phenylacetamide (Compound No.56)

The compound was prepared following the procedure of Example 10, using 3-chloromethylpyridine hydrochloride instead of 3,5-dimethoxybenzylchloride.

$^1$HNMR (CDCl$_3$, δ-value): 8.45-7.18 (m, (ArH), 6.44 (bs, 1H), 3.53 (s, 2H), 3.05-1.17 (m, 16H). IR (KBr): 1653 cm$^{-1}$

EXAMPLE 57

Preparation of (1α, 5α, 6α)-N-[3-(4-bromo-2-methylthienyl)-3-azabicyclo [3.1.0]hex-6-yl]-2-hydroxy-2-cyclopentyl-2-phenylacetamide (Compound No.57)

The compound was prepared following the procedure of Example 13, using 4-bromo-thiophene-2-carboxaldehyde instead of 4-trifluoromethylbenzaldehyde.

$^1$HNMR (CDCl$_3$, δ-values): 7.58-6.74 (m, 7ArH), 6.40 (bs, 1H), 3.74 (s, 2H), 3.13-1.10 (m, 16H) IR (KBr): 1653 cm$^{-1}$

EXAMPLE 58

Preparation of (1α, 5α, 6α)-N-[3-[1-(phenyl)ethyl]-3-azabicyclo [3.1.0]hex-6-yl]-2-hydroxy-2-cyclohexyl-2-phenylacetamide (Compound No.58)

The compound was prepared following the procedure of Example 10, using 1-phenylethyl bromide instead of 3,5-dimethoxybenzylbromide.

$^1$HNMR (CDCl$_3$, δ-values): 7.59-6.17 (m, 10ArH), 6.57 (bs, 1H), 4.13-4.10 (Q, 1H), 3.28-0.87 (m, 21H) IR (DCM): 1659 cm$^{-1}$

EXAMPLE 59

Preparation of (1α, 5α, 6α)-N-[3-[2-nitrobenzyl]-3-azabicyclo[3.1.0]hex-6-yl]-2-hydroxy-2-cyclopentyl-2-phenylacetamide (Compound No.59)

The compound was prepared following the procedure of Example 13, using 2-nitrobenzaldehyde instead of 4-trifluoromethylbenzyldehyde.

m.pt: 161-163° C. $^1$HNMR (CDCl$_3$, δ-values): 7.81-7.23 (m, 9ArH), 6.38 (bs, 1H), 3.84 (s, 2H), 3.08-1.25 (m, 16H) IR (DCM): 1640 cm$^{-1}$

EXAMPLE 60

Preparation of (1α, 5α, 6α)-N-[3-[4-methoxycarbonyl]benzyl]-3-azabicyclo [3.1.0]hex-6-yl]-2-hydroxy-2-cyclopentyl-2-phenylacetamide (Compound No.61)

The compound was synthesized following the procedure of Example 10, using methyl-4-(bromomethyl)benzoate instead of 3,5 dimethoxybenzylchloride.

$^1$HNMR (CDCl$_3$, δ-values): 7.94-7.23 (m, 9ArH), 6.40 (bs, 1H), 3.89 (s, 3H), 3.57 (s, 2H), 3.07-0.82 (m, 16H) IR (DCM): 1643 cm$^{-1}$

EXAMPLE 61

Preparation of (1α, 5α, 6α)-N-[3-[diphenylmethyl]-3-azabicyclo[3.1.0]hex-6-yl]-2-hydroxy-2-cyclopentyl-2-phenylacetamide (Compound No.61)

The compound was synthesized following the procedure of Example 10, using benzhydrylbromide instead of 3,5-dimethoxybenzylchloride.

$^1$HNMR (CDCl$_3$) δ-values): 7.59-7.10 (m, 15ArH), 6.39 (bs, 1H), 4.16 (s, 1H), 3.13-0.82 (m, 16H) IR (DCM): 1652 cm$^{-1}$

EXAMPLE 62

Preparation of (1α, 5α, 6α)-N-[3-(4-carboxybenzyl)-3-azabicyclo[3.1.0]hex-6-yl]-2-hydroxy-2-cyclopentyl-2-phenylacetamide (Compound No.62)

The solution of compound (1α, 5α, 6α)-N-[3-(4-carbomethoxybenzyl)-3-azabicyclo [3.1.0]hex-6-yl]-2-hydroxy-2-cyclopentyl-2-phenylacetamide (1 mmol) in methanol (20 ml) containing lithiumhydroxide (4 mmol) in 5 ml of water was stirred at room temperature for 24 hours. The reaction mixture was concentrated under reduced pressure, the residue was cooled in ice and acidified with acetic acid. It was extracted with ethyl acetate and the residue after removing the solvent was purified by column chromatography (100-200 mesh silicagel) eluting the compound with ethyl acetate.

m.pt: 124°-129° C. $^1$HNMR (DMSO-d$_6$, δ-values): 7.88-7.21 (m, 9ArH), 5.46 (s, 1H), 3.59 (s, 2H), 2.94-1.18 (m, 16H) IR (DCM): 1656 cm$^{-1}$

EXAMPLE 63

Preparation of (1α, 5α, 6α)-N-[3-(2-aminobenzyl)-3-azabicyclo[3.1.0]hex-6-yl]-2-hydroxy-2-cyclopentyl-2-phenylacetamide (Compound No.63)

The compound was synthesized following the procedure of Example 27, using (1α, 5α, 6α)-N-[3-(2-nitrobenzyl)-3-azabicyclo[3.1.0]hex-6-yl]-2-hydroxy-2-cyclopentyl-2-phenylacetamide.

m.pt: 67-72° C. $^1$HNMR (CDCl$_3$, δ-values): 7.58-6.56 (m, 9ArH), 6.43 (bs, 1H), 3.51 (s, 2H), 3.02-0.83 (m, 16H) IR (DCM): 1647 cm$^{-1}$

EXAMPLE 64

Preparation of (1α, 5α, 6α)-N-[3-(2-carboethoxypropyl)]-3-azabicyclo[3.1.0]hex-6-yl]-2-hydroxy-2-cyclopentyl-2-phenylacetamide (Compound No.64)

The compound was synthesized following the procedure of Example 46, using ethyl-2-bromopropionate instead of 1-bromoindan.

$^1$HNMR (CDCl$_3$, δ-values): 7.58-7.23 (m, 5ArH), 6.38 (bs, 1H), 4.15-4.07 (q, 2H), 3.28-1.21 (m, 23H). IR (DCM): 1652 cm$^{-1}$ and 1731 cm$^{-1}$

EXAMPLE 65

Preparation of (1α, 5α, 6α)-N-[3-(2-(4-acetylphenyl)-3-azabicyclo[3.1.0]hex-6-yl]-2-hydroxy-2-cyclopentyl-2-phenylacetamide (Compound No.65)

The above compound was prepared by following the procedure of Example 53, using 2-(4-acetylphenyl)ethylbromide instead of 2-cyanobenzylbromide.

$^1$HNMR (CDCl$_3$, δ-values): 8.09-7.83 (m, 2ArH), 7.59-7.56 (m, 2ArH), 7.36-7.22 (m, 5ArH), 6.39 (bs, 1H), 3.76-3.16 (m, 2H), 3.14-2.83 (m, 3H), 2.75-2.63 (m, 4H), 2.58-2.57 (bs, 3H), 2.36 (bs, 2H), 1.67-0.87 (m, 10H) IR (DCM): 1662 cm$^{-1}$

EXAMPLE 66

Preparation of (1α, 5α, 6α)-N-[3-(2-(4-methoxycarbonyl)phenyl)ethyl-3-azabicyclo[3.1.0]hex-6-yl]-2-hydroxy-2-cyclopentyl-2-phenylacetamide (Compound No.66)

The compound was synthesized by following the procedure of Example 10, using 4-methoxycarbonyl phenethylbromide instead of 3,5-dimethoxybenzylchloride.

$^1$HNMR (CDCl$_3$, δ-values): 7.93-7.90 (d, 2H), 7.58-7.56 (d, 2), 7.35-7.30 (M, 2H), 7.27-7.20 (m, 3H), 6.36 (bs, 1H), 3.88 (s, 3H), 3.15-3.12 (d, 2H), 3.09 (bs, 1H), 3.01-2.99 (m, 1H), 2.82 (bs, 1H), 2.75-2.71 (m, 2H), 2.64-2.59 (m, 2H), 2.37-2.34 (m, 2H), 1.63-1.16 (m, 11H) IR (DCM): 1654 cm$^{-1}$ and 1720 cm$^{-1}$

EXAMPLE 67

Preparation of (1α, 5α, 6α)-N-[3-[3-cyanobenzyl]-3-azabicyclo-[3.1.0]hex-6-yl]-2-hydroxy-2-cyclopentyl-2-phenylacetamide (Compound No.67)

The compound was synthesized following the procedure of Example 53, using 3-cyanobenzylbromide instead of 2-cyanobenzylbromide.

$^1$HNMR (CDCl$_3$, δ-values): 7.59-7.46 (m, 5ArH), 7.38-7.23 (m, 4ArH), 6.41 (bs, 1H), 3.54 (s, 2H), 3.05-2.95 (m, 5H), 2.38-2.34 (m, 2H), 1.68-1.41 (m, 8H), 1.20-1.17 (m, 2H) IR (DCM): 1648 cm$^{-1}$ and 2229 cm$^{-1}$

EXAMPLE 68

Preparation of (1α, 5α, 6α)-N-[3-[2-cyanobenzyl]-3-azabicyclo-[3.1.0]hex-6-yl]-2-hydroxy-2-cyclohexyl-2-phenylacetamide (Compound No.68)

The compound was synthesized following the procedure of Example 53, using (1α, 5α, 6α)-N-[3-azabicyclo-[3.1.0]hex-6-yl]-2-hydroxy-2-cyclohexyl-2-phenylacetamide-2-phenylacetamide instead of (1α, 5α, 6α)-N-[3-azabicyclo[3.1.0]-hex-6-yl]-2-hydroxy-2-cyclopentyl-2-phenylacetamide.

$^1$HNMR (CDCl$_3$, δ-values): 7.58-7.24 (m, 9ArH), 6.65 (bs, 1H), 3.73 (s, 2H), 3.10-2.73 (m, 3H), 2.48 (m, 1H), 2.46-2.42 (m, 3H), 1.68-1.65 (m, 1H), 1.62-m, 9H), 0.99-0.95 (m, 2H). IR (DCM): 1648 cm$^{-1}$ and 2224 cm$^{-1}$

EXAMPLE 69

Preparation of (1α, 5α, 6α)-N-[3-(3-cyanobenzyl)-3-azabicyclo-[3.1.0]hex-6-yl]-2-hydroxy-2-cyclohexyl-2-phenylacetamide (Compound No.69)

The compound was synthesized following the procedure of Example 53, using (1α, 5α, 6α)-N-[3-azabicyclo-[3.1.0]hex-6-yl]-2-hydroxy-2-cyclohexyl-2-phenylacetamide instead of (1α, 5α, 6α)-N-[3-azabicyclo[3.1.0]-hex-6-yl]-2-hydroxy-2-cyclopentyl-2-phenylacetamide and 3-cyanobenzyl bromide instead of 2-cyanobenzylbromide.

m.pt: 68-70° C. $^1$HNMR (CDCl$_3$, δ-values): 7.59-7.46 (m, 5ArH), 7.38-7.22 (m, 4ArH) 6.63 (bs, 1H), 3.54 (s, 2H), 3.06-2.97 (m, 3H), 2.68 (m, 1H), 2.39-2.34 (m, 3H), 1.81-1.77 (m, 1H), 1.66-1.16 (m, 9H), 0.87-0.83 (m, 2H). IR (DCM): 1654 cm$^{-1}$ and 2229 cm$^{-1}$

EXAMPLE 70

Preparation of (1α, 5α, 6α)-N-[3-(3-methylbutyl)-3-azabicyclo-[3.1.0]hex-6-yl]-2-hydroxy-2-cyclohexyl-2-phenylacetamide (Compound No.70)

The compound was synthesized following the procedure of Example 53, using (1α, 5α, 6α)-N-[3-azabicyclo-[3.1.0]hex-6-yl]-2-hydroxy-2-cyclohexyl-2-phenylacetamide instead of (1α, 5α6α)-N-[3-azabicyclo[3.1.0]-hex-6-yl]-2-hydroxy-2-cyclopentyl-2-phenylacetamide and 1-bromo-3-methylbutane instead of 2-cyanobenzyl bromide.

$^1$HNMR (CDCl$_3$, δ-values): 7.59-7.56 (m, 2ArH), 7.35-7.22 (m, 3ArH), 6.56 (bs, 1H), 3.07 (t, 2H), 2.85-2.80 (m, 2H), 2.35-2.25 (m, 5H), 1.66-1.62 (m, 1H), 1.41-1.16 (m, 12H), 0.91-0.88 (m, 2H), 0.83 (d, 6H, J=6.0 Hz) IR (DCM): 1655 cm$^{-1}$

EXAMPLE 71

Preparation of (1α, 5α, 6α)-N-[3-(4-hydroxymethylphenethyl)-3-azabicyclo [3.1.0]-hex-6-yl]-2-hydroxy-2-cyclopentyl-2-phenylacetamide (Compound No.71)

Step-a: Synthesis of 4-hydroxymethylphenethyl chloride

The compound was prepared following the procedure given in U.S. Pat. No.4,595,690.

Step-b: The title compound was synthesized following the procedure of Example 10, using 4-hydroxy methylphenethylchloride instead of 3,5-dimethoxybenzylchloride $^1$HNMR (CDCl$_3$): 7.58-7.56 (m, 2ArH), 7.36-7.24 (m, 5H), 7.16-7.13 (d, 2H), 6.40 (bs, 1H), 4.64 (s, 2H), 3.17-3.10 (m, 3H), 3.02-2.97 (m, 1H), 2.84 (bs, 1H), 2.67-2.62 (m, 4H), 2.41 (bs, 2H), 1.77-1.16 (m, 11H) IR (DCM): 1655 cm$^{-1}$

EXAMPLE 72

Preparation of (1α, 5α, 6α)-N-[3-(3-fluoro-4-aminobenzyl)-3-azabicyclo [3.1.0]-hex-6-yl]-2-hydroxy-2-cyclopentyl-2-phenylacetamide (Compound No.72)

Step-a: Synthesis of 4-tert butoxy carboxylamino-3-fluorobenzylbromide

The compound was synthesized following the procedure described in J. Med. Chem., 2000, 43(26), 5017-5029

Step-b: Synthesis of (1α, 5α, 6α)-N-[3-(3-fluoro-4-tert-butoxy)carbonylamino-3-fluorobenzyl)-3-azabicyclo[3.1.0]hex-6-yl]-2-hydroxy-2-cyclopentylphenylacetamide The compound was synthesized following the procedure of Example 10, using 4-tert-butoxycarbonylamino-3-fluorobenzylbromide instead of 3,5-dimethoxybenzylchloride Step-c: Synthesis of(1α, 5α, 6α)-N-[3-(3-fluoro-4-aminobenzyl)-3-azabicyclo [3.1.0]-hex-6-yl]-2-hydroxy-2-cyclopentyl-2-phenylacetamide The compound of Step-b was dissolved in EtOH and ethanolic hydrochloric acid (5 ml) was added to the RM. The RM was stirred overnight at RT. The RM was concentrated under reduced pressure to give the desired product.

$^1$HNMR (CDCl$_3$, δ-values): 7.58-7.55 (m, 2ArH), 7.35-7.55 (m, 2ArH), 7.35-7.22 (ml, 3ArH), 6.87-6.63 (m, 3ArH), 6.34 (bs, 1H), 3.62 (bs, 2H), 3.49 (b, 2H), 3.10 (bs, 1H), 3.04-2.95 (bs, 4H), 2.33-2.30 (m, 2H), 1.63-0.88 (m, 10H) IR (DCM): 1640 cm$^{-1}$

EXAMPLE 73

Preparation of (1α, 5α, 6α)-N-[3-[1-(3,4-dimethylphenyl)ethyl]-3-azabicyclo [3.1.0]-hex-6-yl]-2-hydroxy-2-cyclopentyl-2-phenylacetamide (Compound No.73)

The compound was synthesized following the procedure of Example 10, using 1-(3,4-dimethylphenyl)ethylbromide instead of 3,5-dimethoxybenzylchloride.
$^1$HMR (CDCl$_3$ δ-values): 7.63-6.92 (m, 8ArH), 6.34 (bs, 1H), 3.27-3.25 (q, 1H), 3.14-0.85 (m, 25H). IR (DCM): 1658 cm$^{-1}$

EXAMPLE 74

Preparation of (1α, 5α, 6α)-N-[3-[2-(3-methylphenoxy)ethyl]-3-azabicyclo[3.1.0]-hex-6-yl]-2-hydroxy-2-cyclopentyl-2-phenylacetamide (Compound No.74)

The compound was synthesized following the procedure of Example 10, using 2-(3-methylphenoxy)ethyl bromide instead of 3,5-dimethoxybenzylchloride.
$^1$HNMR (CDCl$_3$, δ-values): 7.58-6.64 (m, 9ArH), 6.37 (s, 1H), 3.97-3.93 (t, 2H), 3.18-1.17 (m, 21H). IR (DCM): 1658 cm$^{-1}$

EXAMPLE 75

Preparation of (1α, 5α, 6α)-N-[3-[3-(3-methylphenoxy)propyl]-3-azabicyclo[3.1.0]-hex-6-yl]-2-hydroxy-2-cyclopentyl-2-phenylacetamide (Compound No.75)

The compound was synthesized following the procedure of Example 10, using 3-(3-methylphenoxy)propylbromide instead of 3,5-dimethoxybenzylchloride.
$^1$HNMR (CDCl$_3$, δ-values): 7.58-6.65 (m, 9ArH), 6.35 (bs, 1H), 3.94-3.89 (t, 2H), 3.12-1.25 (m, 23H). IR (DCM): 1657 cm$^{-1}$

EXAMPLE 76

Preparation of (1α, 5α, 6α)-N-[3-(2-methylbenzyl)-3-azabicyclo[3.1.0]-hex-6-yl]-2-hydroxy-2-cyclopentyl-2-phenylacetamide (Compound No.76)

The compound was prepared following the procedure of Example 13, using 2-methylbenzaldehyde instead of 4-trifluoromethylbenzaldehyde.
$^1$HNMR (CDCl$_3$, δ-values): 7.58-7.08 (m, 9ArH), 6.35 (bs, 1H), 3.49 (s, 2H), 3.09-0.88 (m, 19H) IR (DCM): 1653 cm$^{-1}$

EXAMPLE 77

Preparation of (1α, 5α, 6α)-N-[3-(2-(2-methylphenyl)ethyl-3-azabicyclo[3.1.0]-hex-6-yl]-2-hydroxy-2-cyclopentyl-2-phenylacetamide (Compound No.77)

The compound was prepared following the procedure of Example 10, using 2-(2-methylphenyl)ethylbromide instead of 3,5-dimethoxybenzylchloride.
$^1$HNMR (CDCl$_3$, δ-values): 7.59-7.09 (m, 9ArH), 6.35 (bs, 1H), 3.19 (m, 10H), 2.27 (8, 3H), 160-1.25 (m, 10H) IR (CM): 1654 cm$^{-1}$

EXAMPLE 78

Preparation of (1α, 5α, 6α)-N-[3-(1,3-dioxolan-2-ylmethyl)-3-azabicyclo-[3.1.0]-hex-6-yl]-2-hydroxy-2-cyclopentyl-2-phenylacetamide (Compound No.78)

The compound was synthesized by following the procedure of Example 10, but using 2-bromomethyl-1,3-dioxolane instead of 3,5-dimethoxybenzylchloride.

$^1$HNMR (CDCl$_3$, δ-values): 7.57-7.22 (m, 5ArH), 6.39 (bs, 1H), 4.90 (t, 1H), 3.95-3.79 (m, 4H), 3.22-1.18 (m, 19H) IR (DCM): 1652 cm$^{-1}$

EXAMPLE 79

Preparation of (1α, 5α, 6α)-N-[3-2-(carboxy)propyl [3-azabicyclo-[3.1.0]-hex-6-yl]-2-hydroxy-2-cyclopentyl-2-phenylacetamide (Compound No.79)

The compound was synthesized by following the procedure of Example 62, using (1α, 5α6α)-N-[3-[2-(carboethoxy)propyl]-3-azabicyclo[3.1.0]hex-6-yl]-2-hydroxy-2-cyclopentyl-2-phenylacetamide instead of (1α, 5α, 6α)-N-[3-(4-carbomethoxy) benzyl-3-azabicyclo-[3.1.0]-hex-6-yl]-2-hydroxy-2-cyclopentyl-2-phenylacetamide.

m.pt: 91-95° C. $^1$HNMR (CDCl$_3$, δ-value): 7.68-7.17 (m, 5ArH), 3.57-2.68 (m, 10H), 1.88 (s, 3H), 1.47-0.83 (m, 9H). IR (KBr): 1627 cm$^{-1}$ and 1714 cm$^{-1}$

EXAMPLE 80

Preparation of (1α, 5α, 6α)-N-[3-(1-phenylethyl)-3-azabicyclo[3.1.0]-hex-6-yl]-2-hydroxy-2,2-diphenylacetamide (Compound No.80)

Step-a: Synthesis of (1α, 5α, 6α)-N-[3-benzyl-3-azabicyclo[3.1.0]-hex-6-yl]-2-hydroxy-2,2-diphenylacetamide The compound was synthesized by following the procedure of Example 1, using 2,2-diphenylacetic acid instead of 2-hydroxy-2-cyclopentyl-2-(4-methoxy)phenylacetic acid and (1α, 5α, 6α)-3-azabicyclo-[3.1.0]-hexane instead of (1α, 5α, 6α)-N-[3-[4-methyl-3-pentenyl]-6-amino-3-azabicyclo[-[3.1.0]hexane hydrochloride.

Step-b: Synthesis of (1α, 5α, 6α)-N-[3-azabicyclo-[3.1.0]-hex-6-yl]-2-hydroxy-2,2-diphenylacetamide The compound was synthesized following the procedure of Example 2, Step-c, using (1α, 5α, 6α)-N-[3-benzyl-3-azabicyclo-[3.1.0]-hex-6-yl]-2-hydroxy-2,2-diphenylacetamide instead of (1α, 5α, 6α)-N-[3-benzyl-3-azabicyclo [3.1.0]-hex-6-yl]-2-hydroxy-2-cyclohexyl-2-phenylacetamide.

Step-c: Preparation of (1α, 5α, 6α)-N-[3-(1-phenylethyl)-3-azabicyclo[3.1.0]-hex-6-yl]-2-hydroxy-2,2-diphenylacetamide A solution of (1α, 5α, 6α)-N-[3-azabicyclo [3.1.0]-hex-6-yl]-2-hydroxy-2,2-diphenylacetamide (1 mmol), 1-phenylethylbromide (1.2 mmol), potassium carbonate (2 mmol) and potassium iodide (2 mmol) in 10 ml of acetonitrile was refluxed for 8 hours. The reaction mixture was filtered and the filtrate was concentrated under reduced pressure. The crude compound was purified by column chromatography (100-200 mesh silicagel) eluting the compound with 60:40-EtOAc-hexane mixture.

m.pt: 70-73° C. $^1$HNMR (CDCl$_3$, δ-values): 7.40-7.16 (m, 15ArH), 6.27 (bs, 1H), 3.82 (s, 1H), 3.33-3.21 (m, 3H), 3.19-3.13 (d, 1H), 2.81-2.39 (m, 2H), 1.56-1.24 (m, 5H).

EXAMPLE 81

Preparation of (1α, 5α, 6α)-N-[3-(1-phenylethyl)-3-azabicyclo[3.1.0]-hex-6-yl]-2-hydroxy-2-cycloheptyl-2-phenylacetamide (Compound No.81)

Step-a: Synthesis of (1α, 5α, 6α)-N-[3-benzyl-3-azabicyclo[3.1.0]-hex-6-yl]-2-hydroxy-2-cycloheptyl-2-phenylacetamide The compound was synthesized following the procedure of Example 1 using 2-hydroxy-2-cycloheptyl-2-phenylacetic acid instead of 2-hydroxy-2-cyclopentyl-2-(4-methoxy)phenylacetic acid and (1α, 5α, 6α)-3-benzyl-3-azabicyclo-6-amino-[3.1.0]hexane instead of (1α, 5α, 6α)-N-[4-methyl-3-pentenyl)]-6-amino-3-azabicyclo[3.1.0]hexane hydrochloride.

Step-b: Synthesis of (1α,5═,6α)-N-[3-azabicyclo [3.1.0]-hex-6-yl]-2-hydroxy-2-cycloheptyl-2-phenylacetamide The compound was synthesized following the procedure of Example 2, Step-c, using (1α, 5α, 6α)-N-[3-benzyl-3-azabicyclo[3.1.0]-hex-6-yl]-2-hydroxy-2-cycloheptyl-2-phenylacetamide instead of (1α, 5α, 6α)-N-[3-benzyl-3-azabicyclo [3.1.0]-hex-6-yl]-2-hydroxy-2-cyclohexyl-2-phenylacetamide.

Step-c: Synthesis of (1α, 5α, 6α)-N-[3-(1-phenylethyl)-3-azabicyclo[3.1.0]-hex-6-yl]-2-hydroxy-2-cycloheptyl-2-phenylacetamide The compound was synthesized following the procedure of Example 80, Step-c, using (1α, 5α, 6α)-N-[3-azabicyclo [3.1.0]-hex-6-yl]-2-hydroxy-2-cycloheptyl-2-phenylacetamide instead of (1α, 5α, 6α)-N-[3-azabicyclo[3.1.0]-hex-6-yl]-2-hydroxy-2-hydroxy-2,2-diphenylacetamide.

$^1$HNMR (CDCl$_3$, δ-values): 7.60-7.14 (m, 10ArH), 6.54 (bs, 1H), 3.28-3.16 (m, 2H), 2.98 (s, 1H IR (DCM): 1652 cm$^{-1}$

EXAMPLE 82

Preparation of (1α, 5α, 6α)-N-[3-(2-(2,3-dihydrobenzofuran -5-yl)ethyl)-3-azabicyclo[3.1.0]-hex-6-yl]-2-hydroxy-2-cyclopropyl-2-phenylacetamide (Compound N The compound was synthesized following the procedure of Example 5, using (1α, 5α, 6α)-N-[3-azabicyclo[3.1.0]-hex-6-yl]-2-cyclopropyl-2-hydroxy-2-cyclophenylacetamide instead of (1α, 5α, 6α)-N-[3-azabicyclo[3.1.0]-hex-6-yl]-2-cyclopentyl-2-hydroxy-2-phenyl acetamide and 5-(2-bromoethyl)-2,3-dihydrobenzofuran instead of 4-methylpentylmethane sulphonate.

$^1$HNMR (CDCl$_3$, δ-values): 7.58-7.34 (m, 5ArH), 6.99 (bs, 1H), 6.88 (d, J=8Hz, 1H), 6.67 (d, J=8Hz, 1H), 6.03 (m, 1H), 4.54 (t, 2H), 3.15 (m, 4H), 2.59-2.38 (m, 6H), 1.8 (m, 1H), 1.47 (m, 2H), 0.28 (m, 1H), 0.56 (m, 4H) IR (DCM): 1665 cm$^{-1}$

EXAMPLE 83

Preparation of (1α, 5α, 6α)-N-[3-(1-phenylethyl-3-azabicyclo[3.1.0]-hex-6-yl]-2-hydroxy-2-cyclopropyl-2-phenylacetamide (Compound No.83)

The compound was synthesized following the procedure of Example 5 using (1α, 5α, 6α)-N-[3-azabicyclo[3.1.0]-hex-6-yl]-2-hydroxy-2-cyclopropyl-2-phenylacetamide instead of (1α, 5α, 6α)-N-[3-azabicyclo[3.1.0]-hex-6-yl]-2-cyclopropyl-2-hydroxy-2-phenylacetamide and 1-phenyl ethyl bromide instead of 4-methylpentylmethane sulphonate.

$^1$HNMR (CDCl$_3$, δ-values): 7.58 (m, 2H), 7.38-7.17 (m, 8H), 5.99 (bs, 1H), 3.40 (d, J=3.0, 1H), 3.31 (m, 1H), 3.20 (q, J=6.5, 1H), 3.06 (m, 1H), 2.78 (m, 1H), 2.4 (m, 1H), 2.15 (m, 1H), 1.50 (m, 2H), 1.4(m, 1H), 1.25 (d, J=6.5, 3H), 0.56 (m, 4H) IR (KBr): 1655 cm$^{-1}$

EXAMPLE 84

Preparation of (1α, 5α, 6α)-N-[3-(1-phenylethyl)-3-azabicyclo[3.1.0]-hex-6-yl]-2-hydroxy-2-cyclobutyl-2-phenylacetamide (Compound No.84)

The compound was synthesized following the procedure of Example 80, Step-c using (1α, 5α, 6α)-N-[3-azabicyclo[3.1.0]-hex-6-yl]-2-hydroxy-2-cyclobutyl-2-phenylacetamide instead of (1α, 5α, 6α)-N-[3-azabicyclo[3.1.0]-hex-6-yl]-2-hydroxy-2,2-diphenyl acetamide.

$^1$HMR (CDCl$_3$, δ-values): 7.46-7.15 (m, 10ArH), 6.15 (m, 1H), 3.28 (m, 2H), 3.19 (q, J=6.5; 1H), 2.98 (m, 1H), 2.76 (m, 1H), 2.4 (m, 1H), 2.15-1.8 (m, 3H), 1.42 (m, 1H), 1.28 (m, 8H). IR (DCM): 1655 cm$^{-1}$

EXAMPLE 85

Preparation of (1α, 5α, 6α)-N-[3-(2-phenylcarboxyethyl)-3-azabicyclo[3.1.0]-hex-6-yl]-2-hydroxy-2-cycloheptyl-2-phenylacetamide (Compound No.85)

The compound was prepared following the procedure of Example 63 using (1α, 5α, 6α)-N-[3-(2-phenylcarboxyethyl)-3 azabicyclo[3.1.0]hex-6-yl]-2-hydroxy-2-cycloheptyl-2-phenylacetamide.

$^1$HNMR (DMSO d$_6$, δ-values): 7.68-7.18 (m, 10ArH), 5.75 (s, 1H), 3.35-2.59 (m, 7H), 1.98 (m, 2H), 1.47-1.15 (m, 9H), IR (DCM): 1638 cm$^{-1}$

EXAMPLE 86

Preparation of (1α, 5α, 6α)-N-[3-(2-(3-indoyl)ethyl-3-azabicyclo[3.1.0]-hex-6-yl]-2-hydroxy-2-cyclohexyl-2-phenylacetamide (Compound No.86)

The compound was synthesized following the procedure of Example 53 using (1α, 5α, 6α)-N-[3-azabicyclo[3.1.0]-hex-6-yl]-2-cyclohexyl-2-phenylacetamide instead of (1α, 5α, 6α)-N-[3-azabicyclo[3.1.0]-hex-6-yl]-2-hydroxy-2-cyclopentyl-2-phenylacetamide and 3-(2-bromomethyl)indole instead of 2-cyanobenzyl bromide.

$^1$HNMR (CDCl$_3$, δ-values): 7.96 (m, 1H0, 7.60-7.01 (m, 10ArH), 6.60 (bs, 1H) 3.20 (t, 2H), 2.95-2.68 (m, 6H), 2.39 (m, 3H), 1.32-1.12 (m, 10H), 0.87-0.85 (m, 2H) IR (DCM): 1662 cm$^{-1}$

EXAMPLE 87

Preparation of (1α, 5α, 6α)-N-[3-(2-methylnaphthyl-3-azabicyclo[3.1.0]-hex-6-yl]-2-hydroxy-2-cyclohexyl-2-phenylacetamide (Compound No.87)

The compound was synthesized following the procedure of Example 54 using (1α, 5α, 6α)-N-[3-azabicyclo[3.1.0]-hex-6-yl]-2-hydroxy-2-cyclohexyl-2-phenylacetamide instead of (1α, 5α, 6α)-N-[3-azabicyclo[3.1.0]-hex-6-yl]-2-hydroxy-2-cyclopentyl-2-phenylacetamide and 2-(bromomethyl) naphthalene instead of 2-cyanobenzyl bromide.

m.pt.: 165-168° C. $^1$HNMR (CDCl$_3$ δ-values): 7.78-7.72 (m, 3ArH), 7.63-7.57 (m, 3ArH), 7.44-7.31 (m, 6H), 6.59 (bs, 1H), 3.69 (s, 2H), 3.12-3.04 (m, 3H), 2.72 (m, 1H), 2.40(m, 3H), 1.82-1.78 (m, 1H), 1.66-1.54 (m, 2H), 1.45-1.12 (m, 8H), 0.88-0.84 (m, 1H) IR (KBr): 1653 cm$^{-1}$

EXAMPLE 88

Preparation of (1α, 5α, 6α)-N-[3-(2-indol-3-yl) ethyl)-3-azabicyclo[3.1.0]-hex-6-yl]-2-hydroxy-2-cyclopentyl-2-phenylacetamide (Compound No.88)

The compound was synthesized following the procedure of Example 54 using 3-(2-bromoethyl)indole instead of 2-cyanobenzyl bromide.

m.pt.: 55-57° C. $^1$HNMR (CDCl$_3$, δ-values): 8.07-8.01 (m, 1H), 7.65-7.60 (m, 3ArH), 7.42-7.05 (m, 7H), 6.44 (bs, 1H), 2.96-2.87 (m, 5H), 2.78-2.76 (m, 2H), 2.47-2.43 (m, 2H), 1.75-1.73 (m, 4H), 1.71-1.53 (m, 4H), 1.04 (m, 1H), 0.95 (m, 1H), IR (KBr): 1668 cm$^{-1}$

EXAMPLE 89

Preparation of (1α, 5α, 6α)-N-[3-hexyl-3-azabicyclo[3.1.0]-hex-6-yl]-2-hydroxy-2-cyclopentyl-2-phenylacetamide (Compound No.89)

The compound was synthesized using the procedure described in Example 54 using 1-bromohexane instead of 2-cyanobenzyl bromide.

$^1$HNMR (CDCl$_3$, δ-values): 7.58-7.56 (m, 2ArH), 7.36-7.26 (m, 3ArH), 6.31 (bs, 1H), 3.14-2.86 (m, 5H), 2.33-2.25 (m, 4H), 1.61-1.22 (m, 18H), 0.86 (t, 3H) IR (DCM): 1653 cm$^{-1}$

EXAMPLE 90

Preparation of (1α, 5α, 6α)-N-[3-(1,2,3,4-tetrahydronaphth-1-yl)-3-azabicyclo[3.1.0]-hex-6-yl]-2-hydroxy-2-cyclopentyl-2-phenylacetamide (Compound No.90)

The compound was synthesized following the procedure of Example 46 using 1,2,3,4-tetrahydro-1-naphthylbromide instead of 1-bromoindan.

m.pt.: 66-71° C. $^1$HNMR (CDCl$_3$, δ-values): 7.62-7.03 (m, 9ArH), 6.37 (bs, 1H), 3.66 (bs, 1H), 3.18-2.72 (m, 9H), 2.08-1.29 (m, 13H) IR (KBr): 1657 cm$^{-1}$

EXAMPLE 91

Preparation of (1α, 5α, 6α)-N-[3-(2-chlorobenzyl)-3-azabicyclo[3.1.0]-hex-6-yl]-2-hydroxy-2-cyclopentyl-2-phenylacetamide (Compound No.91)

The compound was synthesized following the procedure of Example 10, using 2-chlorobenzyl bromide instead of 3,5-dimethoxybenzyl bromide.

$^1$HNMR (CDCl$_3$, δ-values): 7.58-7.12 (m, 9ArH), 6.38 (s, 1H), 3.65 (s, 2H), 3.12-1.10 (m, 16H), IR (KBr): 1658 cm$^{-1}$

EXAMPLE 92

Preparation of (1α, 5α, 6α)-N-[3-(2-(2-methoxyphenyl)ethyl)-3-azabicyclo[3.1.0]-hex-6-yl]-2-hydroxy-2-cyclopentyl-2-phenylacetamide (Compound No.92)

The compound was synthesized following the procedure of Example 10, using 2-methoxyphenethyl bromide instead of 3,5-dimethoxybenzylbromide.

$^1$HNMR (CDCl$_3$, δ-values): 7.58-6.79(m, 9ArH), 6.31 (bs, 1H), 3.77 (s, 3H), 3.16-2.35 (m, 10H), 1.65-1.41 (m, 10H) IR (KBr): 1659 cm$^{-1}$

EXAMPLE 93

Preparation of (1α, 5α, 6α)-N-[3-(2-(4-fluorophenyl)ethyl]-3-azabicyclo[3.1.0]-hex-6-yl]-2-hydroxy-2-cyclopentyl-2-phenylacetamide (Compound No.93)

The compound was synthesized following the procedure of Example 10, using 2-(4-fluorophenyl)ethyl bromide instead of 3,5-dimethoxybenzylchloride.

$^1$HNMR (CDCl$_3$, δ-values): 7.59-6.89 (m, 9ArH), 6.37 (bs, 1H), 3.15-2.33 (m, 11H), 1.64-1.18 (m, 10H) IR (DCM): 1654 cm$^{-1}$

EXAMPLE 94

Preparation of (1α, 5α, 6α)-N-[3-[1-(indan-5-yl)ethyl-3-azabicyclo[3.1.0]-hex-6-yl]-2-hydroxy-2-cyclopentyl-2-phenylacetamide (Compound No.94)

The compound was synthesized following the procedure of Example 10, using 5-(1-bromoethyl)indane instead of 3,5-dimethoxybenzylchloride.

$^1$HNMR (CDCl$_3$, δ-values): 7.56-6.93 (m, 8ArH), 6.30 (bs, 1H), 3.27-2.76 (m, 11H), 2.05-1.20 (m, 15H)

EXAMPLE 95

Preparation of (1α, 5α, 6α)-N-[3-[1-(naphth-1-yl)ethyl]-3-azabicyclo[3.1.0]-hex-6-yl]-2-hydroxy-2-cyclopentyl-2-phenylacetamide (Compound No.95)

The compound was synthesized following the procedure of Example 10, using 1-(1-bromoethyl)naphthalene instead of 3,5-dimethoxybenzyl chloride.

m.pt: 82-87° C. $^1$HNMR (CDCl$_3$, δ-values): 8.36-7.25 (m, 12ArH), 3.95-3.93 (q, 1H), 3.43-2.04 (m, 7H), 1.57-1.23 (m, 13H) IR (KBr): 1654 cm$^{-1}$

EXAMPLE 96

Preparation of (1α, 5α, 6α)-N-[3-[1-(3,4-methylene dioxyphenyl)ethyl]-3-azabicyclo[3.1.0]-hex-6-yl]-2-hydroxy-2-cyclopentyl-2-phenylacetamide (Compound No.96)

The compound was synthesized following the procedure of Example 10, using 1-(1-bromoethyl)3,4-methylene dioxyphenyl instead of 3,5-dimethoxybenzyl chloride.

m.pt: 53-56° C. $^1$HNMR (CDCl$_3$, δ-values): 7.62-6.37 (m, 8ArH), 5.94 (m, 2H), 3.30-2.39 (m, 7H), 1.65-1.23 (m, 13H) IR (KBr): 1655 cm$^{-1}$

EXAMPLE 97

Preparation of (1α, 5α, 6α)-N-[3-[1-(1,2,3,4-tetrahydronaphth-6-yl)ethyl-3-azabicyclo[3.1.0]-hex-6-yl]-2-hydroxy-2-cyclopentyl-2-phenylacetamide (Compound No.97)

The compound was synthesized following the procedure of Example 10, using 1-(1-bromoethyl)1,2,3,4-tetrahydronaphthalene instead of 3,5-dimethoxybenzyl chloride.

m.pt: 73-78° C. $^1$HNMR (CDCl$_3$, δ-values): 7.60-6.89 (m, 8ArH), 6.33 (s, 1H), 3.28-2.73 (m, 9H), 2.37 (q, 1H), 2.02-1.58 (m, 14H), 1.27-1.12 (m, 5H) IR (KBr): 1654.8 cm$^{-1}$

EXAMPLE 98

Preparation of (1α, 5α, 6α)-N-[3-[1-(cis-(hex-3-enyl)]-3-azabicyclo[3.1.0]-hex-6-yl]-2-hydroxy-2-cyclopropyl-2-phenylacetamide (Compound No.98)

The compound was synthesized following the procedure of Example 10 using (1α, 5α, 6α)-N-[3-azabicyclo[3.1.0]-hex-6-yl]-2-hydroxy-2-cyclopropyl-2-phenylacetamide instead of (1α,5α,6α)-N-[3-azabicyclo[3.1.0]-hex-6-yl]-2-hydroxy-2-cyclopentyl-2-phenylacetamide and cis-3-hexen-1-methanesulphonate instead of 3,5-dimethoxybenzyl chloride.

$^1$HNMR (CDCl$_3$, δ-values): 7.59-7.26 (m, 5ArH), 6.0 (bs, 1H), 5.38-5.26 (m, 2H), 3.15-2.93 (m, 2H), 2.83 (s, 1H), 2.37-2.32 (m, 9H), 2.13-2.11 (m, 2H), 2.04-2.01 (m, 2H), 1.45-1.25 (m, 2H), 0.97-0.92 (m, 3H), 0.058-0.052 (m, 5H) IR (DCM): 1652 cm$^{-1}$

EXAMPLE 99

Preparation of (1α, 5α, 6α)-N-[3-[1-(trans hex-3-enyl)]-3-azabicyclo[3.1.0]-hex-6-yl]-2-hydroxy-2-cyclopropyl-2-phenylacetamide (Compound No.99)

The compound was synthesized following the procedure of Example 10 using (1α, 5α, 6α)-N-[3-azabicyclo[3.1.0]-hex-6-yl]-2-hydroxy-2-cyclopropyl-2-phenylacetamide instead of (1α, 5α, 6α)-N-[3-azabicyclo[3.1.0]-hex-6-yl]-2-hydroxy-2-cyclopentyl-2-phenylacetamide and trans-3-hexen-1-methane sulphonate instead of 3,5-dimethoxybenzyl chloride.

$^1$HNMR (CDCl$_3$, δ-values): 7.62-7.33 (m, 5ArH), 6.04 (bs, 1H), 5.55-5.33 (m, 2H), 3.15-2.93 (m, 2H), 2.83 (s, 1H), 2.37-2.32 (m, 9H), 2.13-2.11 (m, 2H), 2.04-2.01 (m, 2H), 1.45-1.25 (m, 2H), 0.97-0.92 (m, 3H), 0.058-0.052 (m, 5H) IR (DCM): 1652 cm$^{-1}$

EXAMPLE 100

Preparation of (1α, 5α, 6α)-N-[3-(1-(trans hex-3-enyl)]-3-azabicyclo[3.1.0]-2-hydroxy-2-cyclohexyl-2-phenylacetamide (Compound No.100)

The compound was synthesized following the procedure of Example 10 using (1α, 5α, 6α)-N-[3-azabicyclo[3.1.0]-hex-6-yl]-2-hydroxy-2-cyclohexyl-2-phenylacetamide instead of (1α, 5α, 6α)-N-[3-azabicyclo[3.1.0]-hex-6-yl]-2-hydroxy-2-cyclopentyl-2-phenylacetamide and trans-3-hexen-1-methanesulphonate instead of 3,5-dimethoxybenzyl chloride.

$^1$HNMR (CDCl$_3$, δ-values): 7.59-7.23 (m, 5ArH), 6.59 (bs, 1H), 5.45-5.30 (m, 2H), 3.11-3.08 (m, 2H), 2.39-2.36 (m, 3H), 3.11-3.08 (m, 2H), 2.86 (s, 1H), 2.39-2.36 (m, 3H), 2.06-1.97 (m, 6H), 1;45-1.22 (m, 13H), 0.96-0.89 (m, 2H) IR (DCM): 1652 cm$^{-1}$

EXAMPLE 101

Preparation of (1α, 5α, 6α)-N-[3-(1-(cis hex-3-enyl)]-3-azabicyclo[3.1.0]-2-hydroxy-2-cyclohexyl-2-phenylacetamide (Compound No.101)

The compound was synthesized following the procedure of Example 10 using cis-3-hexene-1-methanesulphonate instead of 3,5-dimethoxybenzyl chloride and (1α, 5α, 6α)-N-[3-azabicyclo[3.1.0]-hex-6-yl]-2-hydroxy-2-cyclohexyl-2-phenylacetamide instead of (1α, 5α, 6α)-N-[3-azabicyclo[3.1.0]-hex-6-yl]-2-hydroxy-2-cyclopentyl-2-phenylacetamide.

$^1$NMR (CDCl$_3$, δ-values): 7.59-7.23 (m, 5ArH), 6.58 (bs, 1H), 5.38-5.23 (m, 2H), 3.10-3.07 (m, 2H), 2.8 (s, 1H), 2.39-2.34 (m, 4H), 2.13-2.01 (m, 5H), 1.66-1.42 9m, 10H), 1.26-0.89 (m, 5H). IR (DCM): 1651 cm$^{-1}$

EXAMPLE 102

Preparation of (1α, 5α, 6α)-N-[3-(1-(trans-hex-3-enyl)]-3-azabicyclo[3.1.0]hex-6-yl]-2-hydroxy-2-cyclopentyl-2-phenylacetamide (Compound No.102)

The compound was synthesized following the procedure of Example 10 using trans-hex-3-ene-1-methane sulphonate instead of 3,5-dimethoxybenzyl chloride.

$^1$HNMR (CDCl$_3$, δ-values): 7.63-7.23 (m, 10ArH), 6.11 (bs, 1H), 3.56 (m, 2H), 3.41 (bs, 1H), 3.14-3.10 (m, 2H), 2.93-2.90 (m, 2H), 2.30-2.04 (m, 2H), 1.59-1.42 (m, 3H), 1.42-1.37 (m, 1H), 1.25 (s, 2H), 0.67-0.47 (m, 5H).

EXAMPLE 103

Preparation of (1α, 5α, 6α)-N-[3-(1-(cis hex-3-enyl)]-3-azabicyclo[3.1.0]-hex-6-yl]-2-hydroxy-2-cyclopentyl-2-phenylacetamide (Compound No.103)

The compound was synthesized following the procedure of Example 10 using cis-hex-3-ene-1-methanesulphonate instead of 3,5-dimethoxybenzyl chloride.

$^1$HNMR (CDCl$_3$, δ-values): 7.58-7.27 (m, 5ArH), 6.34 (bs, 1H), 5.40-5.22 (m, 2H), 3.4-3.0 (m, 4H), 2.84 (m, 1H), 2.33 (m, 4H), 2.12-1.98 (4H), 1.7-1.2 (m, 13H) IR (DCM): 1651 cm$^{-1}$

EXAMPLE 104

Preparation of (1α, 5α, 6α)-N-[3-(2-naphthylmethyl)-3-azabicyclo[3.1.0]-hex-6-yl]-2-hydroxy-2-cyclopentyl-2-phenylacetamide (Compound No.104)

The compound was synthesized following the procedure of Example 53 using 2-(bromomethyl)naphthalene instead of 2-cyanobenzylbromide.

m.pt.: 70-72° C. $^1$HNMR (CDCl$_3$, δ-values): 7.79-7.72 (m, 3ArH), 7.63-7.56 (m, 3ArH), 7.44-7.23 (m, 6ArH), 6.38 (bs, 1H), 3.69 (s, 2H), 3.11-2.98 (m, 5H), 2.41-2.38 (m, 2H), 1.69-1.43 (m, 8H), 1.28-1.11 (m,2H) IR (KBr): 1656 cm$^{-1}$

EXAMPLE 105

Preparation of (1α, 5α, 6α)-N-[3-(2-phenyl-1-methyl)-2-oxoethyl]-3-azabicyclo[3.1.0-hex-6-yl]-2-hydroxy-2-cyclopentyl-2-phenylacetamide (Compound No.105)

The compound was synthesized following the procedure of Example 53 using 2-(bromompropiophenone) instead of 2-cyanobenzyl bromide.

m.pt.: 57-59° C. $^1$HNMR (CDCl$_3$, δ-values): 8.04-8.01 (m, 2ArH), 7.60-7.22 (m, 8ArH), 6.39 (bs, 1H), 3.98 (q, 1H), 3.09-2.92 (m, 4H), 2.73-2.55 (m, 3H), 1.79-1.41 (m, 8), 1.25-1.10 (m, 5H). IR (Br): 1658 cm$^{-1}$

EXAMPLE 106

Preparation of (1α, 5α, 6α)-N-[3-(2-(4-carbamoylphenyl)ethyl)-3-azabicyclo[3.1.0]-hex-6-yl]-2-hydroxy-2-cyclopentyl-2-phenylacetamide (Compound No.106)

The compound was synthesized following the procedure of Example 10, using 4-carbamoyl phenethylbromide instead of 3,5-dimethoxybenzyl chloride.

$^1$HNMR (CDCl$_3$, δ-values): 7.70-7.67 (d, 2ArH), 7.52-7.41 (m, 2ArH), 7.35 (m, 1H), 7.22-6.86 (m, 3H), 3.01-2.98 (m, 1H), 2.72-2.58 (m, 7H), 1.55-0.78 (m, 10H). IR (KBr): 1659, 1618 cm$^{-1}$

EXAMPLE 107

Preparation of (1α, 5α, 6α)-N-[3-(2-(4-benzyloxycarbonylphenyl)ethyl)-3-azabicyclo[3.1.0]-hex-6-yl]-2-hydroxy-2-cyclopentyl-2-phenylacetamide (Compound No.107)

The compound was synthesized following the procedure of Example 10 using benzyl-4-(2-bromoethylbenzoate instead of 3,5-dimethoxybenzyl chloride.

$^1$HNMR (CDCl$_3$, δ-values): 7.96-7.93 (d, 2H), 7.55-7.51 (d, 2H), 7.44-7.19 (m, 10H), 6.39 (bs, 1H), 5.33 (s, 2H0, 3.16-2.98 (m, 4H), 2.82-2.62 (m, 5H),2.40-2.32 (s, 2H), 1.82-0.84 (m, 10H). IR (DCM): 1718, 1659 cm$^{-1}$

EXAMPLE 108

Preparation of (1α, 5α, 6α)-T-[3-(1-(2-methylpropyl)benzane-3-azabicyclo[3.1.0]-hex-6-yl]-2-hydroxy-2-cyclopentyl-2-phenylacetamide (Compound No.103)

The compound was synthesized by following the procedure described in Example 10 using (1-bromo-2-methylpropyl)benzene instead of 3,5-dimethoxybenzylchloride.

m.pt: 143-145° C. $^1$HNMR (CDCl$_3$, δ-values): 7.58-7.08 (m, 8ArH), 6.35 (bs, 1H), 3.16-2.84 (m, 5H), 2.09-2.05 (m, 2H) 2.74-2.67 (m, 6H), 2.4 (m, 1H), 1.64-1.25 (m, 10H)

EXAMPLE 109

Preparation of (1α, 5α, 6α)-N-[3-[2-(phenyl-1-methyl)-2-oxoethyl-3-azabicyclo[3.1.0]-hex-6-yl]-2-hydroxy-2-cyclohexyl-2-phenylacetamide (Compound No.109)

The compound was synthesized following the procedure of Example 53, using (1α, 5α, 6α)-N-[3-azabicyclo[3.1.0]-hex-6-yl]-2-hydroxy-2-cyclohexyl-2-phenylacetamide instead of (1α, 5α, 6α)-N-[3-azabicyclo[3.1.0]-hex-6-yl]-2-hydroxy-2-cyclopentyl-2-phenylacetamide and 2-bromopropiophenone instead of 2-cyanobenzylbromide.

m.pt: 79-81° C. $^1$HNMR (CDCl$_3$, δ-values): 8.04-8.02 (m, 2ArH), 7.58-7.25 (m, 8ArH), 6.60 (bs, 1H), 3.98 (q, 1H), 3.08-3.04 (m, 1H), 2.94-2.90 (m, 1H), 2.73-2.56 (m, 5H), 1.68-1.64 (m, 1H), 1.59-1.10 (m, 13H), 0.99 (m, 1H) IR (KBr): 1674 cm$^{-1}$

EXAMPLE 110

Preparation of (1α, 5α, 6α)-N-[3-hexyl-3-azabicyclo[3.1.0]-hex-6-yl]-2-hydroxy-2-cyclohexyl-2-phenylacetamide (Compound No.110)

The compound was synthesized by following the procedure of Example 53 using (1α, 5α, 6α)-N-[3-azabicyclo[3.1.0]hex-6-yl]-2-cyclohexyl-2-hydroxy-2-phenylacetamide instead of (1α, 5α6α)-N-(3-azabicyclo-[3.1.0]-hex-6-yl]-2-hydroxy-2-cyclopentyl-2-phenylacetamide and 1-bromohexane instead of 2-cyanobenzyl bromide.

m.pt: 59-61° C. $^1$HNMR (CDCl$_3$, δ-values): 7.59-7.56 (m, 2ArH), 7.35-7.22 (m, 3ArH), 6.57 (bs, 1H), 3.09-3.04 (m, 2H), 2.85-2.77 (m, 2H), 2.37-2.26 (m, 5H), 1.64-1.11 (m, 18H), 0.87-0.83 (m, 4H) IR (KBr): 1655 cm$^{-1}$

EXAMPLE 111

Preparation of (1α, 5α, 6α)-N-[3-(2-(4-cyanophenyl)ethyl-3-azabicyclo[3.1.0]-hex-6-yl]-2-hydroxy-2-cyclopentyl-2-phenylacetamide (Compound No.111)

The compound was synthesized by following the procedure of Example 10, using 4-cyanophenyl bromide instead of 3,4-dimethoxybenzylchloride.

$^1$HNMR (CDCl$_3$, δ-values): 7.56 (m, 4H), 7.33-7.26 (m, 5H), 6.53 (bs,1H), 3.63 (s, 1H), 3.24 (m, 2H), 3.01 (m, 2H), 2.85-2.74 (m, 3H0, 2.55 (m, 2H), 2.4 (m, 1H), 1.86-0.86 (m, 10H) IR (KBr): 1658 cm$^{-1}$ and 2228 cm$^{-1}$

EXAMPLE 112

Preparation of (1α, 5α6α)-N-[3-(2-(4-sulphamoylphenyl)ethyl)-3-azabicyclo[3.1.0]-hex-6-yl]-2-hydroxy-2-cyclopentyl-2-phenylacetamide (Compound 112)

The compound was synthesized by following the procedure of Example 10 using 4-sulphamoyl phenethylbromide instead of 3,5-dimethoxybenzyl chloride.

$^1$HNMR (CDCl$_3$, δ-values): 7.81-7.78 (m, 2H), 7.60-7.58 (m, 2H), 7.44-7.22 (m, 6H), 3.18-3.02 (m, 3H), 2.78-2.68 (m, 5H), 2.50 (bs, 2H), 2.4 (m, 1H), 1.61-0.86 (m, 10H) IR (KBr): 1656 cm$^{-1}$

EXAMPLE 113

Preparation of (1α, 5α, 6α)-N-[3-cyclohexylmethyl-3-azabicyclo[3.1.0]-hex-6-yl]-2-hydroxy-2-cyclopentyl-2-phenylacetamide (Compound No.113)

The compound was synthesized by following the procedure of Example 10 cyclohexylmethyl methane sulphonate instead of 3,5-dimethoxybenzylchloride.

$^1$HNMR (CDCl$_3$, δ-values): 7.58-7.14 (m, 5H), 6.35 (s, 1H), 3.38-2.88 (m, 5H), 2.25-1.78 (m, 4H), 1.7-1.1 (m, 20H) IR (DCM): 1645 cm$^{-1}$

EXAMPLE 114

Preparation of (1α, 5α, 6α)-N-[3-benzyl-3-azabicyclo[3.1.0]-hex-6-yl]-2,2-diphenylacetamide (Compound No.114)

A solution of diphenylacetic acid (1 mmol) and (1α, 5α, 6α)-3-benzyl-3-azabicyclo[3.1.0]-6-amino hexane (1.1 mmol) in 5 ml of DMF was cooled to 0° C. HOBT (1.2 mmol) and NMM (1 mmol) were added to the reaction mixture and stirred for 30 min. at 0° C.EDC (1 mmol) was added to the reaction mixture and stirred for 1 hr. at 0° C. and then at room temperature overnight. The reaction mixture was poured into water and extracted with ethyl acetate. The organic layer was dried and concentrated under reduced pressure. The residue was purified by column chromatography (100-200 mesh silicagel) eluting the compound with 50:50 EtOAc-hexane mixture to give a yellow solid.

m.pt: 169° C. $^1$HNMR (CDCl$_3$, δ-values): 7.37-7.18 (m, 15ArH), 5.57 (bs, 1H), 4.83 (s, 1H), 3.54 (s, 2H), 3.08-2.93 (m, (3H), 2.37-2.35 (d, 2H), 1.28-1.24 (m, 2H) IR (KBr): 1648 cm$^{-1}$

EXAMPLE 115

Preparation of (1α, 5α, 6α)-N-[3-benzyl-3-azabicyclo[3.1.0]-hex-6-yl]-2-chloro-2-cyclohexyl-2-phenylacetamide (Compound No.115)

A solution of (1α, 5α, 6α)-3-benzyl-3-azabicyclo-6-amino[3.1.0]hexane (1 mmol) was dissolved in 5 ml of DCM and cooled to −20° C. A solution of 2-chloro-2-cyclohexyl-2-phenylacetylchloride (1.1 mmol) in DCM (5 ml) was added to the reaction mixture and the reaction mixture was stirred at the same temperature for half an hour. It was then warmed to room temperature for 15 minutes. Triethylamine (2 mmol) was added after cooling the reaction mixture to −20° C. The reaction mixture was stirred at the same temperature for 30 minutes, warmed to room temperature and stirred at room temperature for 2 hours. The reaction mixture was poured into water and extracted with DCM. The organic layer was dried, concentrated under reduced pressure and the residue purified by column chromatography (100-200 mesh size, silicagel) eluting the compound with 15:85 EtOAc-hexane mixture.

$^1$HNMR (CDCl$_3$, δ-values): 7.67-7.20 (m, 5ArH), 6.82 (s, 1H), 3.53 (s, 2H), 3.10-3.02 (m, 3H), 2.38-2.31 (m, 2H), 1.73-0.87 (m, 13H). IR (KBr): 1674 cm$^{-1}$

EXAMPLE 116

Preparation of (1α, 5α, 6α)-N-[3-benzyl-3-azabicyclo[3.1.0]-hex-6-yl]-2-cyclohexyl-1-2-phenylacetamide (Compound No.116)

Step-a: Synthesis of α-cyclohexylphenylacetonitrile

The compound was synthesized following the procedure described in Organic Synthesis Coll. Vol. 3 pg 220.

Step-b: Synthesis of α-cyclohexylphenylacetic acid

To a mixture of 7.5 ml each of conc. sulphuric acid, acetic acid and water, the compound of Step-a (10 mmol) was added and the reaction mixture was refluxed for 12 hours. The reaction mixture was poured into ice and extracted with dichloromethane. The organic layer was separated and concentrated under reduced pressure and purified by column chromatography.

Step-c: Synthesis of (1α, 5α, 6α)-N-[3-benzyl-3-azabicyclo[3.1.0]-hex-6-yl]-2-cyclohexyl-2-phenylacetamide The compound was synthesized following the procedure of Example 1 using α-cyclohexylphenylacetic acid instead of 2-hydroxy-2-cyclopentyl-2-(4-methoxy)phenylacetic acid and (1α, 5α, 6α)-N-[3-benzyl-6-amino-3-azabicyclo[3.1.0]hexane(1α, 5α6α)-N-[3-(4-methyl-3-pentenyl)]-6-amino-3-azabicyclo[3.1.0]-hexane hydrochloride.

$^1$HNMR (CDCl$_3$): 7.34-7.16 (m, 10ArH), 5.47 (bs, 1H), 3.60 (s, 2H), 3.08-2.98 (m, 3H), 2.76 (dm, 2H), 2.35 (m, 2H), 1.43-0.91 (m, 11H) IR (KBr): 1646 cm$^{-1}$

EXAMPLE 117

Preparation of (1α, 5α, 6α)-N-[3-benzyl-3-azabicyclo[3.1.0]-hex-6-yl]-2-hydroxy-2-phenylacetamide (Compound No.117)

(1α, 5α, 6α)-3-benzyl-3-azabicyclo-6-amino[3.1.0]-hexane (1 mmol) was dissolved in DMF (10 ml) and to it 2-hydroxy-2-phenylacetylchloride (1.2 mmol) was added followed by the addition of potassium carbonate (2 mmol) and potassium iodide (2 mmol). The reaction mixture was stirred at room temperature for 3 hours. The reaction mixture was poured into water and extracted with ethyl acetate. The organic layer was dried and the residue obtained after removal of solvents was purified by column chromatography (100-200 mesh size silicagel) eluting the compound with DCM.

m.pt. 81° C. $^1$HNMR (CDCl$_3$, δ-values): 7.41-7.21 (m, 10ArH), 6.69 (bs, 1H), 5.34 (s, 1H), 3.59 (s, 2H), 3.15-3.11 (m, 3H), 2.45-2.41 (m, 211), 1.62-1.55 (m, 2H) IR (KBr): 1666 cm$^{-1}$

EXAMPLE 118

Preparation of (1α, 5α, 6α)-N-[3-benzyl-3-azabicyclo[3.1.0]-hex-6-yl]-2-cyclopentyl-2-phenylacetamide (Compound No.118)

Step-a: Synthesis of α-cyclopentylphenylacetonitrile

The compound was synthesized following the procedure described in Organic Synthesis Coll. Vol. 3 pg. 220, using cyclopentylbromide instead of cyclohexylbromide.

Step-b: Synthesis of α-cyclopentylphenylacetic acid

The compound was synthesized following the procedure described of Example-116, step-b, using α-cyclopentylphenylacetonitrile instead of α-cyclohexylphenylacetonitrile.

Step-c: Synthesis of (1α, 5α, 6α)-N-[3-benzyl-3-azabicyclo[3.1.0-hex-6-yl-2-cyclopentyl-2-phenylacetamide The compound was synthesized following the procedure of Example-1, using α-cyclopentylphenylacetic acid instead of 2-hydroxy-2-cyclopentyl-2-(4-methoxy)phenylacetic acid and (1α, 5α, 6α)-3-benzyl-3-azabicyclo-6-amino[3.1.0]hexane instead of (1α, 5α, 6α)-N-[3-(4-methyl-3-pentenyl)]-6-amino-3-azabicyclo[3.1.0]hexanehydrochloride.

$^1$HNMR (CDCl$_3$, δ-value): 7.34-7.16 (m, 10 ArH), 5.42 (s, 1H), 3.64 (s, 2H), 3.08-2.86 (m, 4H), 2.35 (m, 2H), 1.68-1.19 (m, 8H), 0.88 (m, 2H). IR (DCM): 1644 cm$^{-1}$

EXAMPLE 119

Preparation of (1α, 5α, 6α)-N-[3-benzyl-3-azabicyclo[3.1.0]-hex-6-yl]-2-hydroxy-2-phenylpropionamide (Compound No.119)

The compound was synthesized following the procedure of Example-1 using 2-hydroxy-2-phenyl propionic acid instead of 2-hydroxy-2-cyclopentyl-2-(4-methoxy)phenyl acetic acid and (1α, 5α6α)-3-benzyl-3-azabicyclo-6-amino[3.1.0] hexane instead of (1α, 5α6α)-N-[3-(4-methyl-3-pentenyl)]-6-amino-3-azabicyclo[3.1.0]-hexane hydrochloride.

$^1$HNMR (CDCl$_3$, δ-value): 7.53-7.18 (m, 10 ArH), 6.35 (bs, 1H), 3.53 (s, 2H), 3.07-3.04 (m, 3H), 2.38-2.33 (m, 2H), 1.78 (s, 3H), 0.970-0.85 (m, 2H) IR (DCM): 1659 cm$^{-1}$

EXAMPLE 120

Preparation of N-methyl-N-(1α, 5α, 6α)-N-[3-(1-phenyl ethyl)-3-azabicyclo[3.1.0]-hex-6-yl]-2-cyclopentyl-2-hydroxy-2-phenylacetamide (Compound No.120)

Step-a: Preparation of N-(1-tert-Butoxycarbonyl (1α, 5α, 6α)-N-[3-azabicyclo[3.1.0]-hex-6-yl]-2-hydroxy-2-cyclopentyl-2-phenylacetamide To a cold solution of 1 gm (1 mmol) of (1α, 5α, 6α)-N-[3-pentyl-2-phenylacetamide in DCM (50 ml) were added 0.9 ml (2 mmol) of triethylamine and 0.6 ml, 1.2 mmol of Ditertbutyl dicarbonate diluted with DCM (2 ml) at 0° C. The reaction mixture was stirred at 0° C. for 20 minutes and then at room temperature for 2 hours. The reaction mixture was poured into water, and the organic layer was separated, dried over anhydrous $Na_2SO_4$ and concentrated under reduced pressure. The crude compound was purified by column chromatography and the desired product eluted with 30:70 EtOAC-Hexane.

m.pt: 69-75° C. $^1$HNMR ($CDCl_3$, δ-value): 7.23-7.50 (m, 5ArH), 6.59 (s, 1H), 3.67-3.64 (m, 2H), 3.35-3.31 (m, 2H), 2.96 (m, 1H), 2.94 (m, 1H), 1.66-1.45 (m, 8H), 1.40 (s, 9H), 1.26 (1.25 (m, 1H)

Step-b: Preparation of N-(1-tert-Butyloxycarbonyl-(1α, 5α, 6α)-N-[3-azabicyclo[3.1.0]-hex-6-yl]-2-cyclopentyl-2-trimethylsilyloxy-2-phenylacetamide To a stirred solution of compound in step 120-a (960 mg, 1 mmol) and imidazole (604 mg, 3.7 mmol) in DMF (20 mg), was added trimethylsilylchloride (0.8 ml, 2.7 mmol) at room temperature and the reaction mixture was stirred for 18 hours. The reaction mixture was poured into water and extracted with diethylether. The organic layer was washed with $H_2O$, brine, and dried over anhydrous $Na_2SO_4$. The evaporation of solvent gave the crude product which was purified by silicagel column chromatography. The desired product was eluted with 10:90 -EtOAc-hexane mixture.

$^1$HNMR ($CDCl_3$, δ-value): 7.63-7.53 (m, 5 ArH), 7.30 (s, 1H), 4.02-3.98 (d, 2H), 3.66 (s, 2H), 3.24-3.13 (m, 1H), 2.74 (s, 1H), 2.11-1.84 (m, 8H), 1.69 (s, 9H), 1.38 (m, 1H), 1.15 (m, 1H), 0.214 (s, 9H).

Step-c: Preparation of N-methyl-N-(1-tert-butoxycarbonyl (1α, 5α, 6α)-N-[3-azabicyclo[3.1.0]-hex-6-yl]-2-hydroxy-2-cyclopentyl-2-phenylacetamide To a stirred solution of compound synthesized in step-120b (825 mg, 1 mmol) in dry THF (15 ml), were sequentially added sodium hydride (556 ml, 152 mg, 1.8 mmol), and tetrabutyl ammonium iodide (50 mg, 0.07 mmol) at 0° C. After 10 minutes, iodomethane was added. The mixture was allowed to warm to room temperature and stirred for 19 hours. The reaction mixture was quenched with saturated $NH_4Cl$ solution and the mixture was extracted with ethyl acetate. The organic layer was washed with brine, dried over anhydrous $Na_2SO_4$ and concentrated. The residue was purified by silica gel column chromatography and the desired product eluted with 8:92 EtOAc-Hexane mixture.

IR: 1699.1 $cm^{-1}$, 1651.9 $cm^{-1}$ $^1$HNMR ($CDCl_3$, δ-value): 7.29-7.23 (m, 5ArH), 3.7 (bs, 2H), 3.40 (bs, 2H), 2.76 (bs, 2H), 2.44 (s, 3H), 1.80-1.51 (m, 8H), 1.43 (s, 9H), 1.25 (m, 1H), 1.22 (m, 1H), 0.19 (s, 3H)

Step-d: Preparation of N-methyl(1α, 5α6α)-N-[3-azabicyclo[3.1.0]-hex-6-yl]-2-cyclopentyl-2-hydroxy-2-phenylacetamide hydrochloride The compound synthesized in step c (330 m, 1 mmol) was dissolved in 10% HCl—MeOH (8 ml) and the mixture was stirred for 17 hours at room temperature. The solvent was evaporated to obtain the crude compound which was used without purification.

IR: 1631.30 $cm^{-1}$ $^1$HNMR ($CDCl_3$, δ-value): 7.40-7.13 (m, 5ArH), 3.60 (bs, 2H), 3.42 (bs, 2H), 2.96 (bs, 2H), 2.75 (s, 3H), 2.00-1.55 (m, 8H), 1.32-1.25 (m, 2H).

Step-e: Preparation of N-methyl-N-(1α, 5α, 6α)-N-[3-(1-phenyl ethyl)-3-azabicyclo[3.1.0]-hex-6-yl]-2-cyclopentyl-2-hydroxy-2-phenylacetamide To a solution of compound of step-120d (230 mg, 1 mmol) in $CH_3CN$ (25 ml) were added potassium carbonate (226 mg, 3 mmol), 1-bromo-1-phenylethane (160 mg, 1.5 mmol) and potassium iodide (170 mg, 1.5 mmol) at room temperature. The reaction mixture was refluxed for 8 hours. The reaction mixture was extracted with EtOAc. The combined organic extract was dried over anhy. $Na_2SO_4$ and concentrated. The crude compound was purified by silica gel (100-200 mesh) column chromatography and the desired product was eluted with 20:80 EtOAc/Hexane mixture.

IR=1628 $cm^{-1}$ $^1$HNMR ($CDCl_3$, δ-value): 7.41-7.19 (m, 10ArH), 5.27 (s, 1H), 3.20-3.18 (m, 2H), 3.02-2.99 (m, 2H), 2.74-2.70 (m, 1H), 2.68 (s, 3H), 2.25 (m, 1H), 2.21 (m, 1H), 1.18-1.38 (m, 8H), 1.29 (s, 3H), 1.26 (m, 1H), 1.25 (s, 1H)

EXAMPLE 121

N-methyl-N-(1α, 5α, 6α)-N-[3-(3,4-methylenedioxyethyl)-3-azabicyclo[3.1.0]hex-6-yl]-2-cyclopentyl-2-hydroxy-2-phenylacetamide (Compound No.121)

This compound was synthesized following the same procedure as for Example 120, using 3,4-methylenedioxyphenyl ethyl bromide instead of 1-bromo-1-phenyl ethane. The desired product was eluted with 50:50 EtoAc-Hexane mixture.

IR (DCM): 1621.2 $cm^{-1}$ $^1$HMR ($CDCl_3$-δ-values): 7.39-7.21 (m, 5ArH), 6.74-6.60 (m, 3Ar—H), 5.92 (s, 2H), 5.17 (s, 1H), 3.14-3.01 (m, 4H), 2.71 (s, 3H), 2.60-2.58 (m, 4H), 2.33 (m, 2H), 1.79-1.38 (m, 10H).

EXAMPLE 122

Preparation of N-methyl-N-(1α, 5α6α)-N-[3-(1-benzyl)-3-azabicyclo[3.1.0]-hex-6-yl]-2-cyclopentyl-2-hydroxy-2-phenylacetamide (Compound No.122)

This compound was synthesized following the same method as for Example 120e, using benzyl bromide instead of 1-bromo-1-phenyl ethane. The desired product eluted with 50:50 EtoAc/Hexane mixture.

$^1$HNMR ($CDCl_3$, δ-value): 7.40-7.23 (m, 10ArH), 5.19 (s, 1H), 3.54 (s, 2H), 3.03 (m, 4H), 2.70 (s, 3H), 2.35 (m, 2H), 1.79-1.44 (m, 8H), 1.42 (m, 1H), 1.25 (m, 1H) IR=1627.8 $cm^{-1}$

EXAMPLE 123

Preparation of N-methyl(1α, 5α, 6α)-N-[3-(3,4-methylenedioxyethyl-3-azabicyclo[3.1.0]-hex-6-yl]-2-cyclohexyl-2-hydroxy-2-phenylacetamide (Compound No.123)

Step-a: Preparation of N-(1-tert-butoxycarbonyl(1α, 5α, 6α)-N-[3-azabicyclo[3.1.0]-hex-6-yl]-2-hydroxy-cyclohexyl-2-phenylacetamide This compound was synthesized following the same method as for Example 120, step a, by using (1α, 5α, 6α)-N-[3-(3-azabicyclo[3.1.0]-hex-6-yl]-2-hydroxy-2-cyclohexyl-2-phenylacetamide instead of (1α, 5α, 6α)-N-[3-azabicyclo[3.1.0]-hex-6-yl]-2-hydroxy -2-phenylacetamide.

m.pt: 93-97° C. ¹HNMR (CDCl₃, δ-values): 7.59-7.23 (m, 5ArH), 6.78 (s, 1H), 3.67-3.61 (m, 2H), 3.35-3.32 (m, 2H), 2.61 (s, 1H), 2.41-2.37 (m, 2H), 1.77-1.44 (m, 10H), 1.40 (s, 9H), 1.11 (m, 1H), 0.85 (m, 1H). IR: 1698.8 cm⁻¹ and 1676 cm⁻¹

Step-b: Preparation of N-(1-tert-butyloxycarbonyl (1α, 5α, 6α)-N-[3-azabicyclo[3.1.0]-hex-6-yl]-2-cyclohexyl-2-trimethylsilyloxy-2-phenylacetamide This compound was synthesized following the same procedure as for Example 120, step-b, using N-(1-tert-butyloxycarbonyl(1α, 5α, 6α)-N-[3-azabicyclo[3.1.0]-hex-6-yl]-2-cyclohexyl-2-hydroxy-2-phenyl acetamide instead of N-(t-tert-butyloxycarbonyl(1α, 5α, 6α)-N-[3-azabicyclo[3.1.0]-hex-6-yl]-2-cyclopenyl-2-trimethylsilyloxy-2-phenylacetamide.

m.pt: 62-66° C. ¹HNMR (CDCl₃, δ-value): 7.26-7.14 (m, 5ArH), 3.74-3.64 (m, 2H), 3.40 (bs, 2H), 2.37 (s, 3H), 2.30 (bs, 2H), 1.71-1.53 (m, 10H), 1.42 (s, 3H), 1.33-1.21 (m, 2H), 0.19 (s, 9H). IR: 1701.15 cm⁻¹ 1652.3 cm⁻¹

Step-c: N-methyl-N-(1-tert-butyloxy carbonyl 1α, 5α, 6α)-N-[3-azabicyclo[3.1.0]hex-6-yl]-2-cyclohexyl-2-trimethyl-silyloxy-2-phenylacetamide This compound was synthesized following the same procedure as for Example 120, step-c, using N-methyl-N-(1-tert-butyloxy carbonyl 1α, 5α, 6α)-N-[3-azabicyclo[3.1.0]hex-6-yl]-2-cyclohexyl-2-trimethyl-silyloxy-2-phenylacetamide instead of N-(1-tert-butyloxy carbonyl (1α, 5α, 6α)-N-[3-azabicyclo[3.1.0]hex-6-yl]-2-cyclohexyl-2-trimethylsilyloxy-2-phenylacetamide. The desired product eluted with 25:75 EtoAc/hexane mixture.

m.pt.: 62-66° C. ¹HNMR (CDCl₃-δ-values): 7.26-7.14 (m, 5ArH), 3.74-3.64 (m, 2H), 3.40 (bs, 2H), 2.37 (s, 3H), 2.30 (bs, 2H), 1.71-1.53 (m, 10H), 1.42 (s, 3), 1.33-1.21 (m, 2H), 0.19 (s, 9H). IR (KBr): 1701.5 cm⁻¹ and 1652.3 cm⁻¹

Step-d: Preparation of N-methyl(1α, 5α, 6α)-N-[3-azabicyclo[3.1.0]-hex-6-yl]-2-cyclohexyl-2-hydroxy-2-phenylacetamide hydrochloride This compound was synthesized following the same procedure as for Example 120, Step-d, by using N-methyl-N-(1-tert-butyloxy carbonyl (1α, 5α, 6α)-N-[3-azabicyclo[3.1.0]-hex-6-yl]-2-cyclohexyl-2-trimethylsilyloxy-2-phenylacetamide.

¹HNMR (CDCl₃, δ-value): 7.42-7.22 (m, 5ArH), 5.30 (s, 1H), 3.73-3.00 (m, 6H), 2.81 (s, 3H), 1.82-1.38 (m, 10H), 1.32-1.25 (m, 2H) IR: 1627.10 cm⁻¹

Step e: Preparation of N-methyl(1α, 5α, 6α)-N-[3-(3,4-methylenedioxyethyl-3-azabicyclo[3.1.0]-hex-6-yl]-2-cyclohexyl-2-hydroxy-2-phenylacetamide This compound was synthesized following the same procedure as for Example 120, using compound synthesized in step-123d and 3,4-methylenedioxyphenylethylbromide. The crude compound was purified by silicagel (100-200) column chromatography and the desired product was eluted with 40:60 EtoAc/Hexane.

¹HNMR (CDCl₃, δ-value): 7.41-7.21 (m, 5ArH), 6.74-6.61 (m, 3 ArH), 5.92 (s, 2H), 4.80 (s, 1H), 3.21-3.18 (m, 1H), 3.06-2.95 (m, 2H), 2.75 (s, 3H), 2.65-2.49 (m, 5H), 2.37-2.32 (t, 2H), 1.80-0.88 (m, 12H) IR (KBr) 1622.2 cm⁻¹

EXAMPLE 124

Preparation of N-methyl-N-(1α, 5α, 6α)-N-[3-(4-methyl-3-pentenyl)-3-azabicyclo[3.1.0]-hex-6-yl]-2-cyclohexyl-2-hydroxy-2-phenylacetamide (Compound No.124)

This compound was synthesized following the same procedure as for Example 123, using 5-bromo-2-methyl-2-pentene instead of 3,4-methylenedioxyphenylethylbromide.
Eluent=40% EtoAc/Hexane
¹HNMR (CDCl₃, δ-value): 7.43-7.21 (m, 5ArH), 5.12-5.07 (t, 1H), 4.87 (s, 1H), 3.39-3.36 (m, 1H), 3.18-2.98 (m, 2H), 2.75 (s, 3H), 2.50 (bs, 1H), 2.38-2.27 (m, 3H), 2.12-2.05 (m, 2H), 1.69-1.25 (m, 14H), 1.11 (s, 6H) IR: 1627.1 cm⁻¹

EXAMPLE 125

Preparation of N-methyl-N-(1α, 5α, 6α)-N-[3-(4-methyl-3-pentenyl)-3-azabicyclo[3.1.0]-hex-6-yl]-2-cyclopentyl-2-hydroxy-2-phenylacetamide (Compound No.125)

The compound was synthesized following the same procedure as for Example 120, using 5-bromo-2-methyl-2-pentene instead of 1-bromo-1-phenyl ethane.
¹HNMR (CDCl₃, δ-value): 7.40-7.21 (m, 5ArH), 5.21 (s, 1H), 5.09-5.05 (t, 1H), 3.12-3.09 (m, 2H), 2.95 (s, 1H), 2.71 (s, 3H), 2.37-2.32 (m, 3H), 2.09-2.07 (m, 2H0, 1.68 (s, 6H), 1.65-1.51 (m, 8H), 1.48-1.41 (m, 2H), 1.25 (m, 2H). IR: 1632.8 cm⁻¹, 1651.9 cm⁻¹

EXAMPLE 126

Preparation of N-methyl-N-(1α, 5α, 6α)-N-[3-(4-methyl-3-pentenyl)-3-azabicyclo[3.1.0]-hex-6-yl]-2-cyclopentyl-2-hydroxy-2-phenylacetamide L(+) Tartarate salt (Compound No.126)

To a solution of compound synthesized in Example 125 (485 mg, 1 mmol) in 8 ml of EtOH was added L (+) tartaric acid (184 mg, 1 mmol) and the reaction mixture heated at 60° C. for 1 hr. After 1 hour the reaction mixture was concentrated to give a solid compound.
mpt.: 71-75° C. IR (Kbi): 1735 cm⁻¹ and 1625.7 cm⁻¹
$_{HPLC}$: 98.60%

Biological Activity

Radioligand Binding Assays:

The affinity of test compounds for $M_2$ and $M_3$ muscarinic receptor subtypes was determined by [³H]—N-methylscopolamine binding studies using rat heart and submandibular gland respectively as described by Moriya et al., (*Life Sci.*, 1999,64(25):2351-2358) with minor modifications.

Membrane preparation: Submandibular glands and heart were isolated and placed in ice cold homogenizing buffer (HEPES 20 mM, 10 mM EDTA, pH 7.4) immediately after sacrifice. The tissues were homogenized in 10 volumes of homogenizing buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at −70° C. until the time of assay.

Ligand binding assay The compounds were dissolved and diluted in DMSO. The membrane homogenates (150-250 μg protein) were incubated in 250 μl of assay buffer (HEPES 20 mM, pH 7.4) at 24-25° C. for 3 h. Non-specific binding was determined in the-presence of 1 μM atropine. The incubation was terminated by vacuum filtration over GF/B fiber filters (Wallac). The filters were then washed with ice cold 50 mM Tris HCl buffer (pH 7.4). The filter mats were dried and bound radioactivity retained on filters was counted. The $IC_{50}$ & Kd were estimated by using the non-linear curve fitting program using G Pad Prism software. The value of inhibition constant Ki was calculated from competitive binding studies by using Cheng & Prusoff equation (*Biochem Pharmacol*, 1973,22: 3099-3108), $Ki=IC_{50}/(1+L/Kd)$, where L is the concentration of $[^3H]NMS$ used in the particular experiment.

Functional Experiments Using Isolated Rat Bladder:

Methodology:

Animals were euthanized by overdose of urethane and whole bladder was isolated and removed rapidly and placed in ice cold Tyrode buffer with the following composition (mMol/L) NaCl 137; KCl 2.7; $CaCl_2$ 1.8; $MgCl_2$ 0.1; $NaHCO_3$ 11.9; $NaH_2PO_4$ 0.4; Glucose 5:55 and continuously gassed with 95% $O_2$ and 5% $CO_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period the stabilization of the tissue contractile response was assessed with 1 μmol/L of Carbachol consecutively for 2-3 times. Subsequently a cumulative concentration response curve to carbachol (10-9 mol/L to $3\times10^{-5}$ mol/L) was obtained. After several washes, once the baseline was achieved, cumulative concentration response curve was obtained in presence of NCE (NCE added 20 min. prior to the second CRC).

The contractile results were expressed as % of control E max. ED50 values were calculated by fitting a non-linear regression curve (Graph Pad Prism). PKB values were calculated by the formula pKB=−log [(molar concentration of antagonist/(dose ratio−1))]

where, dose ratio=ED50 in the presence of antagonist/ED50 in the absence of antagonist.

The results of In-Vitro tests are listed in Table II.

TABLE II

| | Receptor Binding Assay pKi (nM) | | Functional Assay $pK_B$ |
|---|---|---|---|
| | $M_2$ | $M_3$ | (nM) |
| Compound No. 2 | 5.5 | 6.89 | 7.52 |
| Compound No. 3 | 5.4 | 6.28 | 8.04 |
| Compound No. 17 | 6.3 | 7.1 | 7.02 |
| Compound No. 19 | 5.58 | 6.11 | 7.52 |
| Compound No. 21 | 6.2 | 7.6 | 8.2 |
| Compound No. 43 | 5.91 | 7.23 | 6.86 |
| Compound No. 50 | 6.09 | 7.36 | 7.48 |
| Compound No. 58 | 6.81 | 8.23 | 7.89 |
| Compound No. 66 | 6.27 | 7.36 | 7.67 |
| Compound No. 71 | 6.01 | 7.37 | 6.8 |
| Compound No. 81 | 7.27 | 8.62 | 7.89 |
| Compound No. 115 | <6 | <6 | 5.45 |
| Compound No. 116 | <6 | <6 | 6.03 |
| Compound No. 117 | <6 | <6 | 5.08 |
| Compound No. 125 | 7.61 | 7.58 | 8.36 |

While the present invention has been described in terms of its specific embodiments, certain modifications and equivalents will be apparent to those skilled in the art and are intended to be included within the scope of the present invention.

We claim:

1. A compound having the structure of Formula I:

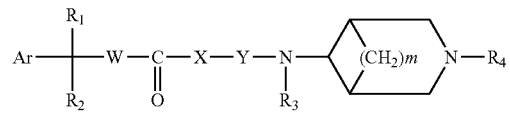

Formula I and its pharmaceutically acceptable salts, pharmaceutically acceptable, enantiomers, diastereomers, or N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), trifluoromethyl cyano, hydroxy, nitro, halogen (e.g. F, Cl, Br or I), lower alkoxy ($C_1$-$C_4$), amino or lower alkylamino($C_1$-$C_4$);

$R_1$ represents a hydrogen, hydroxy, hydroxymethyl, loweralkyl ($C_1$-$C_4$), amino, alkoxy, cycloalkyl ($C_3$-$C_7$), carbamoyl, halogen (e.g. F, Cl, Br, I) or aryl;

$R_2$ represents alkyl, $C_3$-$C_7$ cycloalkyl ring, $C_3$-$C_7$ cycloalkenyl ring, an aryl or a heteroaryl ring having 1 to 2 hetero atoms selected from the group consisting of oxygen, sulphur and nitrogen atoms; the aryl or a hetero aryl ring may be unsubstituted or substituted by one to three substituents independently selected from lower alkyl ($C_1$-$C_4$), trifluoromethyl, cyano, hydroxy, nitro, lower alkoxycarbonyl, halogen, lower alkoxy ($C_1$-$C_4$), unsubstituted amino or lower alkyl ($C_1$-$C_4$) amino;

W represents $(CH_2)_p$, where p represents 0 to 1;

X represents an oxygen, sulphur, NR or no atom wherein R represents hydrogen or $C_{1-6}$ alkyl;

Y represents $CHR_5CO$ wherein $R_5$ represents hydrogen or methyl, or $(CH_2)q$ wherein q represents 0 to 4;

m represents 0 to 2;

$R_3$ represents hydrogen, lower alkyl ($C_1$-$C_4$) or $CO_2C(CH_3)_3$; and $R_4$ represents $C_1$-$C_{15}$ saturated or unsaturated aliphatic hydrocarbon (straight chain or branched) in which any 1 to 6 hydrogen atoms may be substituted with the group independently selected from halogen (e.g. F, Cl, Br, I), carboxylic acid, carboxylic acid ester, aryl, aryloxy, arylalkyl, arylalkenyl, heteroaryl, heteroarylalkyl, heteroarylalkenyl having 1 to 2 hetero atoms selected from the group consisting of nitrogen, oxygen and sulphur with option that any 1 to 5 hydrogen atoms on the ring in said aryl, aryloxy, arylalkyl, arylalkenyl, heteroaryl, heteroarylalkenyl may be substituted with lower alkyl, trifluoromethyl, halogen (e.g. F, Cl, Br, I), cyano, nitro, hydroxy, lower ($C_1$-$C_4$) alkoxy, amino, lower ($C_1$-$C_4$) alkylamino, sulphonylamino, amide, carboxylic acid, carboxylic acid ester or benzyl ester.

2. The compound according to claim 1 having the structure of Formula II and its pharmaceutically acceptable salts, pharmaceutically acceptable enantiomers, diastereomers, or N-oxides, wherein Ar, $R_1$, $R_2$, $R_3$, $R_4$, W, X and Y are as defined for Formula I

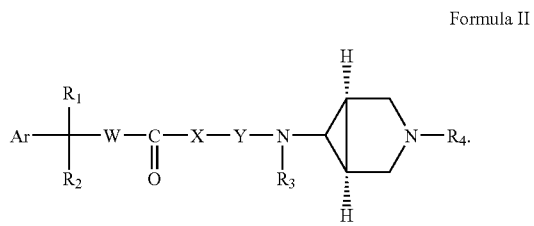

Formula II

3. The compound according to claim 1 having the structure of Formula III and its pharmaceutically acceptable salts, pharmaceutically acceptable enantiomers, diastereomers, or N-oxides, wherein Ar, $R_1$, $R_2$, $R_3$ and $R_4$ are as defined for Formula I

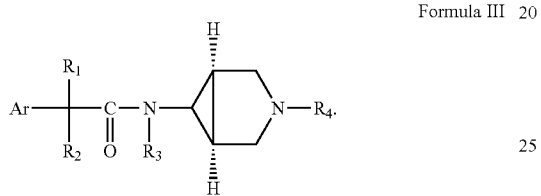

Formula III

4. The compound according to claim 1 having the structure of Formula IV and its pharmaceutically acceptable salts, pharmaceutically acceptable enantiomers, diastereomers, or N-oxides, wherein Ar, $R_1$, $R_3$ and $R_4$ are as defined for Formula I and r is 1 to 4

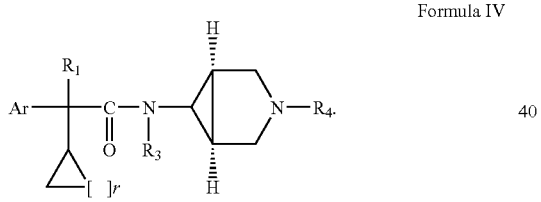

Formula IV

5. The compound according to claim 1 having the structure of Formula V and its pharmaceutically acceptable salts, pharmaceutically acceptable enantiomers, diastereomers, or N-oxides, wherein Ar, $R_1$, $R_3$ and $R_4$ are as defined for Formula I and s is 1 to 3

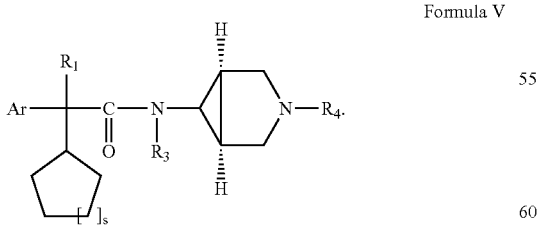

Formula V

6. The compound according to claim 1 having the structure of Formula VI and its pharmaceutically acceptable salts, pharmaceutically acceptable enantiomers, diastereomers, or N-oxides, wherein $R_3$, $R_4$ and s are as defined for Formula I and s is 1 to 3

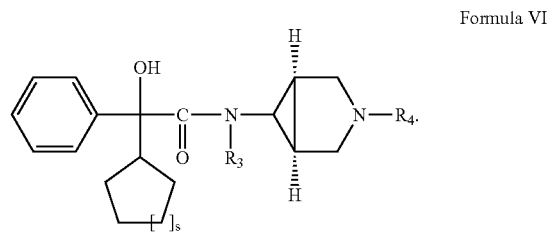

Formula VI

7. A compound selected from the group consisting of:
(1α,5α,6α)-N-[3-(4-methyl-3-pentenyl)-3-azabicyclo[3.1.0]hex-6-yl]-2-hydroxy-2-cyclopentyl-2-(4-methoxy)phenylacetamide;
(1α,5α,6α)-N-[3-(2-thienylmethyl)-3-azabicyclo[3.1.0]hex-6-yl]-2-hydroxy-2-cyclohexyl-2-phenylacetamide;
(1α,5α,6α)-N-[3-(2-thienylmethyl)-3-azabicyclo[3.1.0]hex-6-yl]-2-hydroxy-2-cyclopentyl-2-phenylacetamide;
(1α,5α,6α)-N-[3-(5-nitro-2-furylmethyl)-3-azabicyclo[3.1.0]hex-6-yl]-2-hydroxy-2-cyclopentyl-2-phenylacetamide;
(1α,5α,6α)-N-[3-(4-methyl-pentyl)-3-azabicyclo[3.1.0]hex-6-yl]-2-hydroxy-2-cyclopentyl-2-phenylacetamide;
(1α,5α,6α)-N-[3-(2-(1,4-benzodioxan-6-yl)ethyl)-3-azabicyclo[3.1.0]hex-6-yl]-2-hydroxy-2-cyclopentyl-2-phenylacetamide;
(1α,5α,6α)-N-[3-(3,4,5-trimethoxyphenethyl-3-azabicyclo[3.1.0]hex-6-yl]-2-hydroxy-2-cyclopentyl-2-phenylacetamide;
(1α,5α,6α)-N-[3-[3-(3,4-methyldioxyphenyl)propyl)]-3-azabicyclo[3.1.0]hex-6-yl]-2-hydroxy-2-cyclopentyl-2-phenylacetamide;
(1α,5α,6α)-N-[3-(3,4,5-trimethoxybenzyl)-3-azabicyclo[3.1.0]hex-6-yl]-2-hydroxy-2-cyclopentyl-2-phenylacetamide;
(1α, 5α6α)-N-[3-(3,5-dimethoxybenzyl)-3-azabicyclo[3.1.0]hex-6-yl]-2-hydroxy-2-cyclopentyl-2-phenylacetamide;
(1α, 5α6α)-N-[3-(3,4-dimethoxybenzyl)-3-azabicyclo[3.1.0]hex-6-yl]-2-hydroxy-2-cyclopentyl-2-phenylacetamide;
(1α,5α,6α)-N-[3-(3-methoxybenzyl)-3-azabicyclo[3.1.0]hex-6-yl]-2-hydroxy-2-cyclopentyl-2-phenylacetamide;
(1α,5α,6α)-N-[3-(4-trifluoromethylbenzyl)-3-azabicyclo[3. 10.]hex-6-yl]-2-hydroxy-2-cyclopentyl-2-phenylacetamide;
(1α,5α,6α)-N-[3-(5-methyl-2-furylmethyl)-3-azabicyclo[3.1.0]hex-6-yl]-2-hydroxy-2-cyclopentyl-2-phenylacetamide;
(1α,5α,6α)-N-[3-(2-(4-methylphenoxy)ethyl)-3-azabicyclo[3.1.0]hex-6-yl]-2-hydroxy-2-cyclopentyl-2-phenylacetamide;
(1α,5α,6α)-N-[3-(3-nitrobenzyl-3-azabicyclo[3.1.0]hex-6-yl]-2-hydroxy-2-cyclopentyl-2-phenylacetamide;
(1α,5α,6α)-N-[3-(4-chlorophenethyl)-3-azabicyclo[3.1.0]hex-6-yl]-2-hydroxy-2-cyclopentyl-2-phenylacetamide;
(1α,5α,6α)-N-[3-(4-nitrobenzyl)-3-azabicyclo[3.1.0]hex-6-yl]-2-hydroxy-2-cyclopentyl-2-phenylacetamide;

(1α,5α,6α)-N-[3-(4-phenylpropyl)-3-azabicyclo[3.1.0]hex-6-yl]-2-hydroxy-2-cyclopentyl-2-phenylacetamide;

(1α,5α,6α)-N-[3-(3-hydroxybenzyl)-3-azabicyclo[3.1.0]hex-6-yl]-2-hydroxy-2-cyclopentyl-2-phenylacetamide;

(1α,5α,6α)-N-[3-(3-hydroxybenzyl)-3-azabicyclo[3.1.0]hex-6-yl]-2-hydroxy-2-cyclopentyl-2-phenylacetamide;

(1α,5α,6α)-N-[3-(4-t-butylbenzyl)-3-azabicyclo[3.1.0]hex-6-yl]-2-hydroxy-2-hydroxy-2-cyclopentyl-2-phenylacetamide;

(1α,5α,6α)-N-[3-(2-methylquinolinyl)-3-azabicyclo[3.1.0]hex-6-yl]-2-hydroxy-2-cyclopentyl-2-phenylacetamide;

(1α,5α,6α)-N-[3-(3-nitro-4-methoxybenzyl)-3-azabicyclo[3.1.0]hex-6-yl]-2-hydroxy-2-cyclopentyl-2-phenylacetamide;

(1α,5α,6α)-N-[3-(3-nitro-4-hydroxybenzyl)-3-azabicyclo[3.1.0]hex-6-yl]-2-hydroxy-2-cyclopentyl-2-phenylacetamide;

(1α,5α,6α)-N-[3-(3,4-dichlorophenyl)-3-azabicyclo[3.1.0]hex-6-yl]-2-hydroxy-2-cyclopentyl-2-phenylacetamide;

(1α,5α,6α)-N-[3-(3-aminobenzyl)-3-azabicyclo[3.1.0]hex-6-yl]-2-hydroxy-2-cyclopentyl-2-phenylacetamide;

(1α,5α,6α)-N-[3-(6-aminopyridin-2-yl-methyl)-3-azabicyclo[3.1.0]hex-6-yl]-2-hydroxy-2-cyclopentyl-2-phenylacetamide;

(1α,5α,6α)-N-[3-(2-phenoxyethyl)-3-azabicyclo[3.1.0]hex-6-yl]-2-hydroxy-2-cyclopentyl-2-phenylacetamide;

(1α,5α,6α)-N-[3-(3-phenoxypropyl)-3-azabicyclo[3.1.0]hex-6-yl]-2-hydroxy-2-cyclopentyl-2-phenylacetamide;

(1α,5α,6α)-N-[3-(2-methylpyrollyl)-3-azabicyclo[3.1.0]hex-6-yl]-2-hydroxy-2-cyclopentyl-2-phenylacetamide;

(1α,5α,6α)-N-[3-(1,4-benzodioxan-6-yl)-3-methyl-3-azabicyclo[3.1.0]hex-6-yl]-2-hydroxy-2-cyclopentyl-2-phenylacetamide;

(1α,5α,6α)-N-[3-benzyl-3-azabicyclo[3.1.0]hex-6-yl]-2-hydroxy-2-cyclopentyl-2-phenylacetamide;

(1α,5α,6α)-N-[3-(4-methyl-3-pentyl)-3-azabicyclo[3.1.0]hex-6-yl]-2-hydroxy-2-cyclopentyl-2-phenylacetamide;

(1α,5α,6α)-N-[3-(2-(3,4-methylendioxyphenyl)ethyl]-3-azabicyclo-[3.1.0]hex-6-yl]-2-hydroxy-2-cyclobutyl-2-phenylacetamide;

(1α,5α,6α)-N-[3-benzyl-3-azabicyclo-[3.1.0]hex-6-yl]-2-hydroxy-2-cyclopentyl-2-phenylacetamide;

(1α,5α,6α)-N-[3-(4-methyl-3-pentenyl)-3-azabicyclo-[3.1.0]hex-6-yl]-2-hydroxy-2-cyclopropyl-2-phenylacetamide;

(1α,5α,6α)-N-[3-[2-(3,4-methylenedioxyphenyl)ethyl]-3-azabicyclo-[3.1.0]hex-6-yl]-2-hydroxy-2-cyclopropyl-2-phenylacetamide;

(1α,5α,6α)-N-[3-(4-hydroxy-3-methoxybenzyl)-3-azabicyclo-[3.1.0]hex-6-yl]-2-hydroxy-2-cyclopropyl-2-phenylacetamide;

(1α,5α,6α)-N-[3-(3-hydroxy-4-methoxybenzyl]-3-azabicyclo-[3.1.0]hex-6-yl]-2-hydroxy-2-cyclopentyl-2-phenylacetamide;

(1α,5α,6α)-N-[3-(2-phenylcarboethoxyethyl)-3-azabicyclo[3.1.0]hex-6-yl]-2-hydroxy-2-cyclopentyl-2-phenylacetamide;

(1α,5α,6α)-N-[3-(1-(2-hydroxyphenyl)ethyl]-3-azabicyclo[3.1.0]hex-6-yl]-2-hydroxy-2-cyclopentyl-2-phenylacetamide;

(1α,5α,6α)-N-[3-(1-(4-methylphenyl)ethyl]-3-azabicyclo[3.1.0]hex-6-yl]-2-hydroxy-2-cyclopentyl-2-phenylacetamide;

(1α,5α,6α)-N-[3-(1-bromophenylmethylpyridine)-3-azabicyclo-[3.1.0]hex-6-yl]-2-hydroxy-2-cyclopentyl-2-phenylacetamide;

(1α,5α,6α)-N-[3-(4-pyridylmethyl)-3-azabicyclo[3.1.0]hex-6-yl]-2-hydroxy-2-cyclopentyl-2-phenylacetamide;

(1α,5α,6α)-N-[3-(1-indanyl)-3-azabicyclo[3.1.0]hex-6-yl]-2-hydroxy-2-cyclopentyl-2-phenylacetamide;

(1α,5α,6α)-N-[3-(3-methylbenzyl)-3-azabicyclo[3.1.0]hex-6-yl]-2-hydroxy-2-cyclopentyl-2-phenylacetamide;

(1α,5α,6α)-N-[3-(2,4,6-trimethylbenzyl)-3-azabicyclo[3.1.0]hex-6-yl]-2-hydroxy-2-cyclopentyl-2-phenylacetamide;

(1α,5α,6α)-N-[3-(2-(3,4-dimethoxyphenyl)-3-azabicyclo[3.1.0]hex-6-yl]-2-hydroxy-2-cyclopentyl-2-phenylacetamide;

(1α,5α,6α)-N-[3-(2-(3,4-dimethylphenyl)ethyl-3-azabicyclo[3.1.0]hex-6-yl]-2-hydroxy-2-cyclopentyl-2-phenylacetamide;

(1α,5α,6α)-N-[3-pentyl-3-azabicyclo[3.1.0]hex-6-yl]-2-hydroxy-2-cyclopentyl-2-phenylacetamide;

(1α,5α,6α)-N-[3-(4-cyanobenzyl)-3-azabicyclo[3.1.0]hex-6-yl]-2-hydroxy-2-cyclopentyl-2-phenylacetamide;

(1α,5α,6α)-N-[3-(2-cyanobenzyl)-3-azabicyclo[3.1.0]hex-6-yl]-2-hydroxy-2-cyclopentyl-2-phenylacetamide;

(1α,5α,6α)-N-[3-(2,3,4,5,6-pentafluorobenzyl)-3-azabicyclo[3.1.0]hex-6-yl]-2-hydroxy-2-cyclopentyl-2-phenylacetamide;

(1α,5α,6α)-N-[3-(4-cyanobenzyl)-3-azabicyclo-[3.1.0]hex-6-yl]-2-hydroxy-2-cyclohexyl-2-phenylacetamide;

(1α,5α,6α)-N-[3-(3-methylpyridyl)-3-azabicyclocyanobenzyl[3.1.0]hex-6-yl]-2-hydroxy-2-cyclopentyl-2-phenylacetamide;

(1α,5α,6α)-N-[3-(4-bromo-2-methylthienyl)-3-azabicyclo[3.1.0]hex-6-yl]-2-hydroxy-2-cyclohexyl-2-phenylacetamide;

(1α,5α,6α)-N-[3-(1-(phenyl)ethyl)-3-azabicyclo[3.1.0]hex-6-yl]-2-hydroxy-2-cyclohexyl-2-phenylacetamide;

(1α,5α,6α)-N-[3-(2-nitrobenzyl)-3-azabicyclo[3.1.0]hex-6-yl]-2-hydroxy-2-cyclopentyl-2-phenylacetamide;

(1α,5α,6α)-N-[3-(4-methoxycarbonyl]benzyl]-3-azabicyclo[3.1.0]hex-6-yl]-2-hydroxy-2-cyclopentyl-2-phenylacetamide;

(1α,5α,6α)-N-[3-(diphenylmethyl)-3-azabicyclo[3.1.0]hex-6-yl]-2-hydroxy-2-cyclopentyl-2-phenylacetamide;

(1α,5α,6α)-N-[3-(4-carboxybenzyl)-3-azabicyclo[3.1.0]hex-6-yl]-2-hydroxy-2-cyclopentyl-2-phenylacetamide;

(1α,5α,6α)-N-[3-(2-aminobenzyl)-3-azabicyclo[3.1.0]hex-6-yl]-2-hydroxy-2-cyclopentyl-2-phenylacetamide;

(1α,5α,6α)-N-[3-(2-carboethoxypropyl)-3-azabicyclo[3.1.0]hex-6-yl]-2-hydroxy-2-cyclopentyl-2-phenylacetamide;

(1α,5α,6α)-N-[3-(2-(4-acetylphenyl)-3-azabicyclo[3.1.0]hex-6-yl]-2-hydroxy-2-cyclopentyl-2-phenylacetamide;

(1α,5α,6α)-N-[3-(2-(4-methoxycarbonyl)phenyl)ethyl-3-azabicyclo[3.1.0]hex-6-yl]-2-hydroxy-2-cyclopentyl-2-phenylacetamide;

(1α,5α,6α)-N-[3-(3-cyanobenzyl)-3-azabicyclo[3.1.0]hex-6-yl]-2-hydroxy-2-cyclopentyl-2-phenylacetamide;

(1α,5α,6α)-N-[3-(2-cyanobenzyl)-3-azabicyclo[3.1.0]hex-6-yl]-2-hydroxy-2-cyclohexyl-2-phenylacetamide;

(1α,5α,6α)-N-[3-(3-cyanobenzyl)-3-azabicyclo[3.1.0]hex-6-yl]-2-hydroxy-2-cyclohexyl-2-phenylacetamide;

(1α,5α,6α)-N-[3-(3-methylbutyl)-3-azabicyclo[3.1.0]hex-6-yl]-2-hydroxy-2-cyclohexyl-2-phenylacetamide;

(1α,5α,6α)-N-[3-(4-hydroxymethyl phenethyl)-3-azabicyclo[3.1.0]hex-6-yl]-2-hydroxy-2-cyclobentyl-2-phenylacetamide;

(1α,5α,6α)-N-[3-(3-Fluoro-4-aminobenzyl)-3-azabicyclo[3.1.0]hex-6-yl]-2-hydroxy-2-cyclopentyl-2-phenylacetamide;

(1α,5α,6α)-N-[3-(1-(3,4-dimethylphenyl)ethyl)-3-azabicyclo[3.1.0]hex-6-yl]-2-hydroxy-2-cyclopentyl-2-phenylacetamide;

(1α,5α,6α)-N-[3-(2-(3-methylphenoxy)ethyl)-3-azabicyclo[3.1.0]hex-6-yl]-2-hydroxy-2-cyclopentyl-2-phenylacetamide;

(1α,5α,6α)-N-[3-(3-(3-methylphenoxy)propyl)-3-azabicyclo[3.1.0]hex-6-yl]-2-hydroxy-2-cyclopentyl-2-phenylacetamide;

(1α,5α,6α)-N-[3-(2-methylbenzyl)-3-azabicyclo[3.1.0]hex-6-yl]-2-hydroxy-2-cyclopentyl-2-phenylacetamide;

(1α,5α,6α)-N-[3-(2-(2-methylbenzyl)-3-azabicyclo[3.1.0]hex-6-yl]-2-hydroxy-2-cyclopentyl-2-phenylacetamide;

(1α,5α,6α)-N-[3-(1,3-dioxolan-2-yl-methyl)-3-azabicyclo[3.1.0]hex-6-yl]-2-hydroxy-2-cyclopentyl-2-phenylacetamide;

(1α,5α,6α)-N-[3-(2-carboxy)propyl-3-azabicyclo[3.1.0.]hex-6-yl]-2-hydroxy-2-cyclopentyl-2-phenylacetamide;

(1α,5α,6α)-N-[3-(1-phenylethyl)-3-azabicyclo[3.1.0]hex-6-yl]-2-hydroxy-2,2-diphenylacetamide;

(1α,5α,6α)-N-[3-(1-phenylethyl)-3-azabicyclo[3.1.0]hex-6-yl]-2-hydroxy-2-cyclopentyl-2-phenylacetamide;

(1α,5α,6α)-N-[3-(2-(2,3-dihydrobenzofuran-5-yl)ethyl)-3-azabicyclo[3.1.0]hex-6-yl]-2-hydroxy-2-cyclopropyl-2-phenylacetamide;

(1α,5α,6α)-N-[3-(1-phenylethyl)-3-azabicyclo[3.1.0]hex-6-yl]-2-hydroxy-2-cyclopropyl-2-phenylacetamide;

(1α,5α,6α)-N-[3-(1-phenylethyl)-3-azabicyclo[3.1.0]hex-6-yl]-2-hydroxy-2-cyclobutyl-2-phenylacetamide;

(1α,5α,6α)-N-[3-(2-phenylcarboxy)ethyl-3-azabicyclo[3.1.0]hex-6-yl]-2-hydroxy-2-cycloheptyl-2-phenylacetamide;

(1α,5α,6α)-N-[3-(2-(3-indoyl)ethyl)-3-azabicyclo[3.1.0]hex-6-yl]-2-hydroxy-2-cyclohexyl-2-phenylacetamide;

(1α,5α,6α)-N-[3-(2-methylnaphthyl)-3-azabicyclo[3.1.0]hex-6-yl]-2-hydroxy-2-cyclohexyl-2-phenylacetamide;

(1α,5α,6α)-N-[3-(2-indoyl-3-yl)ethyl-3-azabicyclo[3.1.0]hex-6-yl]-2-hydroxy-2-cyclopentyl-2-phenylacetamide;

(1α,5α,6α)-N-[3-hexyl-3-azabicyclo[3.1.0]hex-6-yl]-2-hydroxy-2-cyclopentyl-2-phenylacetamide;

(1α, 5α6α)-N-[3-(1,2,3,4-tetrahydronaphth-1-yl)-3-azabicyclo[3.1.0]hex-6-yl]-2-hydroxy-2-cyclopentyl-2-phenylacetamide;

(1α,5α,6α)-N-[3-(2-chlorobenzyl)-3-azabicyclo[3.1.0]hex-6-yl]-2-hydroxy-2-cyclopentyl-2-phenylacetamide;

(1α,5α,6α)-N-[3-(2-(2-methoxyphenyl)ethyl)-3-azabicyclo[3.1.0]hex-6-yl]-2-hydroxy-2-cyclopentyl-2-phenylacetamide;

(1α,5α,6α)-N-[3-(2-(4-fluorophenyl)ethyl)-3-azabicyclo[3.1.0]hex-6-yl]-2-hydroxy-2-cyclopentyl-2-phenylacetamide;

(1α,5α,6α)-N-[3-(indan-5-yl)ethyl)-3-azabicyclo[3.1.0]hex-6-yl]-2-hydroxy-2-cyclopentyl-2-phenylacetamide;

(1α,5α,6α)-N-[3-(1-(naphth-1-yl)ethyl)-3-azabicyclo[3.1.0]hex-6-yl]-2-hydroxy-2-cyclopentyl-2-phenylacetamide;

(1α,5α,6α)-N-[3-(1-(3,4-methylenedioxyphenyl)ethyl)-3-azabicyclo[3.1.0]hex-6-yl]-2-hydroxy-2-cyclopentyl-2-phenylacetamide;

(1α,5α,6α)-N-[3-(1,2,3,4-tetrahydronaphth-6-yl)ethyl-3-azabicyclo[3.1.0]hex-6-yl]-2-hydroxy-2-cyclopentyl-2-phenylacetamide;

(1α,5α,6α)-N-[3-(1-(cis-(hex-3-enyl)-3-azabicyclo[3.1.0]hex-6-yl]-2-hydroxy-2-cyclopropyl-2-phenylacetamide;

(1α,5α,6α)-N-[3-(1-(trans-hex-3-enyl)-3-azabicyclo[3.1.0]hex-6-yl]-2-hydroxy-2-cyclopropyl-2-phenylacetamide;

(1α,5α,6α)-N-[3-(1-(trans-hex-3-enyl)-3-azabicyclo[3.1.0]-2-hydroxy-2-cyclohexyl-2-phenylacetamide;

(1α,5α,6α)-N-[3-(1-(cis-hex-3-enyl)-3-azabicyclo[3.1.0]hex-6-yl]-2-hydroxy-2-cyclohexyl-2-phenylacetamide;

(1α,5α,6α)-N-[3-(1-(trans-hex-3-enyl)-3-azabicyclo[3.1.0]hex-6-yl]-2-hydroxy-2-cyclopentyl-2-phenylacetamide;

(1α,5α,6α)-N-[3-(1-(cis-hex-3-enyl)-3-azabicyclo[3.1.0]hex-6-yl]-2-hydroxy-2-cyclopentyl-2-phenylacetamide;

(1α,5α,6α)-N-[3-(2-naphthylmethyl)-3-azabicyclo[3.1.0]hex-6-yl]-2-hydroxy-2-cyclopentyl-2-phenylacetamide;

(1α,5α,6α)-N-[3-(2-phenyl-1-methyl)-2-oxoethyl]-3-azabicyclo[3.1.0]hex-6-yl]-2-hydroxy-2-cyclopentyl-2-phenylacetamide;

(1α,5α,6α)-N-[3-(2-(4-carbamoylphenyl)ethyl)-3-azabicyclo[3.1.0]hex-6-yl]-2-hydroxy-2-cyclopentyl-2-phenylacetamide;

(1α,5α,6α)-N-[3-(2-(4-benzyloxycarbonylphenyl)ethyl)-3-azabicyclo[3.1.0]hex-6-yl]-2-hydroxy-2-cyclopentyl-2-phenylacetamide;

(1α,5α,6α)-N-[3-(1-(2-methylpropyl)benzane-3-azabicyclo[3.1.0]hex-6-yl]-2-hydroxy-2-cyclopentyl-2-phenylacetamide;

(1α,5α,6α)-N-[3-(2-(phenyl-1-methyl)-2-oxoethyl)-3-azabicyclo[3.1.0]hex-6-yl]-2-hydroxy-2-cyclohexyl-2-phenylacetamide;

(1α,5α,6α)-N-[3-hexyl-3-azabicyclo[3.1.0]hex-6-yl]-2-hydroxy-2-cyclohexyl-2-phenylacetamide;

(1α,5α,6α)-N-[3-(2-(4-cyanophenyl)ethyl)-3-azabicyclo[3.1.0]hex-6-yl]-2-hydroxy-2-cyclopentyl-2-phenylacetamide;

(1α,5α,6α)-N-[3-(2-(4-sulphamoylphenyl)ethyl)1-3-azabicyclo[3.1.0]hex-6-yl]-2-hydroxy-2-cyclopentyl-2-phenylacetamide;

(1α,5α,6α)-N-[3-cyclohexylmethyl-3-azabicyclo[3.1.0]
hex-6-yl]-2-hydroxy-2-cyclopentyl-2-phenylaceta-
mide;
(1α,5α,6α)-N-[3-benzyl-2-azabicyclo[3.1.0]hex-6-yl]-2,
2-diphenylacetamide;
(1α,5α,6α)-N-[3-benzyl-3-azabicyclo[3.1.0]hex-6-yl]-2-
chloro-2-cyclohexyl-2-phenylacetamide;
(1α,5α,6α)-N-[3-benzyl-3-azabicyclo[3.1.0]hex-6-yl]-2-
cyclohexyl-2-phenylacetamide;
(1α,5α,6α)-N-[3-benzyl-3-azabicyclo[3.1.0]hex-6-yl]-2-
hydroxy-2-phenylacetamide;
(1α,5α,6α)-N-[3-benzyl-3-azabicyclo[3.1.0]hex-6-yl]-2-
cyclopentyl-2-phenylacetamide;
(1α,5α,6α)-N-[3-benzyl-3-azabicyclo[3.1.0]hex-6-yl]-2-
hydroxy-2-phenyl propionamide;
N-methyl-N-(1α,5α,6α)-N-[3-(1-phenyl-ethyl)-3-azabi-
cyclo[3.1.0]-hex-6-yl]-2-cyclopentyl-2-hydroxy-2-
phenylacetamide;
N-methyl-N-(1α,5α,6α)-N-[3-(3,4-methylenedioxy-
ethyl)-3-azabicyclo[3.1.0]-hex-6-yl]-2-cyclopentyl-2-
hydroxy-2-phenylacetamide;
N-methyl-N-(1α,5α,6α)-N-[3-(9-benzyl-3-azabicyclo
[3.1.0]-hex-6-yl]-2-cyclopentyl-2-hydroxy-2-pheny-
lacetamide;
N-methyl-(1α,5α,6α)-N-[3-(3,4-methylenedioxyethyl)-
3-azabicyclo[3.1.0]-hex-6-yl]-2-cyclohexyl-2-hy-
droxy-2-phenylacetamide;
N-methyl-N-(1α,5α,6α)-N-[3-(4-methyl-3-pentenyl)-3-
azabicyclo[3.1.0]-hex-6-yl]-2-cyclohexyl-2-hydroxy-
2-phenylacetamide;
N-methyl-N-(1α,5α,6α)-N-[3-(4-methyl-3-pentenyl)-3-
azabicyclo[3.1.0]-hex-6-yl]-2-cyclopentyl-2-hydroxy-
2-phenylacetamide; and
N-methyl-N-(1α,5α,6α)-N-[3-(4-methyl-3-pentenyl)-3-
azabicyclo[3.1.0]-hex-6-yl]-2-cyclopentyl-2-hydroxy-
2-phenylacetamide L (+)tartarate salt.

8. A pharmaceutical composition comprising a therapeutically effective amount of a compound as defined in any one of claims 1-7 together with pharmaceutically acceptable carriers, excipients or diluents.

9. A method for treating of an animal or a human suffering from a disease or disorder of the respiratory, urinary and gastrointestinal systems,
wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis;
comprising administering to said animal or human, a therapeutically effective amount of a compound having the structure of Formula I,

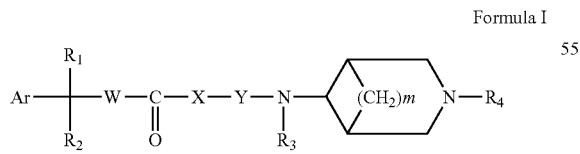

Formula I and its pharmaceutically acceptable salts, pharmaceutically acceptable enantiomers, diastereomers, or N-oxides, wherein
Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), trifluoromethyl cyano, hydroxy, nitro, halogen (e.g. F, Cl, Br or I), lower alkoxy ($C_1$-$C_4$), amino or lower alkylamino($C_1$-$C_4$);

$R_1$ represents a hydrogen, hydroxy, hydroxymethyl, loweralkyl ($C_1$-$C_4$), amino, alkoxy, cycloalkyl ($C_3$-$C_7$), carbamoyl, halogen (e.g. F, Cl, Br, I) or aryl;

$R_2$ represents alkyl, $C_3$-$C_7$ cycloalkyl ring, $C_3$-$C_7$ cycloalkenyl ring, an aryl or a heteroaryl ring having 1 to 2 hetero atoms selected from the group consisting of oxygen, sulphur and nitrogen atoms; the aryl or a hetero aryl ring may be unsubstituted or substituted by one to three substituents independently selected from lower alkyl ($C_1$-$C_4$), trifluoromethyl, cyano, hydroxy, nitro, lower alkoxycarbonyl, halogen, lower alkoxy ($C_1$-$C_4$), unsubstituted amino or lower alkyl ($C_1$-$C_4$) amino;

W represents $(CH_2)p$, where p represents 0 to 1;

X represents an oxygen, sulphur, nitrogen or no atom;

Y represents $CHR_5CO$ wherein $R_5$ represents hydrogen or methyl; or $(CH_2)q$ wherein q represents 0 to 4;

m represents 0 to 2;

$R_3$ represents hydrogen, lower alkyl ($C_1$-$C_4$) or $CO_2C(CH_3)_3$; and $R_4$ represents $C_1$-$C_{15}$ saturated or unsaturated aliphatic hydrocarbon (straight chain or branched) in which any 1 to 6 hydrogen atoms may be substituted with the group independently selected from halogen (e.g. F, Cl, Br, I), carboxylic acid, carboxylic acid ester, aryl, aryloxy, arylalkyl, arylalkenyl, heteroaryl, heteroarylalkyl, heteroarylalkenyl having 1 to 2 hetero atoms selected from the group consisting of nitrogen, oxygen and sulphur with option that any 1 to 5 hydrogen atoms on the ring in said aryl, aryloxy, arylalkyl, arylalkenyl, heteroaryl, heteroarylalkenyl may be substituted with lower alkyl, trifluoromethyl, halogen (F, Cl, Br, I), cyano, nitro, hydroxy, lower ($C_1$-$C_4$) alkoxy, amino, lower ($C_1$-$C_4$) alkylamino, sulphonylamino, amide, carboxylic acid, carboxylic acid ester or benzyl ester.

10. The method according to claim 9 for treatment of an animal or a human suffering from a disease or disorder of the respiratory, urinary and gastrointestinal systems,
wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis;
comprising administering to said animal or human, a therapeutically effective amount of compound having the structure of Formula II and its pharmaceutically

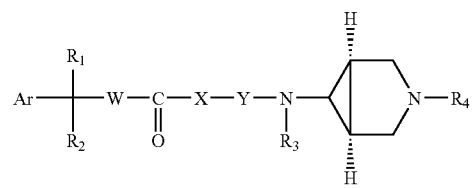

Formula II acceptable salts, pharmaceutically acceptable enantiomers, diastereomers, or N-oxides, wherein Ar, $R_1$, $R_2$, $R_3$, $R_4$, W, X and Y are as defined for Formula I.

11. The method according to claim 9 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis;

comprising administering to said animal or human, a therapeutically effective amount of a compound having the structure of Formula III and its pharmaceutically acceptable salts, pharmaceutically acceptable enantiomers, diastereomers, or N-oxides, wherein Ar, $R_1$, $R_2$, $R_3$ and $R_4$ are as defined for Formula I

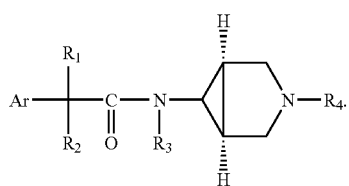

Formula III

12. The method according to claim 9 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis;

comprising administering to said animal or human, a therapeutically effective amount of a compound having the structure of Formula IV and its pharmaceutically acceptable salts, pharmaceutically acceptable enantiomers, diastereomers, or N-oxides, wherein Ar, $R_1$, $R_3$ and $R_4$ are as defined for Formula I and r is 1 to 4

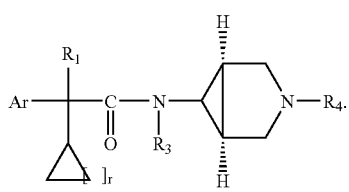

Formula IV

13. The method according to claim 9 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis;

comprising administering to said animal or human, a therapeutically effective amount of a compound having the structure of Formula V and its pharmaceutically acceptable salts, pharmaceutically acceptable enantiomers, diastereomers, or N-oxides, wherein Ar, $R_1$, $R_3$ and $R_4$ are as defined for Formula I and s is 1 to 3

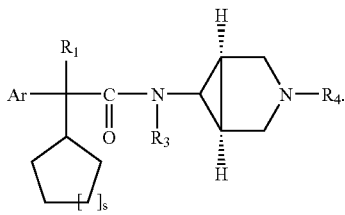

Formula V

14. The method according to claim 9 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis;

comprising administering to said animal or human, a therapeutically effective amount of a compound having the structure of Formula VI and its pharmaceutically acceptable salts, pharmaceutically acceptable enantiomers, diastereomers, or N-oxides, wherein $R_3$, $R_4$ are as defined for Formula I and s is 1 to 3

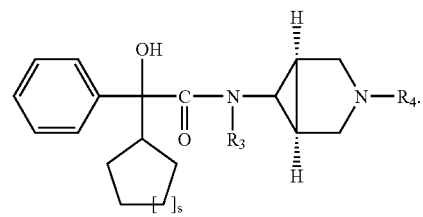

Formula VI

15. The method for treatment of an animal or a human suffering from a disease or disorder of the respiratory, urinary and gastrointestinal systems, wherein the disease or disorder is urinary incontinence, lower urinary tract symptoms, (LUTS), bronchial asthma, chronic obstructive pulmonary disorders (COPD), pulmonary fibrosis, irritable bowel syndrome, obesity, diabetes or gastrointestinal hyperkinesis;

comprising administering to said animal or human, a therapeutically effective amount of the pharmaceutical composition according to claim 8.

16. A process of preparing a compound of Formula I,

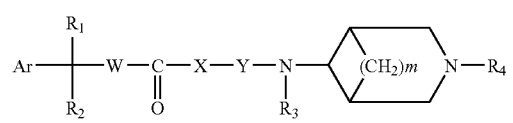

Formula I and its pharmaceutically acceptable salts, pharmaceutically acceptable enantiomers, diastereomers, or N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), trifluoromethyl cyano, hydroxy, nitro, halogen (e.g. F, Cl, Br or I), lower alkoxy ($C_1$-$C_4$), amino or lower alkylamino($C_1$-$C_4$);

$R_1$ represents a hydrogen, hydroxy, hydroxymethyl, loweralkyl($C_1$-$C_4$), amino, alkoxy, cycloalkyl ($C_3$-$C_7$), carbamoyl, halogen (e.g. F, Cl, Br, I) or aryl;

$R_2$ represents alkyl, $C_3$-$C_7$ cycloalkyl ring, $C_3$-$C_7$ cycloalkenyl ring, an aryl or a heteroaryl ring having 1 to 2 hetero atoms selected from the group consisting of oxygen, sulphur and nitrogen atoms; the aryl or a hetero aryl ring may be unsubstituted or substituted by one to three substituents independently selected from lower alkyl ($C_1$-$C_4$), trifluoromethyl, cyano, hydroxy, nitro, lower alkoxycarbonyl, halogen, lower alkoxy ($C_1$-$C_4$), unsubstituted amino or lower alkyl ($C_1$-$C_4$) amino;

W represents $(CH_2)_p$, where p represents 0 to 1;

X represents an oxygen, sulphur, nitrogen or no atom;

Y represents $CHR_5CO$ wherein $R_5$ represents hydrogen or methyl or $(CH_2)q$ wherein q represents 0 to 4;

m represents 0 to 2;

$R_3$ represents hydrogen, lower alkyl ($C_1$-$C_4$) or $CO_2C(CH_3)_3$; and $R_4$ represents $C_1$-$C_{15}$ saturated or unsaturated aliphatic hydrocarbon (straight chain or branched) in which any 1 to 6 hydrogen atoms may be substituted with the group independently selected from halogen (e.g. F, Cl, Br, I), carboxylic acid, carboxylic acid ester, aryl, aryloxy, arylalkyl, arylalkenyl, heteroaryl, heteroarylalkyl, heteroarylalkenyl having 1 to 2 hetero atoms selected from the group consisting of nitrogen, oxygen and sulphur with option that any 1 to 5 hydrogen atoms on the ring in the said aryl, aryloxy, arylalkyl, arylalkenyl, heteroaryl, heteroarylalkenyl may be substituted with lower alkyl, trifluoromethyl, halogen (e.g. F, Cl, Br, I), cyano, nitro, hydroxy, lower ($C_1$-$C_4$) alkoxy, amino, lower ($C_1$-$C_4$) alkylamino, sulphonylamino, amide, carboxylic acid, carboxylic acid ester or benzyl ester, comprising (a) condensing a compound of Formula VIII with a compound of Formula VII

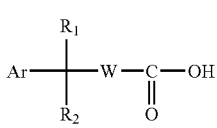

Formula VII

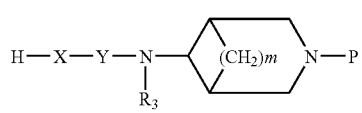

Formual VIII wherein Ar, $R_1$, $R_2$, W, X, Y and $R_3$ have the same meanings as defined earlier for Formula I, to give a protected compound of Formula IX wherein Ar, $R_1$, $R_2$, W, X, Y and $R_3$ are the same as defined earlier and P is a protecting group for an amino group,

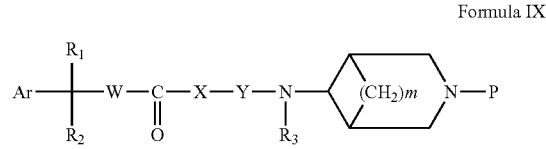

Formula IX (b) deprotecting the compound of Formula IX in the presence of a deprotecting agent to give an unprotected intermediate of Formula X wherein Ar, $R_1$, $R_2$, W, X, Y and $R_3$ as defined earlier, and

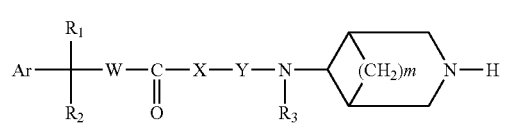

Formula X (c) N-alkylating or benzylating the intermediate of Formula X with a suitable alkylating or benzylating agent to give a compound of Formula I wherein Ar, $R_1$, $R_2$, W, X, Y, $R_3$ and $R_4$ are as defined earlier.

17. The process according to claim 16 wherein P is selected from the group consisting of benzyl and t-butyloxy carbonyl groups.

18. The process according to claim 16 wherein the reaction of a compound of Formula VII with a compound of Formula VII to give a compound of Formula IX is carried out in the presence of a condensing agent which is selected from the group consisting of 1-(3-dimethylaminopropyl)-3-ethyl carbodiimide hydrochloride (EDC) and 1,8-diazabicyclo[5.4.0]undec-7-ene (DBU).

19. The process according to claim 16 wherein the reaction of a compound of Formula VII with a compound of Formula VIII to give a compound of Formula IX is carried out in a suitable solvent selected from the group consisting of N,N-dimethylformamide, dimethylsulfoxide, toluene and xylene.

20. The process according to claim 16 wherein the reaction of a compound of Formula VII with a compound of Formula VIII is carried out at temperature ranging from 0-140° C.

21. The process according to claim 16 wherein the reaction of a compound of Formula IX to give a compound of Formula X is carried out with a deprotecting agent which is selected from the group consisting of palladium on carbon trifluoroacetic acid (TFA) and hydrochloric acid.

22. The process according to claim 16 wherein the deprotection of a compound of Formula IX to give a compound of Formula X is carried out in a suitable organic solvent selected from the group consisting of methanol, ethanol, tetrahydrofuran and acetonitrile.

23. The process according to claim 16 wherein the N-alkylation or benzylation of a compound of Formula X to give a compound of Formula I is carried out with a suitable alkylating or benzylating agent L-$R_4$ wherein L is any leaving group and $R_4$ is as defined earlier.

24. The process according to claim 23 wherein the leaving group is selected from the group consisting of halogen, O-methyl and O-tosyl groups.

25. The process according to claim 23 wherein the N-alkylation or benzylation of a compound of Formula X to give a compound of Formula I is carried out in a suitable organic solvent selected from the group consisting of N,N-dimethylformamide, dimethylsulfoxide, tetrahydrofuran and acetonitrile.

* * * * *